(12) United States Patent
Duval

(10) Patent No.: US 11,903,866 B2
(45) Date of Patent: *Feb. 20, 2024

(54) METHODS AND APPARATUS FOR COLLECTING BODY FLUIDS

(71) Applicant: UR24TECHNOLOGY, INC., Corona Del Mar, CA (US)

(72) Inventor: Landon Duval, Corona Del Mar, CA (US)

(73) Assignee: Ur24Technology, Inc., Corona Del Mar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/657,658

(22) Filed: Apr. 1, 2022

(65) Prior Publication Data

US 2022/0249270 A1 Aug. 11, 2022

Related U.S. Application Data

(63) Continuation of application No. 16/881,601, filed on May 22, 2020, now Pat. No. 11,311,405.

(51) Int. Cl.
*A61F 5/441* (2006.01)
*A61F 5/44* (2006.01)
(Continued)

(52) U.S. Cl.
CPC ............ *A61F 5/441* (2013.01); *A61F 5/4405* (2013.01); *A61F 5/453* (2013.01); *A61F 5/455* (2013.01); *A61F 5/4556* (2013.01)

(58) Field of Classification Search
CPC ........ A61F 5/411; A61F 5/4405; A61F 5/453; A61F 5/455; A61F 5/4556; A61F 5/451
See application file for complete search history.

(56) References Cited

U.S. PATENT DOCUMENTS 660,388 A 10/1900 Moberg et al.
1,742,080 A 12/1929 Jones
(Continued)

FOREIGN PATENT DOCUMENTS

CN 105287084 2/2016
CN 205234739 5/2016
(Continued)

OTHER PUBLICATIONS

International Preliminary Report on Patentability issued in PCT Application No. PCT/US2017/016624, dated Aug. 21, 2018, in 9 pages.
(Continued)

*Primary Examiner* — Benjamin J Klein
*Assistant Examiner* — Hans Kaliher
(74) *Attorney, Agent, or Firm* — Knobbe, Martens, Olson & Bear, LLP

(57) ABSTRACT

Methods and apparatus for collecting fluids discharged from a urethra. An apparatus can include a housing with a rear and front portion a coupled together. A baseplate, inside the housing, includes an angled circumferential side surface adjacent to an inside surface of the housing, a main aperture, and a valve aperture extending through the baseplate. A discharge tube is coupled to the baseplate. An elastomeric tube extends from outside the housing to a termination point past the baseplate within the housing, the baseplate and the housing configured such that the collection tube is pinched and held in place between the baseplate angled circumferential side surface and an inside surface of the vented housing. One-way valves positioned in each valve aperture communicate air through the baseplate into the collection tube. A urethra tube, configured for collecting discharged urine, is positioned in a proximal end of the collection tube.

18 Claims, 37 Drawing Sheets

(51) Int. Cl.
*A61F 5/453* (2006.01)
*A61F 5/455* (2006.01)

(56) References Cited

U.S. PATENT DOCUMENTS

| | | |
|---|---|---|
| 2,483,079 A | 9/1949 | Williams |
| 2,571,357 A | 10/1951 | Charles |
| 2,698,016 A | 12/1954 | Andrade et al. |
| 2,739,595 A | 3/1956 | Coles |
| 2,763,266 A | 9/1956 | Evans |
| 2,842,129 A | 7/1958 | Ernstorff |
| 2,867,215 A | 1/1959 | Horton et al. |
| 2,873,740 A | 2/1959 | Wainwright |
| 3,116,734 A | 1/1964 | Terman |
| 3,194,238 A | 7/1965 | Breece, Jr. |
| 3,421,507 A | 12/1965 | Gresham |
| 3,518,164 A | 4/1967 | Andelin et al. |
| 3,349,768 A | 10/1967 | Xavier |
| 3,424,163 A | 1/1969 | Gravdahl |
| D215,716 S | 10/1969 | Miller |
| 3,528,423 A | 9/1970 | Lee |
| 3,601,125 A | 8/1971 | Moss |
| 3,608,552 A | 9/1971 | Broerman |
| 3,683,914 A | 8/1972 | Crowley |
| 3,742,953 A | 7/1973 | Lee |
| 3,906,952 A | 9/1975 | Zamist |
| 3,918,433 A | 11/1975 | Fuisz |
| 4,023,571 A | 5/1977 | Comerford et al. |
| 4,194,508 A | 3/1980 | Anderson |
| 4,198,979 A | 4/1980 | Cooney et al. |
| 4,200,102 A | 4/1980 | Duhamel et al. |
| 4,239,044 A | 12/1980 | Pavlinch et al. |
| 4,246,901 A | 1/1981 | Frosch et al. |
| 4,270,539 A | 6/1981 | Frosch et al. |
| 4,281,655 A | 8/1981 | Terauchi |
| 4,425,130 A | 1/1984 | DesMarais |
| 4,610,675 A | 9/1986 | Truinfol |
| 4,631,061 A | 12/1986 | Martin |
| 4,664,663 A | 5/1987 | Brier |
| 4,747,166 A | 5/1988 | Kuntz |
| 4,769,099 A | 9/1988 | Therriault et al. |
| 4,795,449 A | 1/1989 | Schneider et al. |
| D299,865 S | 2/1989 | Kamstrup-Larsen et al. |
| 4,882,794 A | 11/1989 | Stewart |
| 4,994,051 A | 2/1991 | Walsh |
| 5,002,541 A | 3/1991 | Conkling et al. |
| 5,049,144 A | 9/1991 | Payton |
| 5,078,707 A | 1/1992 | Klug |
| 5,084,037 A | 1/1992 | Barnett |
| 5,195,997 A | 3/1993 | Carns |
| 5,267,969 A | 12/1993 | Hirsch et al. |
| 5,312,379 A | 5/1994 | Rahe |
| 5,312,383 A | 5/1994 | Kubalak |
| 5,346,483 A | 9/1994 | Thaxton, Sr. |
| 5,366,449 A | 11/1994 | Gilberg |
| 5,413,117 A | 5/1995 | Wills |
| 5,424,265 A | 6/1995 | Weinstein |
| D361,823 S | 8/1995 | Layton et al. |
| 5,514,091 A | 5/1996 | Yoon |
| 5,618,277 A | 4/1997 | Goulter |
| 5,669,893 A | 9/1997 | Tanghoj |
| 5,674,212 A | 10/1997 | Osborn et al. |
| 5,685,870 A | 11/1997 | Sakamoto et al. |
| 5,693,001 A | 12/1997 | Salama |
| 5,797,890 A | 8/1998 | Goulter et al. |
| D409,303 S | 5/1999 | Oepping |
| 5,957,904 A | 9/1999 | Holland |
| 6,120,485 A | 9/2000 | Gustafsson et al. |
| 6,151,721 A | 11/2000 | Whitfield |
| 6,183,454 B1 | 2/2001 | Levine et al. |
| 6,302,303 B1 | 10/2001 | Reynolds |
| 6,394,988 B1 | 5/2002 | Hashimoto |
| D467,338 S | 12/2002 | Rehrig |
| 6,544,242 B1 | 4/2003 | Kido et al. |
| 6,641,567 B1 | 11/2003 | Williams |
| 6,684,414 B1 | 2/2004 | Rehrig |
| 6,699,174 B1 | 3/2004 | Bennett |
| 6,702,793 B1 | 3/2004 | Sweetser |
| 6,740,066 B2 | 5/2004 | Wolff et al. |
| 6,761,710 B2 | 7/2004 | D'acchioli et al. |
| 6,840,925 B2 | 1/2005 | Mishima et al. |
| 6,849,065 B2 | 2/2005 | Schmidt et al. |
| 6,854,427 B2 | 2/2005 | Frink |
| 6,932,797 B2 | 8/2005 | Schmidt et al. |
| 7,018,366 B2 | 3/2006 | Easter |
| 7,358,282 B2 | 4/2008 | Krueger et al. |
| 7,465,683 B2 | 12/2008 | McMurray |
| 7,503,911 B2 | 3/2009 | Mishima et al. |
| 7,588,560 B1 | 9/2009 | Dunlop |
| 7,749,205 B2 | 7/2010 | Tazoe et al. |
| 7,766,887 B2 | 8/2010 | Burns |
| 7,833,169 B2 | 11/2010 | Hannon |
| 7,875,010 B2 | 1/2011 | Frazier et al. |
| 7,931,634 B2 | 4/2011 | Swiecicki et al. |
| 7,993,311 B2 | 8/2011 | Finger et al. |
| 8,177,760 B2 | 5/2012 | Rome et al. |
| 8,187,238 B1 | 5/2012 | Dupree |
| 8,287,508 B1 | 10/2012 | Sanchez |
| 8,328,792 B2 | 12/2012 | Nishtala et al. |
| D674,895 S | 1/2013 | Rubin |
| 8,394,074 B2 | 3/2013 | Piette et al. |
| 8,403,901 B2 | 3/2013 | Dunlop |
| 8,454,568 B2 | 6/2013 | Bourke |
| 8,475,422 B2 | 7/2013 | Wu |
| 8,491,552 B2 | 7/2013 | House |
| 8,603,056 B1 | 12/2013 | Fallis |
| D704,330 S | 5/2014 | Cicatelli |
| 8,998,882 B2 | 4/2015 | Knapp et al. |
| 9,028,460 B2 | 5/2015 | Medeiros |
| 9,033,149 B2 | 5/2015 | Terry |
| D739,006 S | 9/2015 | Tominaga et al. |
| D760,893 S | 7/2016 | Honda et al. |
| D784,528 S | 4/2017 | Burgess et al. |
| D800,334 S | 10/2017 | Kasuto et al. |
| 9,788,992 B2 | 10/2017 | Harvie |
| D802,102 S | 11/2017 | Mursu et al. |
| D818,116 S | 5/2018 | Teufel |
| 9,987,480 B2 | 6/2018 | McDaniel |
| 10,226,376 B2 | 3/2019 | Sanchez et al. |
| D851,238 S | 6/2019 | Ratner et al. |
| D851,747 S | 6/2019 | Hu |
| 10,376,406 B2 | 8/2019 | Newton |
| 10,376,407 B2 | 8/2019 | Newton |
| 10,390,989 B2 | 8/2019 | Sanchez et al. |
| D864,774 S | 10/2019 | Lei et al. |
| D873,996 S | 1/2020 | Sanders et al. |
| 10,675,175 B2 | 6/2020 | Holt |
| 10,682,124 B2 | 6/2020 | Duvall |
| 10,690,655 B2 | 6/2020 | Duvall |
| D896,930 S | 9/2020 | Vranish |
| D901,036 S | 11/2020 | Wahba et al. |
| D910,200 S | 2/2021 | Reber et al. |
| D920,535 S | 5/2021 | Crabtree et al. |
| D923,195 S | 6/2021 | Harding et al. |
| D928,946 S | 8/2021 | Sanchez et al. |
| D929,576 S | 8/2021 | Motomura et al. |
| D929,578 S | 8/2021 | Johannes et al. |
| D930,184 S | 9/2021 | Johnson |
| 11,141,307 B2 | 10/2021 | Doreswamy |
| D938,062 S | 12/2021 | Werth et al. |
| 11,246,573 B2 | 2/2022 | Duvall |
| 2002/0138058 A1 | 9/2002 | Mishima et al. |
| 2003/0004436 A1 | 1/2003 | Schmidt et al. |
| 2003/0010700 A1 | 1/2003 | Schmidt et al. |
| 2003/0185330 A1 | 10/2003 | Hessel et al. |
| 2003/0208112 A1 | 11/2003 | Schmidt et al. |
| 2004/0015141 A1 | 1/2004 | Cheng et al. |
| 2004/0035372 A1 | 2/2004 | Frink |
| 2004/0068780 A1 | 4/2004 | Scott |
| 2004/0079687 A1 | 4/2004 | Muller et al. |
| 2004/0138638 A1 | 7/2004 | Mishima et al. |
| 2004/0143229 A1 | 7/2004 | Easter |
| 2004/0236292 A1 | 11/2004 | Tazoe et al. |
| 2005/0075615 A1 | 4/2005 | Bonham |

(56) References Cited

U.S. PATENT DOCUMENTS

| | | |
|---|---|---|
| 2005/0101939 A1 | 5/2005 | Mitchell |
| 2005/0112975 A1 | 5/2005 | McMurray |
| 2005/0112976 A1 | 5/2005 | McMurray et al. |
| 2005/0137557 A1 | 6/2005 | Swiecicki et al. |
| 2006/0015080 A1 | 1/2006 | Mahnensmith |
| 2006/0069359 A1 | 3/2006 | Dipalma et al. |
| 2006/0155214 A1 | 7/2006 | Wightman |
| 2007/0035405 A1 | 2/2007 | Wada et al. |
| 2007/0088327 A1 | 4/2007 | Guala |
| 2007/0225668 A1 | 9/2007 | Otto |
| 2007/0265589 A1 | 11/2007 | Kitamura |
| 2008/0183157 A1 | 7/2008 | Walters |
| 2008/0281282 A1 | 11/2008 | Finger et al. |
| 2008/0287894 A1 | 11/2008 | Van Den et al. |
| 2008/0300448 A1 | 12/2008 | Frazier et al. |
| 2009/0048569 A1 | 2/2009 | Salehi |
| 2009/0078023 A1 | 3/2009 | Mutharasan et al. |
| 2009/0131916 A1 | 5/2009 | Chiu et al. |
| 2009/0270822 A1 | 10/2009 | Medeiros |
| 2009/0306610 A1 | 12/2009 | Van Den et al. |
| 2010/0010459 A1 | 1/2010 | Piette et al. |
| 2010/0234820 A1 | 9/2010 | Tsai et al. |
| 2010/0274156 A1 | 10/2010 | Gorres |
| 2010/0278518 A1 | 11/2010 | Gordon |
| 2011/0028922 A1 | 2/2011 | Kay et al. |
| 2011/0028944 A1 | 2/2011 | Chiu et al. |
| 2011/0040271 A1 | 2/2011 | Rogers |
| 2011/0046514 A1 | 2/2011 | Greenwald et al. |
| 2011/0064586 A1 | 3/2011 | Matsumiya |
| 2011/0178425 A1 | 7/2011 | Nishtala et al. |
| 2011/0251572 A1 | 10/2011 | Nishtala et al. |
| 2011/0265889 A1 | 11/2011 | Tanaka et al. |
| 2013/0053804 A1 | 2/2013 | Sorensen et al. |
| 2015/0112228 A1 | 4/2015 | Ekema et al. |
| 2015/0320583 A1 | 11/2015 | Harvie |
| 2016/0310711 A1 | 10/2016 | Luxon et al. |
| 2017/0196726 A1 | 7/2017 | SanAntonio |
| 2017/0238911 A1* | 8/2017 | Duval .................. A61B 5/207 |
| 2017/0280783 A1 | 10/2017 | Nouh |
| 2017/0333244 A1 | 11/2017 | Laniado |
| 2017/0363237 A1 | 12/2017 | Pepe et al. |
| 2018/0031461 A1 | 2/2018 | Steckmann et al. |
| 2018/0098877 A1 | 7/2018 | Pierson |
| 2018/0188231 A1 | 7/2018 | Barakat et al. |
| 2018/0228642 A1 | 8/2018 | Davis |
| 2018/0256386 A1 | 9/2018 | Pierson |
| 2019/0021899 A1 | 1/2019 | Vlet |
| 2019/0038451 A1 | 2/2019 | Harvie |
| 2019/0314189 A1 | 10/2019 | Acosta |
| 2020/0229964 A1 | 7/2020 | Staali et al. |
| 2021/0000637 A1 | 1/2021 | VanMiddendorp et al. |
| 2021/0023279 A1 | 1/2021 | Radl et al. |
| 2021/0038423 A1 | 2/2021 | Marvinac |
| 2021/0059853 A1 | 3/2021 | Davis et al. |
| 2021/0113749 A1 | 4/2021 | Radl et al. |
| 2021/0154043 A1* | 5/2021 | Proctor .................. A61F 5/453 |
| 2021/0170079 A1 | 6/2021 | Radl et al. |
| 2021/0177643 A1 | 6/2021 | Challa et al. |
| 2021/0267787 A1* | 9/2021 | Nazemi .................. A61M 1/71 |
| 2021/0285584 A1 | 9/2021 | Ravisankar et al. |
| 2021/0361463 A1 | 11/2021 | Duval |
| 2021/0393433 A1 | 12/2021 | Godinez |
| 2021/0401613 A1 | 12/2021 | Chiang |

FOREIGN PATENT DOCUMENTS

| | | |
|---|---|---|
| CN | 205683177 | 11/2016 |
| CN | 206372178 | 8/2017 |
| CN | 207306773 | 5/2018 |
| CN | 208525189 | 2/2019 |
| CN | 209899730 | 1/2020 |
| CN | 210250222 | 4/2020 |
| CN | 210962545 | 7/2020 |
| CN | 212186998 | 12/2020 |
| CN | 212214090 | 12/2020 |
| CN | 213346264 | 6/2021 |
| CN | 213430912 | 6/2021 |
| CN | 214858088 | 11/2021 |
| CN | 113730081 | 12/2021 |
| DE | 19602299 | 7/1997 |
| DE | 102007020517 | 7/2008 |
| DE | 102013011493 | 2/2014 |
| EP | 0613355 | 1/1997 |
| EP | 0 951 881 | 6/2000 |
| FR | 2690842 | 11/1993 |
| GB | 8814874 | 1/1989 |
| JP | H 11502736 | 3/1999 |
| JP | 2001-087298 | 4/2001 |
| JP | 2008511360 | 4/2008 |
| JP | 2012-509489 | 11/2008 |
| JP | 2010-166954 | 8/2010 |
| JP | 2015-147040 | 8/2015 |
| JP | 5911232 | 4/2016 |
| JP | 2019-512672 | 5/2019 |
| KR | 20160038625 | 4/2016 |
| NL | 8601391 | 10/1987 |
| SE | 467086 | 5/1992 |
| TW | M564441 | 8/2018 |
| TW | 202200092 | 1/2022 |
| WO | WO 1996/011652 | 4/1996 |
| WO | WO 1997/001316 | 1/1997 |
| WO | WO 03022333 | 3/2003 |
| WO | WO 2004/019836 | 3/2004 |
| WO | WO 2005/051252 | 6/2005 |
| WO | WO 2007/058461 | 5/2007 |
| WO | WO 2008/102808 | 8/2008 |
| WO | WO 2009/004291 | 1/2009 |
| WO | WO 2017/142723 | 8/2017 |
| WO | WO 2017/142724 | 8/2017 |
| WO | WO 2021/007345 | 1/2021 |
| WO | WO 2021/007349 | 1/2021 |
| WO | WO 2021090621 | 5/2021 |

OTHER PUBLICATIONS

International Preliminary Report on Patentability issued in PCT Application No. PCT/US2017/016626, dated Aug. 21, 2018, in 6 pages.

International Search Report & Written Opinion issued in application No. PCT/US2021/020930, dated Sep. 1, 2021.

International Search Report and Written Opinion issued in PCT Application No. PCT/US2017/016624, dated Apr. 28, 2017, in 11 pages.

International Search Report and Written Opinion issued in PCT Application No. PCT/US2017/016626, dated Apr. 21, 2017, in 7 pages.

Newman, D., Excerpts from The Urinary Incontinence Sourcebook, Lowell House, 1997, in 23 pages.

Notice of Allowance issued in JP application No. 2018-543605, dated Jan. 5, 2021.

UR24 Technology, Inc [@Ur24T]. "See how our external catheter systems stack up to competitors in design, efficacy, comfort, and ease of use. https://ur24technology.com/our-product ." Twitter.com, Published: [Jun. 16, 2021], Site Visited: [Jan. 7, 2022], URL: <https://mobile.twitter.com/Ur24T/status/14052106399954497536>. (Year: 2021).

* cited by examiner

SECTION B-B

Baseplate 40

Baseplate 40

SECTION E-E

Baseplate 40

Urethra Tube - Male 70

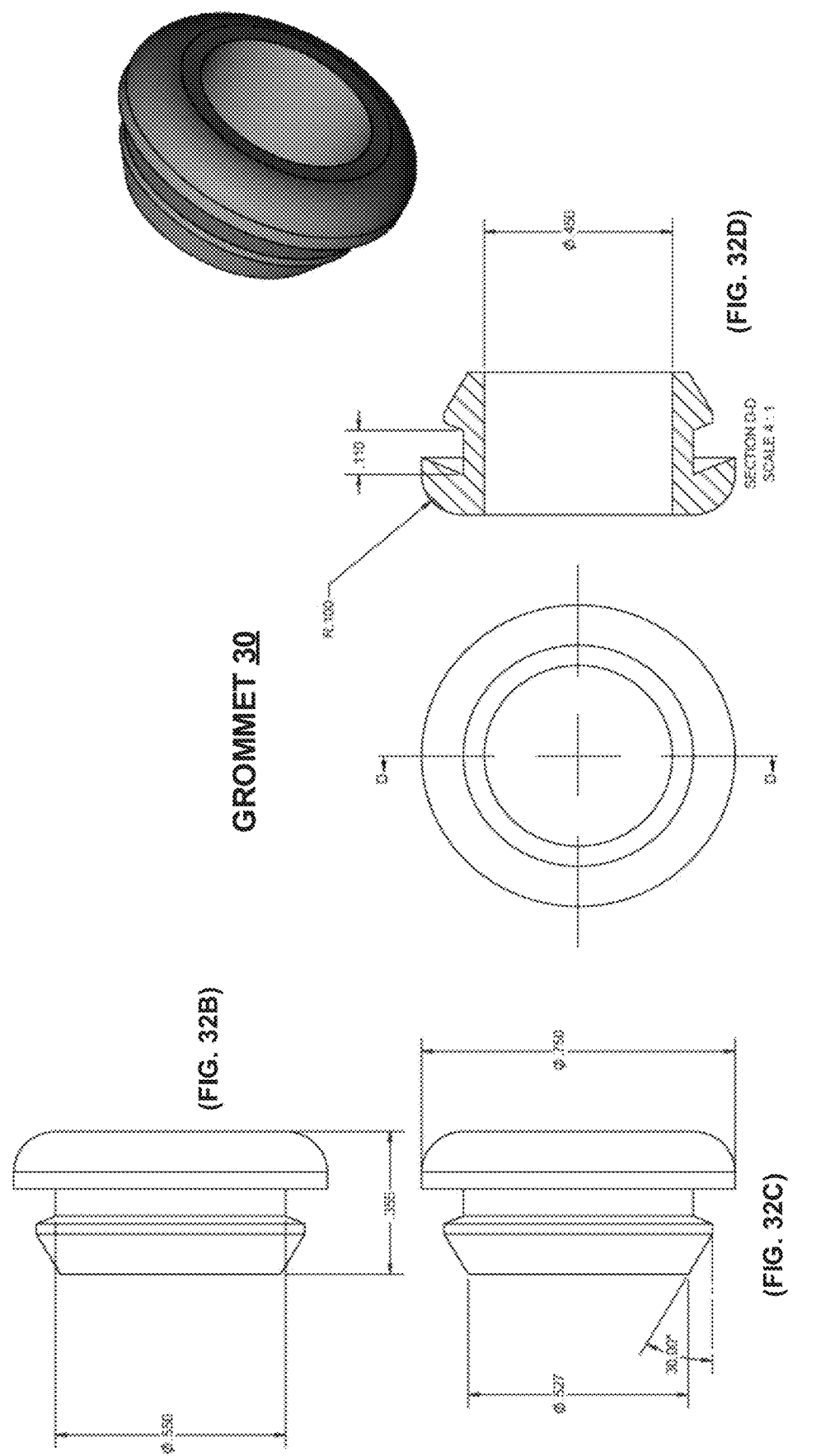

METHODS AND APPARATUS FOR COLLECTING BODY FLUIDS

PRIORITY AND RELATED APPLICATIONS

This application is a continuation of U.S. application Ser. No. 16/881,601, filed May 22, 2020. This application is related to U.S. patent application Ser. No. 17/586,055, filed Jan. 27, 2022, U.S. patent application Ser. No. 16/901,614, filed Jun. 15, 2020, now U.S. Pat. No. 11,246,573, U.S. patent application Ser. No. 15/416,272, filed Jan. 26, 2017, now U.S. Pat. No. 10,682,124, and U.S. patent application Ser. No. 15/412,049, filed Jan. 22, 2017, now U.S. Pat. No. 10,690,655. Each of the above-listed applications is incorporated by reference herein in its entirety.

TECHNICAL FIELD

The present disclosure relates to devices and methods for the collection of body fluids, and more particularly to methods and apparatus for collecting urine from a male or female patient.

BACKGROUND

Urinary collection and analysis for medical reasons may be managed with absorbent diapers, in-dwelling urinary catheters and/or external, non-invasive urine collection devices. However, diapers are associated with a high rate of skin breakdown and decubitus ulcer formation while indwelling urinary catheters are a leading cause of urinary tract infections. In addition, urinary catheters may be difficult to attach for use, difficult to detach when desired, and difficult to re-attach when needed again. External non-invasive urine collection devices can be cumbersome and ineffective for attaching to a male or female urethra when a patient is mobile. Accordingly, there has been a great demand for non-invasive external incontinence devices for collecting human urine without exposing the body to continuous urine contact.

SUMMARY

Embodiments of systems, methods, and devices (apparatus) for collecting body fluids are described and illustrated herein.

One innovation includes a fluid collector apparatus comprising a vented housing having a rear housing having a proximal end, a distal end, and a vent extending through a surface of the rear housing, the distal end including a circular first aperture, the proximal end including an outer edge that surrounds a perimeter of a second aperture, where the perimeter of the second aperture being larger than a perimeter of the first aperture. The vented housing further includes a front housing having a proximal end and a distal end, the proximal end having an outer edge that defines a perimeter of a first aperture and the distal end having an outer edge that defines a perimeter of a second aperture, the proximal end of the rear housing releasably coupled to the distal end of the front housing. The fluid collector apparatus may include a grommet positioned in the rear housing first aperture such that a portion of the grommet extends inside of the rear housing and a portion of the grommet extends exterior to the rear housing, the grommet protecting an adjacently disposed portion of a discharge tube. The fluid collector apparatus further includes a baseplate positioned inside the vented housing, the baseplate having a distal side aligned towards the distal end of the rear housing and a proximal side opposite the distal side, the baseplate having a circumferential side surface on an outer portion of a circumferential edge wall. The circumferential side surface may be angled, the edge wall extending from a proximal surface of the baseplate where a cross-sectional diameter of a distal portion of the edge wall is larger than a cross-sectional diameter of a proximal portion of the edge wall, the angled side surface positioned proximate to an inside surface of the vented housing. The baseplate includes a main aperture for communicating fluids (e.g., urine) extending through a portion of the baseplate and a valve aperture extending through the baseplate between the main aperture and the side surface of the baseplate. The fluid collector apparatus further includes a discharge tube and a collection tube coupled to be in fluid communication with each other. The discharge tube has a distal end and a proximal end, the proximal end may extend through the grommet and the rear housing, and into the distal side of the baseplate and coupled to the baseplate. The collection tube is an elastomeric tube (e.g., made from silicone) and has a distal end and a proximal end, the distal end extending into the vented housing through the first aperture of the front housing. The distal end of the collection tube interfaces with the baseplate such that the baseplate may seal the distal end of the collection tube. For example, the distal end of the collection tube extends around and past the baseplate to a termination point within the vented housing such that at least a portion of the baseplate is inside the collection tube. The baseplate may be positioned entirely inside the distal end of the collection tube. The baseplate may be positioned to be partially inside the distal end of the collection tube. The baseplate and the vented housing are configured such that the collection tube is pinched and held in place with an interference fit between a side of the baseplate and an inside surface of the vented housing. The apparatus includes a valve positioned in the vented housing and mounted in a valve aperture. The valve may extend all the way through the baseplate. The valve is configured to allow air to flow from inside of the vented housing through the valve (and through the baseplate), and into the distal end of the collection tube between the baseplate and the proximal end of the collection tube. The apparatus may also include a urethra tube configured to interface with a person to collect urine. The urethra tube is positioned in the proximal end of the collection tube, the collection tube conforming to the exterior shape of the urethra tube. In some embodiments, one or more of the collection tube, the discharge tube, and the housing, can be translucent or transparent such that urine in the collection tube or the discharge tube is visible to an observer of the fluid collection apparatus. A urethra tube for the fluid collection apparatus for a male patient may be positioned inside a portion of the collection tube, and may provide structural support to the collection tube to prevent it from collapsing inward (e.g., under suction). A urethra tube for the fluid collection apparatus for a female patient may be positioned entirely inside the proximal end of the collection tube. In some implementations, a urethra tube for the fluid collection apparatus for a female patient may be positioned partially inside the proximal end of the collection tube (for example, for an embodiment where the urethra tube is configured with a certain shape or size that is larger than can fit inside the collection tube.

Embodiments of the fluid collection apparatus can have one or more other features. For example, the apparatus may include a fluid sensor positioned in the housing and adapted to produce a first signal when fluid is detected in the collection tube. The apparatus may have one or more sensors positioned within the housing. A sensor may generate a signal indicate of the presence or, of a characteristic of, moisture, blood, sodium chloride, protein, or calcium, or another substance. The apparatus may include a vacuum pump coupled to the distal end of the interconnection tube and a collection vessel. The vacuum pump may be configured to be activated by the first signal to produce a vacuum in the interconnection tube to move fluid in the collection tube to the collection vessel. In some embodiments, the baseplate may include two valve apertures. In such embodiments, the fluid collection apparatus may include two valves. The baseplate may include three valve apertures. In such embodiments, the fluid collection apparatus may include three valves. The baseplate may include four valve apertures, and in such embodiments, the fluid collection apparatus may include four valves. The valve may be a one-way valve that provides airflow air within the vented housing into a chamber created in part by the proximal side of the baseplate and the collection tube.

The baseplate may be disc-shaped. The baseplate side may include a circumferential ridge positioned between the angled side surface and the distal side of the baseplate. The baseplate may include at least two circumferential ridges positioned between the angled side surface and the distal side of the baseplate. Each circumferential ridge may contact the collection tube and holds the collection tube in an interference fit against an inside portion of the vented housing. The angled side surface may contact the collection tube and may hold the collection tube in an interference fit against an inside portion of the vented housing. The angled side surface and/or each circumferential ridge may compress the collection tube and hold the collection tube against an inside portion of the vented housing. The main aperture may be in a center portion of the baseplate. The main aperture may be aligned with an axis of the baseplate. The proximal end of the discharge tube may extend into the main aperture and at least partially through at least a portion of the baseplate. The proximal end of the discharge tube may be coupled to the baseplate. The proximal end of the discharge tube may include coupling structure that couples the discharge tube to the baseplate. The coupling structure may be formed as part of the discharge tube. The coupling structure may be attached to the discharge tube. The apparatus may further include an O-ring positioned around the main aperture. The O-ring (or another connector) may fit around the proximal end of the discharge tube that extends through the baseplate, and couples the discharge tube to the baseplate. The valve may include a proximal end that extends through the baseplate. The proximal end of the valve may include a projection that contacts the O-ring and couples the valve to the baseplate. The proximal end of the valve may include a projection that extends over a portion of the O-ring and couples the O-ring to the baseplate. An axis of the valve aperture may be aligned in parallel with an axis of the main aperture. An axis of the valve aperture may be aligned at angle with an axis of the main aperture. An axis may extend through the center of the valve aperture such that the axis of the valve aperture is angled towards a center axis of the main aperture. The collection tube may comprise silicon. The collection tube to be highly deformable. The termination point where the collection tube ends in the housing may be within the rear housing. The baseplate may be positioned in the vented housing such that the baseplate angled side surface holds the collection tube against a portion of an inside surface of the front housing. The contact between the baseplate and the collection tube, and the collection tube and the inside surface of the vented housing, may be the only coupling mechanism of the collection tube to the vented housing. The urethra tube may be positioned completely inside the proximal end of the collection tube. The urethra tube may be positioned partially inside the proximal end of the collection tube. The urethra tube may include a distal end and a proximal end, the distal end of the urethra being positioned inside the collection tube extending towards the baseplate and the proximal end of the urethra tube positioned inside the proximal end of the collection tube. The collection tube may be stretched over the urethra tube such that the collection tube conforms to the shape of the urethra tube. For example, such that the collection tube is deformed to the shape, size, and/or angle of the urethra tube. The urethra tube may be shaped and sized to interface with a urethra of a female subject. The urethra tube may include a flared proximal end contoured for sealing a female's urethra. The urethra tube may be shaped and sized to interface with a urethra of a male subject. The urethra tube may be contoured for a tight-fitting around a penis received therein. The apparatus may also include a vacuum pump coupled to the distal end of the discharge tube. The apparatus may include a sensor coupled to the baseplate and configured to detect the presence of urine. The apparatus may be incorporated with a garment. The apparatus may be connected with a garment. The garment may be, for example, underwear, underpants, panties, a diaper, or similar item, that is worn by an individual when using the apparatus.

Another innovation includes a fluid collector apparatus comprising a vented housing including a rear housing having a proximal end, a distal end, and a vent extending through a surface of the rear housing, a front housing having a proximal end and a distal end, the proximal end having an outer edge that defines a perimeter of a first aperture and the distal end having an outer edge that defines a perimeter of a second aperture, the proximal end of the rear housing releasably coupled to the distal end of the front housing, a baseplate positioned inside the vented housing, the baseplate having a circumferential angled side surface on an outer portion of a circumferential edge wall, the angled side surface positioned proximate to an inside surface of the vented housing, the baseplate including a main aperture for communicating fluids extending through a portion of the baseplate and a valve aperture extending through the baseplate between the main aperture and the side surface, a discharge tube having a distal end extending outside of the vented housing and a proximal end coupled to the baseplate, an elastomeric collection tube having a distal end and a proximal end, the distal end extending into the vented housing through the first aperture of the front housing and around and past the baseplate to a termination point within the vented housing such that the baseplate is positioned inside the collection tube and normal to the collection tube with the angled side surface contacting an inside surface of the collection tube, the collection tube held in place with an interference fit between the baseplate and an inside surface of the vented housing and a valve positioned in the vented housing and extending through the valve aperture, the valve configured to allow air to flow from inside of the vented housing through the valve and into the collection tube, and a urethra tube positioned in the proximal end of the collection tube such that the proximal end of the collection tube conforms to the shape of the urethra tube.

Another innovation includes a fluid collector apparatus comprising a vented housing including a rear housing having a proximal end, a distal end, and a vent extending through a surface of the rear housing, a front housing having a proximal end and a distal end, the proximal end having an outer edge that defines a perimeter of a first aperture and the distal end having an outer edge that defines a perimeter of a second aperture, the proximal end of the rear housing releasably coupled to the distal end of the front housing.

Another innovation includes a fluid collector apparatus comprising a housing, a baseplate positioned inside the housing, the baseplate having a circumferential angled side surface on an outer portion of a circumferential edge wall, the angled side surface positioned proximate to an inside surface of the housing, the baseplate including a main aperture for communicating fluids extending through a portion of the baseplate and a valve aperture extending through the baseplate between the main aperture and the side surface.

Another innovation includes a fluid collector apparatus comprising an elastomeric collection tube having a distal end and a proximal end, the distal end configured to extend into a housing through an aperture of the housing, and a urethra tube positioned in the proximal end of the collection tube such that the proximal end of the collection tube conforms to the shape of the urethra tube.

Another innovation includes a method of collecting fluid from a urethra, the method comprising providing a fluid collection apparatus having a vented housing including a rear housing having a proximal end, a distal end, and a vent extending through a surface of the rear housing, and a front housing having a proximal end and a distal end, the proximal end having an outer edge that defines a perimeter of a first aperture and the distal end having an outer edge that defines a perimeter of a second aperture, the proximal end of the rear housing releasably coupleable to the distal end of the front housing, a baseplate, having a circumferential angled side surface on an outer portion of a circumferential edge wall, the angled side surface configured to be positioned proximate to an inside surface of the vented housing, the baseplate including a main aperture for communicating fluids extending through a portion of the baseplate and a valve aperture extending through the baseplate between the main aperture and the side surface, and a valve mounted to the baseplate and through each of the valve apertures, coupling a proximal end of discharge tube to the baseplate such that a distal end extends outside of the vented housing through an aperture in the distal end of the rear housing, coupling a distal end of an elastomeric collection tube to the baseplate by inserting the baseplate into the distal end of the collection tube such that the distal end of the collection tube extends into the vented housing past the baseplate to a termination point within the vented housing such that the baseplate is positioned inside the collection tube and normal to the collection tube with the angled side surface contacting an inside surface of the collection tube and the collection tube held in place with an interference fit between the baseplate and an inside surface of the vented housing, inserting a urethra tube in a proximal end of the collection tube such that the proximal end of the collection tube conforms to the shape of the urethra tube, and receiving a body fluid in the urethra tube.

BRIEF DESCRIPTION OF THE DRAWINGS

The features and advantages of the embodiments described herein will become more fully apparent from the following description and appended claims, taken in conjunction with the accompanying drawings. These drawings depict only certain embodiments in accordance with the disclosure and are not to be considered limiting of its scope. In the drawings, similar reference numbers or symbols typically identify similar components, unless context dictates otherwise. In some instances, the drawings may not be drawn to scale.

FIG. 32A illustrates a set of schematics of an example of a grommet 30 that is positioned in an aperture of the rear housing.

DETAILED DESCRIPTION

Figure 1:
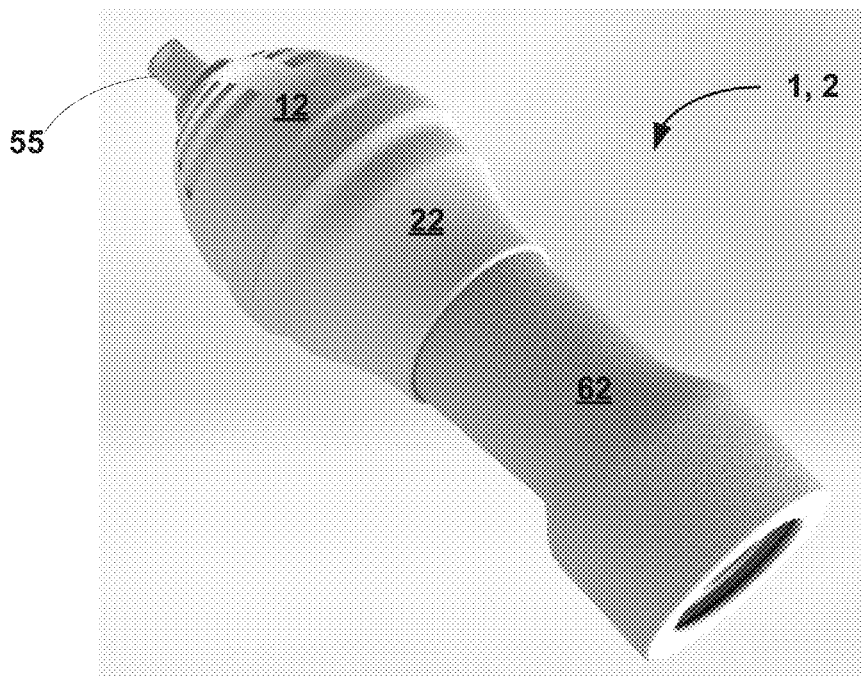
FIG. 1 is a perspective view of the first and second embodiment of a fluid collection apparatus illustrated in FIGS. 4 and 13.

Embodiments of systems, methods, and apparatus for collecting body fluids each can have several aspects (features), no single aspect of which is solely responsible for its desirable attributes. Without limiting the scope of the claims that follow, some of the aspects are described below. Various features of the embodiments described below may be included on an apparatus to collect body fluids from a subject (e.g., a human or an animal). While the disclosure is written in the context of fluid collection for a human subject, the methods and apparatus disclosed herein can also be used on an animal. The drawings referred to illustrate various features that can be included in various implementations of examples of a fluid collection apparatus that is positioned external to a subject's body (sometimes referred to herein simply as the/an "apparatus" for ease of reference). In some examples, for clarity of illustration, not all of the features of a particular fluid collection apparatus are necessarily included in a particular figure. Various illustrated or described implementations of a fluid collection apparatus can also have additional features, including features that are illustrated or described elsewhere herein. Illustrations in the drawing sheets presented herein are examples only and should not be taken as limiting.

The embodiments of a fluid collection apparatus disclosed herein address many of problems in current fluid collection apparatus. Many patients, male and female, have a need for non-invasive external incontinence devices for collecting human urine without exposing the body to continuous urine contact. There is also a need for an external incontinence device which can be applied with a consistent spatial orientation to allow leak-free use, especially for females. Preparing an external incontinence device for use by a male or female patient can include various assembly steps, which can be time-consuming and may be difficult to perform quickly. For example, some external incontinence devices may require manually coupling a urine discharge tube to the external incontinence device to form a leak-proof connection, and coupling a urine intake tube to the external incontinence device to form a leak-proof connection, and some external incontinence devices require manually coupling a urethra interface tube (or receiver) to the external incontinence device—all of which are time consuming. Furthermore, such operations can be difficult to perform while wearing gloves. In addition, different patients (e.g., male/female) may also have different needs for configurations of the external incontinence device, which can increase the variety of external incontinence devices for each of the patient's needs. Therefore, there is a need for an easier to configure an external incontinence device to prepare it for immediate patient use. In addition, there is a need to minimize the number of different external incontinence devices and components that are kept on-hand. The disclosed fluid collection apparatus designed to be leak free, comfortable to wear, lightweight, and easily attached and detached to a patient. The fluid collection apparatus may be disposable. The fluid collection apparatus may be formed of transparent or translucent materials such that urine discharged into the apparatus is visible to a medical practitioner and/or a patient. The fluid collection apparatus may be provided fully assembled in a sterilized pouch so that it is ready for immediate use. The fluid collection apparatus may be provided in a "male version" or a "female version," each version configured to fit any patient. If a special fitting is required, for example for a female version of the apparatus, a urethra tube can be designed to be incorporated into the apparatus without having to change any other components.

The fluid collection apparatus can be worn at times when urination is expected or desired and may be disconnected and removed from, and reconnected to an individual at will. The fluid collection apparatus may generally include a collection tube, a vented housing (having a variety of components therein), and a discharge tube. The collection tube is a flexible deformable material (e.g., silicone). The collection tube may be adapted to conform to a desired size and shape by a urethra tube, which is inserted into the proximal end of the collection tube. That is, the collection tube may deform to the shape, size, and angle of an exterior surface of the urethra tube inserted into the collection tube.

In an example of a fluid collection apparatus for a male patient, the collection tube (being deformable) can be adapted for engagement with a male urethra by receiving an individual's penis. A urethra tube, inserted in the collection tube, may be used to resize or re-shape the collection to for a more desirable fit. A urethra tube inserted into the collection tube can also provide the collection tube additional internal support. For example, a cylindrical urethra tube inserted into the proximal end of the collection tube and positioned near the baseplate can provide internal support to the collection tube such that it does not collapse when a suction is applied to the discharge tube, and a corresponding vacuum is produced in the "chamber" surrounded by the baseplate (sealing the distal end of the collection tube) and the sides of the collection tube on the proximal side of the baseplate. In some embodiments, the male urethra tube is from ¼"-5" long. For example, in some embodiments, the male urethra tube may have a length of ½", 1" 1.5",2", 2.5",3". 3.5",4", 4.5", or 5" (+/−¼"). In some embodiments, two or more male urethra tubes may be inserted into the collection tube to provide internal support to the collection tube and/or to change the size or shape the collection tube.

In an example of a collection apparatus for a female patient, a urethra tube inserted into the proximal end of the collection tube can adapt the collection tube (e.g., change the shape and/or size of the collection tube) to engage a female urethra for improved sealing of the collection tube with the patient. The urethra tube may have a flared end that is larger on the proximal end than the distal end, the flared end allowing a better fit/engagement with a female urethra. The urethra tube may also have an angled portion allowing a better fit/engagement with a female urethra. For example, the urethra tube may have a first portion that has first longitudinal axis and a second portion that has a second longitudinal axis, the first longitudinal axis and the second longitudinal axis aligned at an angle, for example, an angle of between about 0° to about 90°. In some embodiments, such an angle may be in the range of about 5° to about 25°, for example, about 15°. Adapting the collection tube by inserting the urethra tube into the collection tube advantageously allows the same collection tube (same part/component) to be configured for use with male or female patients, thus minimizing the number of different collection tubes (e.g., sizes, shapes, angles, etc.) that need to be kept in stock (e.g., one collection tube can be used for many or all patients).

The collection tube and the discharge tube are coupled to the vented housing such that urine collected in the collection tube can flow into the discharge tube. In various embodiments, the discharge tube may typically be of 8', 10', or 12' in length to allow connection to a urine collection container. A discharge tube may be of any suitable length, for example, between about 2" and 20' (or more) based on the use of the fluid collection system and the needs of the patient. An example of a vented housing is illustrated and described herein. However, in other embodiments, the vented housing can have other shapes and designs and provide the same function. The vented housing can include one, or a plurality of vents, that allow air to enter the housing. The vents can be of any shape, size, and arrangement that allow air to enter the housing and inhibit or prevent unwanted things (e.g., material, fingers, debris, and the like) from entering the vented housing. The discharge tube may be an integral tube that extends into a portion of the vented housing and is coupled to the baseplate. Alternatively, the discharge tube may include two or more components that are coupled together. For example, a discharge tube may include a first component (e.g., an interconnection device) having a proximal portion that is coupled to the baseplate and a distal portion that extends partially or fully out of the vented housing, and may include a second component (e.g., tubing) that is connected to the distal portion of the first component. The collection tube may extend into a proximal end of the vented housing and be coupled to a baseplate. The baseplate may be disc-shaped, having a curved perimeter edge (or side) such that the perimeter is circular, oval, or curved. The baseplate includes a main aperture through which urine can flow from the collector tube to the discharge tube. The collection tube may be coupled to the side of the baseplate by positioning (inserting) the baseplate inside of the end of the collection tube. The discharge tube may be coupled to a center portion of the baseplate such that urine that flows through the main aperture flows into the discharge tube.

Figure 2:
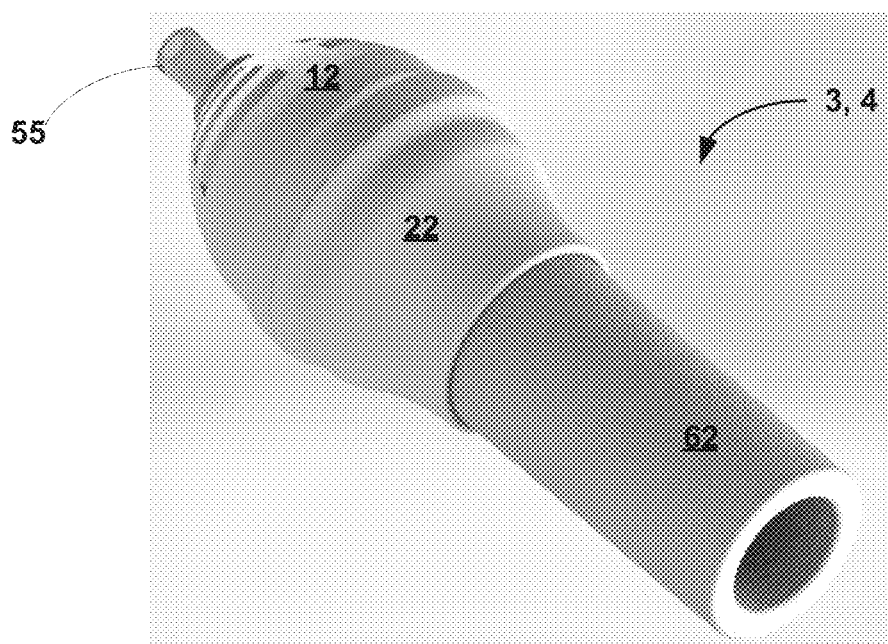
FIG. 2 is a perspective view of the third and fourth embodiment of a fluid collection apparatus illustrated in FIGS. 17 and 21.

The fluid collection apparatus can be embodied in a slim, compact, and aesthetically-pleasing design to facilitate being worn and used in a variety of situation. The compact and aesthetically-pleasing design of the apparatus also can advantageously reduce a patient's stress level of having to use such a device. An example of such a fluid collection apparatus for collecting urine from a male subject is shown in FIG. 2, which illustrates a perspective view of the embodiments of a fluid collection apparatus also illustrated in FIGS. 17 and 21. An example of such a fluid collection apparatus for collecting urine from a female subject is shown in FIG. 1, which illustrates a perspective view of embodiments of a fluid collection apparatus also illustrated in FIGS. 4 and 13. In both of these examples, a vacuum pump connected to the discharge tube can generate lower air pressure (a vacuum) in the collection tube, and this pressure differential causes a suction at a proximal end of the collection tube which helps maintain a seal during the engagement of the collection tube and a patient. Once an adequate seal has been established, the vacuum may be decreased, leaving a low vacuum within the collection tube thereby maintaining the seal. Having a suction present in the collection tube during urination facilitates the flow of urine into the collection apparatus and into the discharge tube, and to a collection vessel/container. In some embodiments, one or more portions of the fluid collection apparatus are made from a transparent or translucent material. This may advantageously allow a medical practitioner or patient to observe that urine is being discharged by the patient, and that the urine is in fact flowing through the fluid collection apparatus to the discharge tube when urine is present in the fluid collection apparatus.

The described embodiments include several specific examples of a fluid collection apparatus. These examples generally include a vented housing that includes a rear housing, a front housing coupled to the rear housing, an elastomeric collection tube that has a distal end extending into the front housing and coupled therein, a urethra tube positioned inside of a proximal portion of the collection tube, and a discharge tube having a proximal end extending into the rear housing and coupled therein. An example of a rear housing and a front housing are described herein. However, in other embodiments, the rear housing and/or the front housing can have other shapes and designs and provide the same function. The urethra tube and collection tube are collectively adapted for joining with the human urethra, either male or female, and as such, enables reception of urine discharges. Urine discharged from a subject is received in the urethra tube, flows through the collection tube into the housing, and then the urine flows out of the housing through the discharge tube. Urine can be collected from a distal end of the discharge tube in a container and subsequently analyzed, if desired. In operation, the discharge tube can be coupled to a vacuum source (e.g., a vacuum pump) and a urine collection system, which may be configured to allow easy disposal of the urine. The urine collection system may include a system to analyze substances in the urine. In an example, for an implementation for collecting urine from a male, a suction of about 9 inches of mercury (Hg) vacuum may be produced with a vacuum source that is coupled to the discharge tube. In another example, for an implementation for collecting urine from a female, a suction of about 15 inches of Hg vacuum may be produced with a vacuum source that is coupled to the discharge tube. In some embodiments, the suction is between 7 and 11 inches of Hg vacuum (e.g., for a male patient). In some embodiments, the suction is between 12 and 18 inches of Hg vacuum (e.g., for a female patient). This suction enables the temporary joining between the interface portion and the urethra, and facilitates the flow of urine from the subject's urethra, through the collection tube/urethra tube, through the housing and into the discharge tube. In various examples, the amount of suction, in inches of Hg vacuum that is applied to the discharge tube, can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 inches of Hg (+/−0.5 inches of Hg vacuum). In some embodiments, the amount of suction is between about 7 and 17 inches of Hg vacuum. Examples of discharge tubes, a collection tube, and urethra tubes are described herein. However, in other embodiments, the discharge tubes, collection tube, and/or urethra tubes are can have other shapes and designs and provide the same function.

The front housing and the rear housing can be releasably coupled together by coupling structure on a proximal portion of the rear housing and corresponding coupling structure on a distal portion of the front housing. In an example, the coupling structure on the rear and front housing is formed along corresponding circumferential edges that are mated together to couple the rear housing to the front housing. In a specific example, a circumferential edge of the front housing fits inside of a portion of a circumferential edge of the rear housing, and a protrusion along the circumferential edge of the front housing fits into a circumferential indentation of the rear housing to releasably lock them together. The coupling structure is shown in detail in FIG. 25A-C (front housing) and FIG. 26A-D (rear housing) is a snap fit. Other types of coupling structures are also possible (e.g., threads, friction fit, bayonet coupling, etc.). In some examples, the front and rear housing are coupled together such that they are not separable, or difficult to separate.

Both the collection tube and the discharge tube are coupled to a baseplate that is positioned inside the vented housing. In some examples, the baseplate is generally disc-shaped includes a main aperture through which the collected urine flows from the distal end of the collection tube to the proximal end of the discharge tube. The baseplate also includes at least one valve aperture that forms an opening from the distal side of the baseplate to the proximal side of baseplate. A one-way valve may be positioned in one or more or each of the apertures. Various embodiments may include, for example, one valve, two valves, three valves or four valves. Each valve allows air to flow from the rear housing, through the valve, and into a portion of the collection tube that is coupled to the baseplate as described below. A portion of the valve can extend through the baseplate and include a projection that helps couple the discharge tube, or a coupling structure connected to the discharge tube, to the proximal side of the baseplate as described below.

The baseplate is sized to fit into the distal end of the collection tube such that the distal end of the collection tube extends around and past the baseplate to a termination point that is inside the vented housing. When the baseplate is operationally connected to the collection tube (e.g., assembled and ready for use) the baseplate is inside of the distal end of the collection tube. In this position, the baseplate is aligned along a cross-sectional plane of the collection tube and a circumferential edge (also referred to herein as the side-surface) of the baseplate contacts an inside surface of the collection tube. The circumferential edge can include several structures that are designed to allow the baseplate to be inserted into the collection tube and engage the inside surface of the collection tube to form a leak-proof and airtight seal diameter between the baseplate and the inside surface of the collection tube. For example, the baseplate can include an angled side surface on a proximal portion of the circumferential edge, the angled side surface angling inward towards the proximal side of the baseplate, that makes it easier to insert the baseplate into the collection tube. The baseplate can also include one or more ridges (e.g., one, two, or more ridges) on the circumferential edge. Advantageously, each ridge, and the angled side surface, may provide structure that forms an interference fit between the circumferential edge of the baseplate and the interior surface of the collection tube. Examples of a baseplate that includes an angled side surface and two ridges are described below, for example, in reference to FIGS. 10, 12, 27, and 28. Several examples of baseplates are described herein. However, in other embodiments, a baseplate can have other shapes and designs and provide the same function.

The angled side surface and each ridge also advantageously allow the collection tube to be coupled to the baseplate easily and quickly. Some collection systems require a cumbersome and time-consuming process of pulling the collection tube around the baseplate and then securing the portion of the collection tube that extends past baseplate to a structure on the distal portion of the baseplate to seal and couple the collection tube to the baseplate. For a collection apparatus that includes the baseplate described herein, the baseplate can simply be inserted into the distal end of collection tube to couple the collection tube to the baseplate, and the edge of the baseplate seals the collection tube. In addition, the baseplate and the front housing are designed to couple the collection tube between a portion of the inside surface of the front housing in the baseplate. The diameter of the baseplate is designed to be larger than the diameter of the proximal aperture of the front housing, which is the aperture that the collection tube passes through as it extends into the front housing. This is illustrated, for example, in FIGS. 7 and 8. Accordingly, when the baseplate is properly positioned inside of the distal end of the collection tube (e.g., aligned along a cross-sectional plane of the collection tube), the diameter of the collection tube is deformed (expanded) to accommodate the baseplate. This collection tube/baseplate assembly is too large to fit through the proximal aperture of the front housing. Because the front housing narrows from its distal end to its proximal, the collection tube is held between the baseplate circumferential and a circumferential interior surface of a narrowed portion of the front housing, and in this way the collection tube is coupled to the baseplate (and to the vented housing).

In embodiments illustrated herein, the discharge tube extends through an aperture at the distal end of the rear housing and is coupled to the baseplate. The aperture at the distal end of the rear housing can have a grommet positioned therein, and in such embodiments discharge tube also extends through the grommet. In some embodiments, the grommet can be sized to fit tightly around the discharge tube such that the grommet at least partially couples the discharge tube to the rear housing. The grommet also protects the discharge tube from being damaged/cut through contact with the housing. In some embodiments, the proximal end of the discharge tube includes a sleeve, or another coupling structure, that may help to couple the discharge tube to the baseplate. Such coupling structure can be formed as part of the discharge tube, or be coupled to the discharge tube. For ease of reference here, a sleeve or another coupling structure that is connected to the proximal end of the discharge tube will be considered to be the proximal end of the discharge tube, unless otherwise described. The proximal end of the discharge tube can extend through at least a portion of the main aperture of the baseplate, from the distal side to the proximal side, and be coupled to the baseplate. In various embodiments described herein, the proximal end of the discharge tube is coupled to the baseplate using at least one O-ring (e.g., one or two O-rings). For example, the O-ring(s) can be positioned around the proximal end of the discharge tube that extends through the baseplate.

Components of the fluid collection apparatus may be assembled into a ready to use fluid collection apparatus and provided in a sterilized sealed container (e.g., a pouch). In one example of assembling a fluid collection apparatus, the discharge tube may be coupled to the baseplate. The discharge tube may be inserted into the distal side of the baseplate such that the proximal end of the discharge tube extends through the baseplate. One or more O-rings (or other fasteners) can couple the proximal end of the discharge tube on the proximal side of the baseplate. The valves for a particular embodiment may be mounted into the baseplate, the proximal end of each valve extending through the baseplate. In an example for a male fluid collection apparatus, for valves are mounted into baseplate. In an example for a female fluid collection apparatus, two valves are mounted into the baseplate. The proximal end of each valve may be positioned to be in contact with the one or more O-rings to help couple the proximal end of the discharge tube to the baseplate. The distal end of the discharge tube can be passed through the distal end of the rear housing and through a grommet, the grommet positioned into a circular aperture at the distal end of the rear housing. The distal end of a collection tube may be inserted into the proximal end of a front housing. The baseplate may be inserted, the or placed into contact with, the distal end of the collection tube such that the baseplate seals the distal end of the collection tube. In some examples, the distal end of the collection tube is positioned to extend past the baseplate such that the baseplate is positioned inside of the distal end of the collection tube. The rear housing in the front housing may then be coupled together using a snap fit coupling structure that does not require any additional sealant or adhesive. The urethra tube, for a male or female patient, may be inserted into the proximal end of the collection tube. A urethra tube for a male patient may be inserted into the collection tube such that is positioned near the front housing. The urethra tube for a female patient may be inserted into the collection tube such that the proximal end of the urethra tube is just inside the proximal end of the collection tube. The fluid collection apparatus may be sealed in a pouch and sterilized, such that it can be stored and is ready for use at any time.

In some embodiments, one or more sensors may be positioned in the fluid collection apparatus (e.g., in the collection tube on the proximal side of the baseplate). The one or more sensors can include one or more of a moisture sensor, a blood sensor, a sodium chloride sensor, a protein sensor, and/or a calcium sensor. Other types of sensors can also be included. The sensor can be a wired sensor or a wireless sensor. In an example, a sensor can be electrically coupled to a wire that extends out of the vented housing, for example, a wire the runs along or is incorporated into the discharge tube. In another example, a wireless sensor may be configured to communicate with a receiver of a computing device, for example, using Bluetooth or another wireless protocol. The sensor may communicate with a computing device, the computing device receiving the signal from the sensor. The computing device may be configured to store the signal, determine if the signals indicative of a substance or material, and/or provide a user display that shows information relating to the signal. Having a sensor(s) positioned in the fluid collection apparatus can advantageously provide early information relating to material or substances that are in a patient's urine, such that appropriate actions may be quickly taken if a certain material or substance is discovered.

In some embodiments, a liquid/moisture sensor creates a signal when fluid is sensed in the collection tube, and the signal is communicated to a controller of a vacuum pump. The controller may operate the vacuum pump to produce a higher suction level within the collection tube when fluid is present, drawing the urine into the fluid collection apparatus, through the discharge tube and into a collection vessel. When the sensor no longer senses the presence of liquid, the sensor no longer produces the signal, or produces a diminished signal, and the controller may operate the vacuum pump to stop, or to enter a standby mode to provide a low-level suction for maintaining a connection of the urine tube to the urethra.

Urine received in the container can be analyzed by sensors in the vessel, or other sensors, to detect substances within the urine. For instance, using known sensors and analytic techniques: Quantitative analysis of occult blood, proteins, glucose, drugs, and various chemical compositions can be determined. This information is delivered to a digital processor for data logging and analysis including plotting values against time. Comparison of measured values relative to standards enables prediction of medical conditions including illness. Embodiments described herein can provide one or more of several advantageous objectives. One objective is the easy assembling of the fluid collection apparatus. Another objective is the easy configuration of the apparatus to be used for a male or female subject. Another objective is to provide a simpler and lower cost fluid collection apparatus. Another objective is to maintain a tube at a urethra outlet. Another objective is to provide a means for allowing urination to occur without interrupting a person's sleep or activities. It is another objective to continuously monitor a subject's biological signs through urine sampling and analysis. It is another objective to collect urine in a system that is low cost, easily-operated, and portable to be useful by paramedics in the field.

Several illustrative embodiments of an apparatus for collecting fluid are described herein. Some of the figures include dimensions of features of the apparatus, the tolerances of the dimensions (unless otherwise indicated) may be: for decimals: 0.xx+/−0.01", 0.xxx+/−0.005"; fractions: 1/64"; and angles: +/−1°. The following is a list of certain components that are described and enumerated in this disclosure in reference to the above-listed figures. Other components, or aspects of these components, may not be included in the list but are disclosed in the figures and description. Accordingly, any aspect illustrated in the figures, whether or not called out separately herein, can form a portion of various embodiments and may provide basis for claim limitation relating to such aspects, with or without additional description. The enumerated components include:

| | |
|---|---|
| 1 fluid collection apparatus | 18 coupling rear housing |
| 2 fluid collection apparatus | 19 coupling front housing |
| 3 fluid collection apparatus | 20 $2^{nd}$ aperture rear housing |
| 4 fluid collection apparatus | 21 exterior surface rear housing |
| 5 distal side/end | 22 front housing |
| 6 proximal side/end | 23 proximal end front housing |
| 7 longitudinal axis of apparatus | 24 distal end front housing |
| 8 area | 25 outer edge (proximal end) front housing |
| 9 longitudinal axis | 26 outer edge (distal end) front housing |
| 10 vented housing | 27 $1^{st}$ aperture proximal end front housing |
| 12 rear housing | 28 $2^{nd}$ aperture distal end front housing |
| 13 proximal end rear housing | 30 grommet |
| 14 distal end rear housing | 32 baseplate distal surface |
| 15 vent(s) | 33 baseplate proximal surface |
| 16 $1^{st}$ aperture rear housing | 34 baseplate proximal edge |
| 17 outer edge rear housing | 35 interior surface edge wall |
| 36 extended edge wall | 70 urethra interface (urethra tube) |
| 37 distal portion of edge wall | 71 distal end urethra interface |
| 38 proximal portion of edge wall | 72 proximal end urethra tube |
| 39 circumferential concavity | 73 flared portion urethra tube |
| 40 baseplate | 74 $1^{st}$ diameter |
| 41 proximal side of baseplate | 75 $2^{nd}$ diameter |
| 42 distal side of baseplate | 76 angle |
| 44 side surface | 77 exterior surface collection tube |
| 45 circumferential ridge(s) | 78 interior surface collection tube |
| 46 valve(s) | 79 flared portion |
| 47 main aperture | 80 garment |
| 48 valve aperture | 81 interface |
| 49 protrusion | 82 wire |
| 50 O-ring(s) | 83 processing system |
| 51 valve first end (proximal end) | 84 display |
| 52 valve second end (distal end) | 85 mobile device |
| 53 projection | 86 system |
| 54 sensor | 102 bus |
| 55 interconnection tube (discharge tube) | 104 processor(s) |
| 56 distal end discharge tube | 106 main memory |
| 57 proximal end discharge tube | 108 ROM |
| 58 coupler | 110 storage device |
| 59 sleeve | 114 input device |
| 60 ring | 116 cursor control |
| 62 fluid (or collection) tube | 120 network link |
| 63 distal end collection tube | 122 local network |
| 64 proximal end collection tube | 124 host(s) |
| 65 termination point | 126 ISP |
| 66 stretched fluid tube | 128 Internet |
| 67 inside housing contact surface | 130 server(s) |
| 68 collection tube cavity | |

Figure 3:
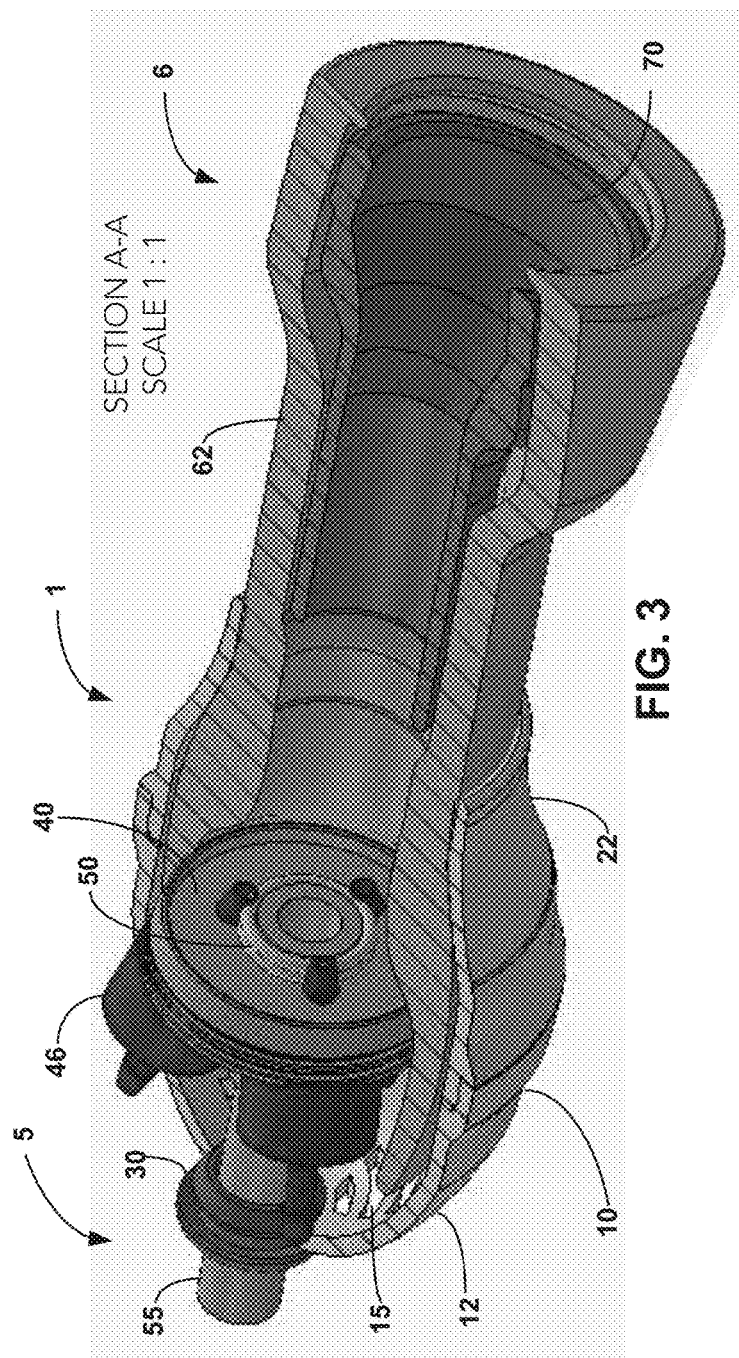
FIG. 3 is a perspective partial cross-sectional view along line A-A of FIG. 4 illustrating certain components and structure of the fluid collection apparatus shown in FIG. 4.
Figure 4:
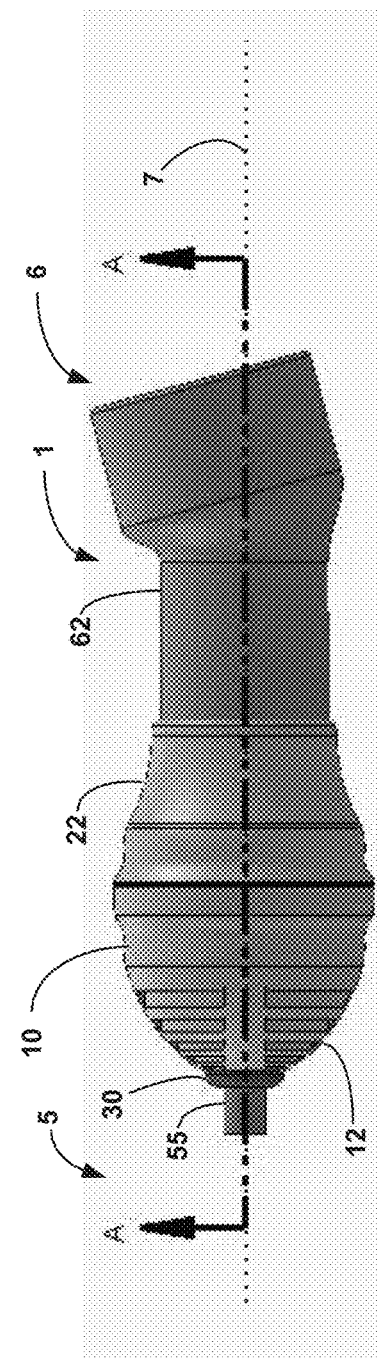
FIG. 4 is a side view of a picture of a first embodiment of a fluid collection apparatus configured to collect fluid from a female patient.
Figure 25A:
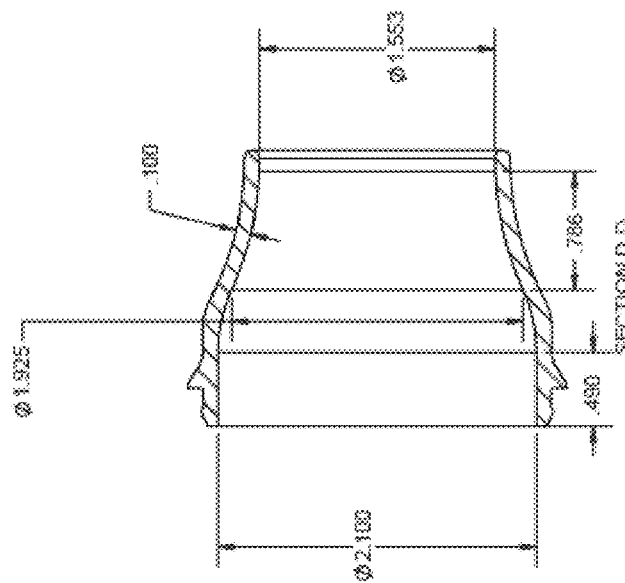
FIG. 25A illustrates a set of schematics of an example front housing.
Figure 25A:
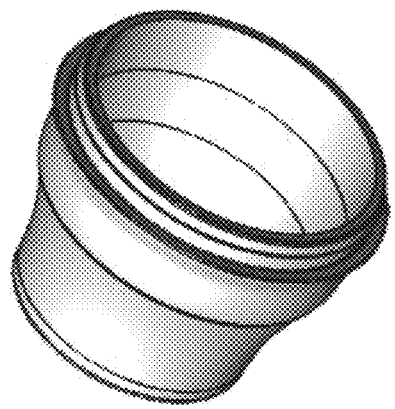
Figure 25A:
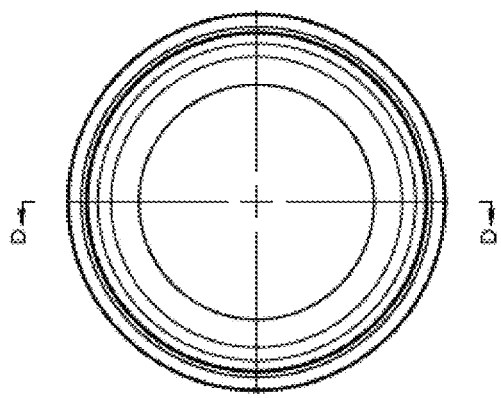
Figure 25A:
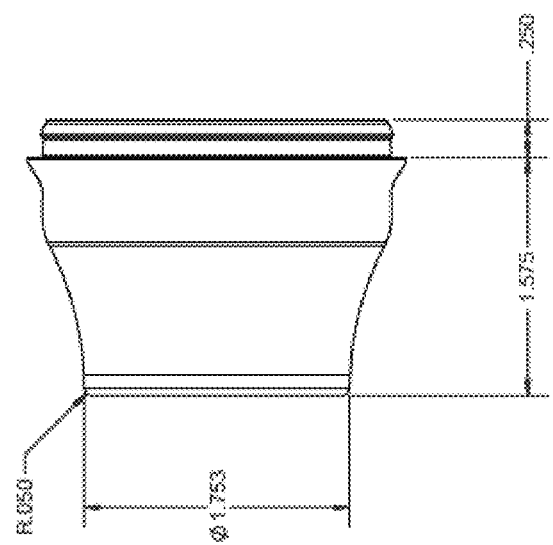
Figure 25B:
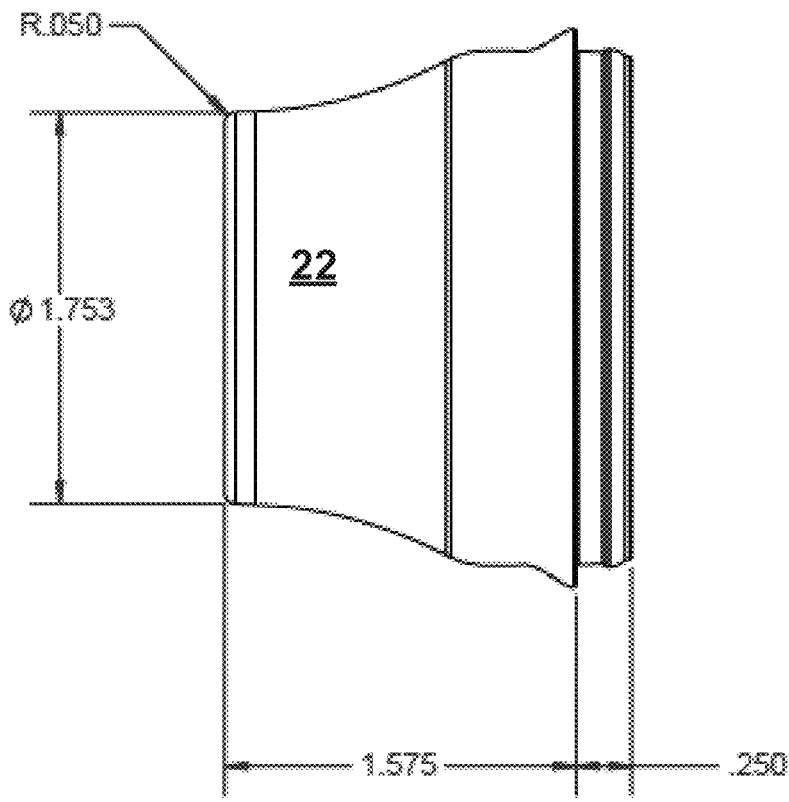
FIG. 25B illustrates a side view of the front housing illustrated in FIG. 25A, and shows dimensions (in inches) of certain features of the front housing.
Figure 25C:
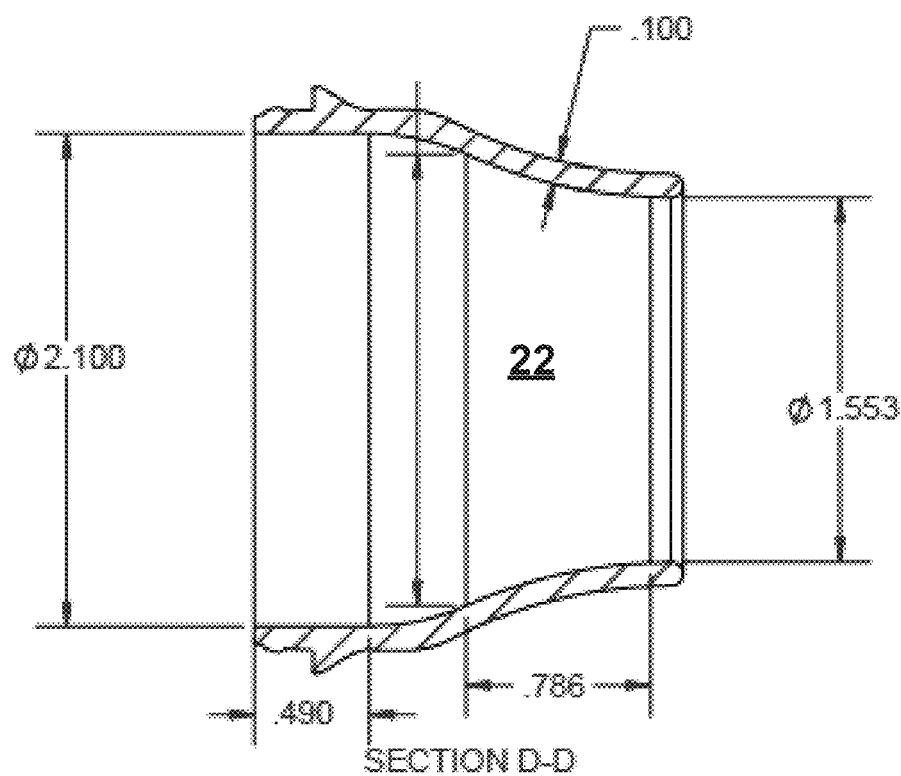
FIG. 25C illustrates a cross-sectional view of the front housing illustrated in FIG. 25A along line D-D, and shows dimensions (in inches) of certain features of the front housing.
Figure 26A:
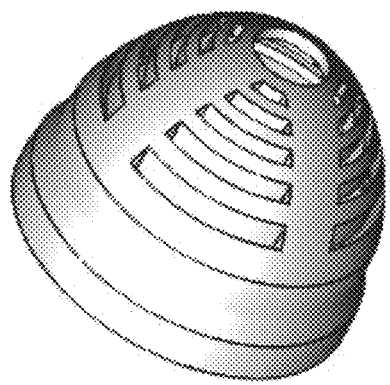
FIG. 26A illustrates a set of schematics of an example rear housing 12.
Figure 26A:
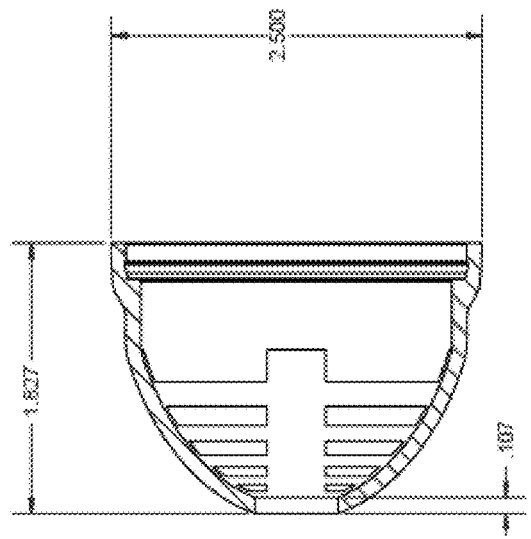
Figure 26A:
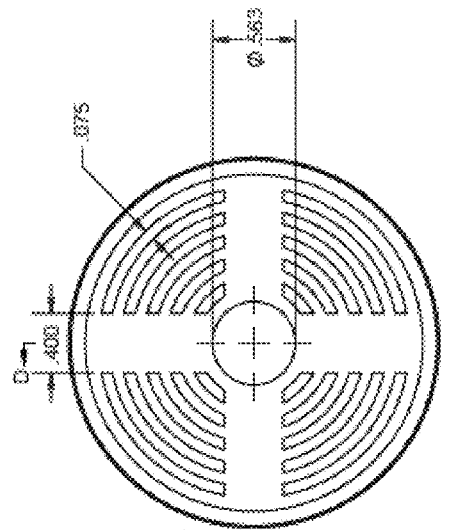
Figure 26B:
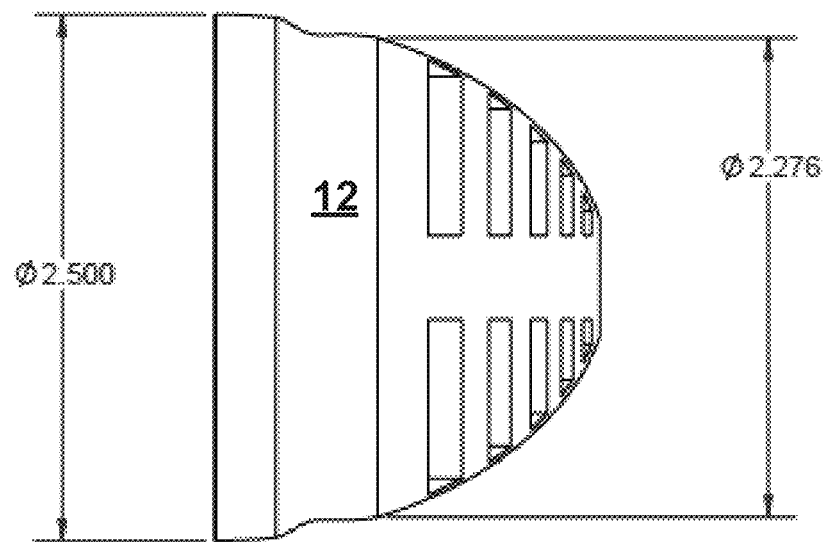
FIG. 26B illustrates a side view of the rear housing illustrated in FIG. 26A, and shows dimensions (in inches) of certain features of the front housing.
Figure 26C:
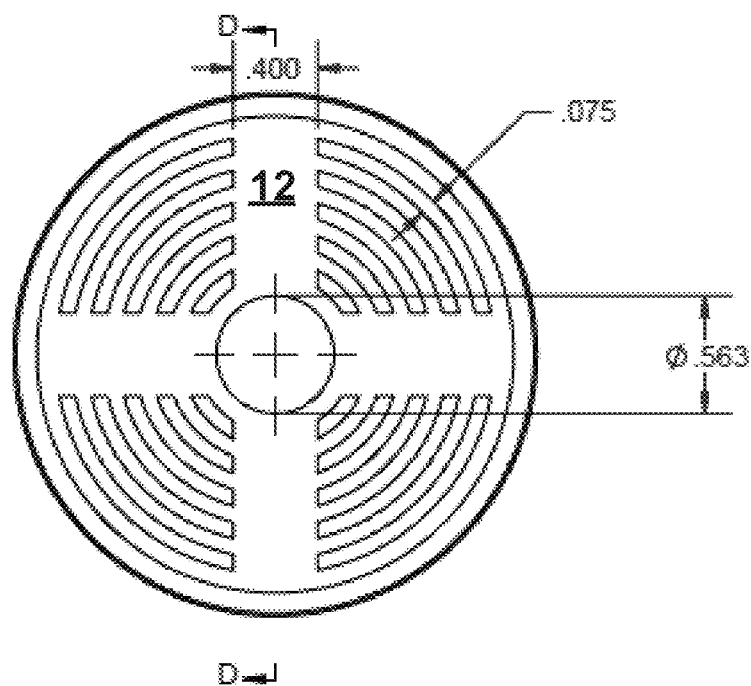
FIG. 26C illustrates a top plan view of the rear housing illustrated in FIG. 26A, and shows dimensions (in inches) of certain features of the rear housing.
Figure 26D:
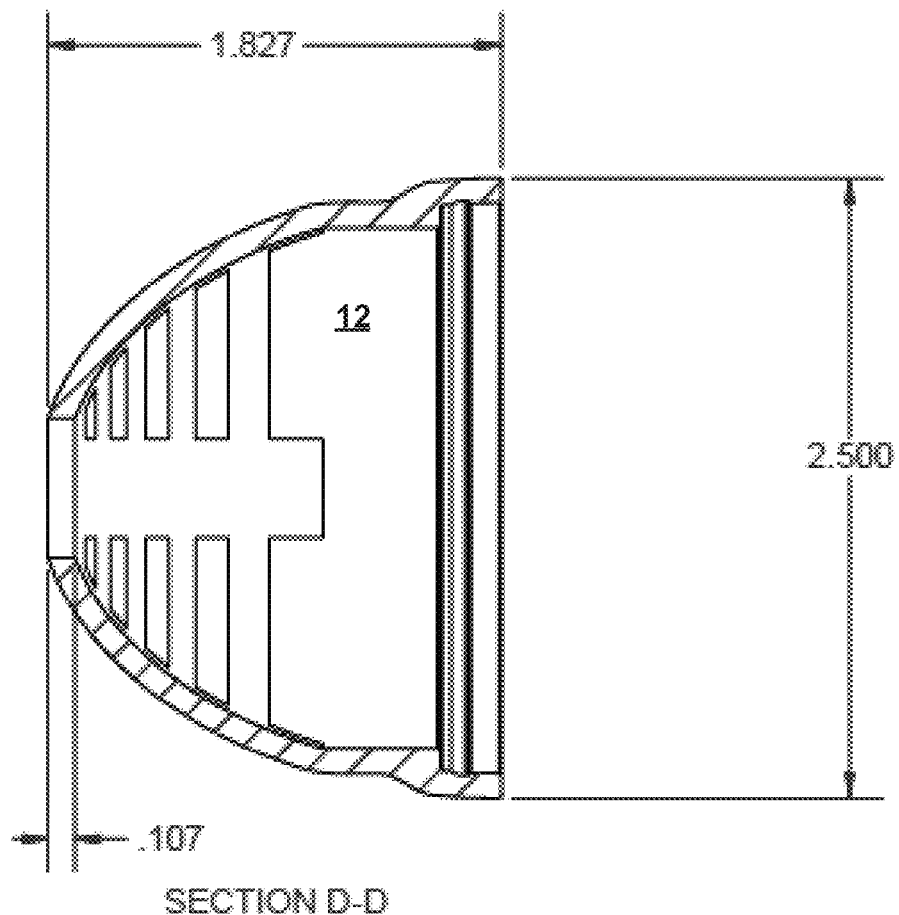
FIG. 26D illustrates a cross-sectional view of the rear housing illustrated in FIG. 26A along line D-D, and shows dimensions (in inches) of certain features of the rear housing.
Figure 27A:
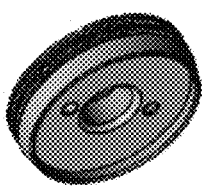
FIG. 27A illustrates a set of schematics of an example baseplate, according to some embodiments.
Figure 27A:
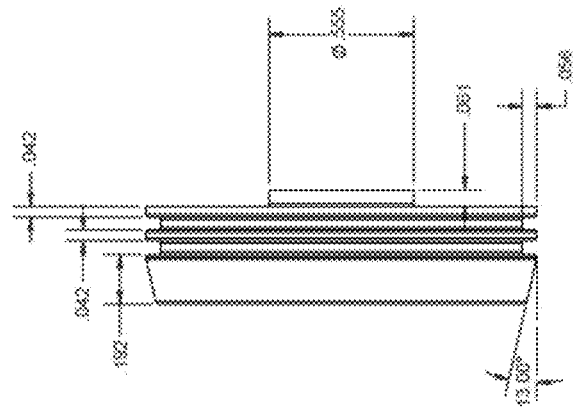
Figure 27A:
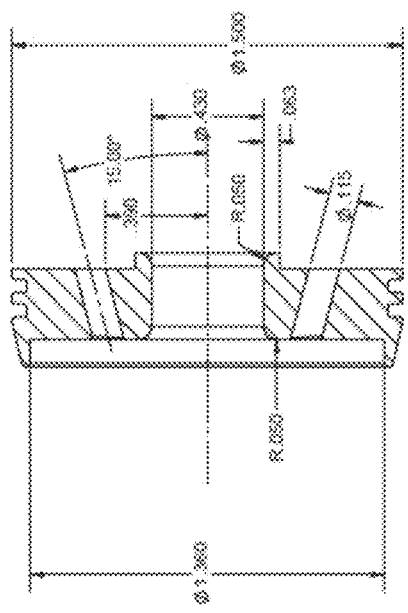
Figure 27A:
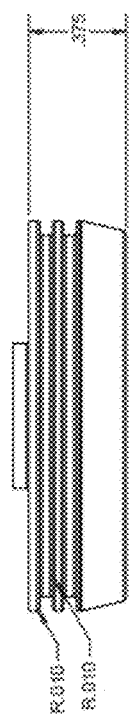
Figure 27A:
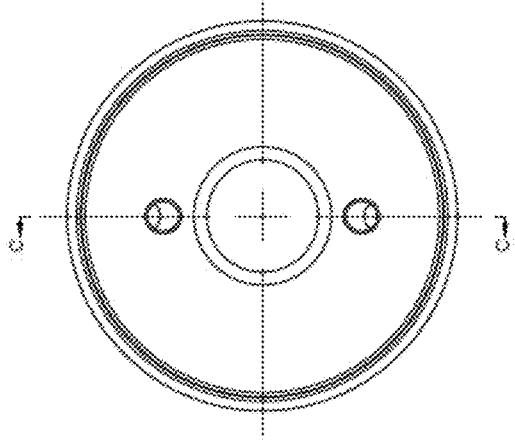
Figure 27B:
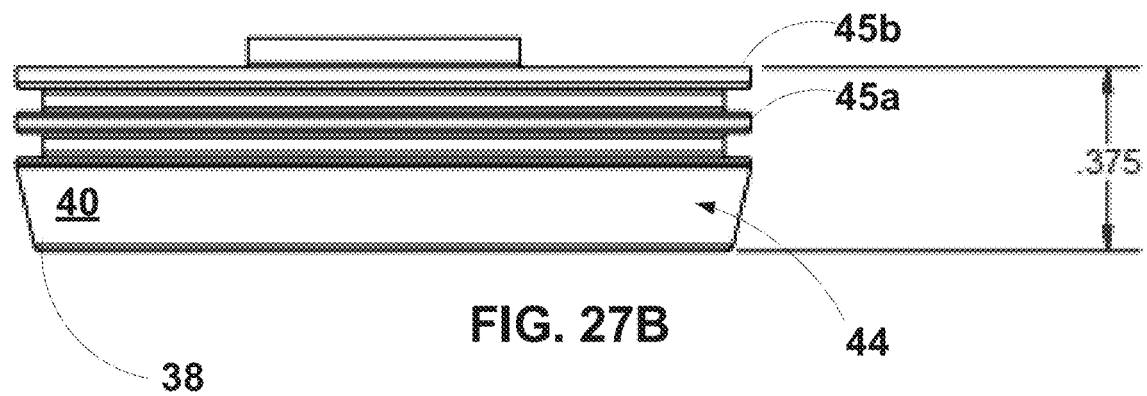
FIG. 27B illustrates a side view of the baseplate illustrated in FIG. 27A, and shows dimensions (in inches) of certain features of the baseplate.
Figure 27C:
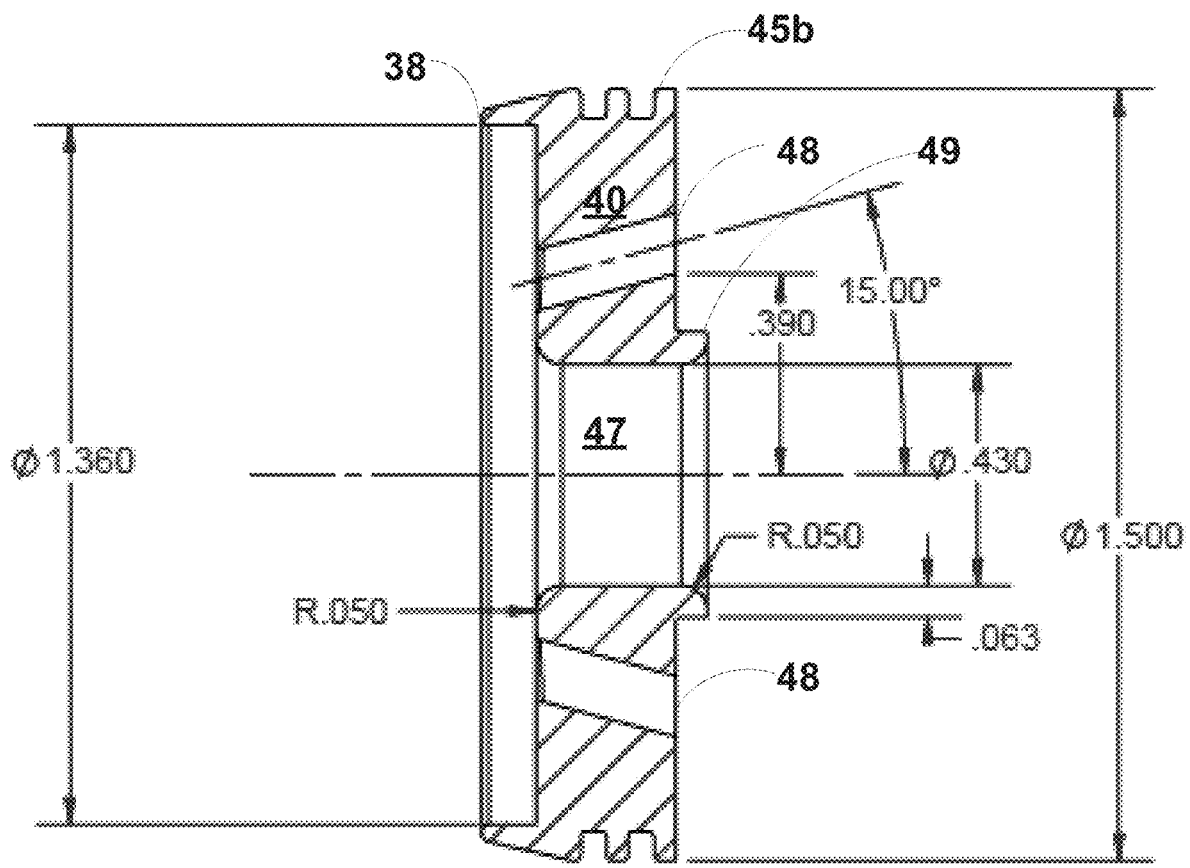
FIG. 27C illustrates a cross-sectional view of the baseplate illustrated in FIG. 27A along line C-C, and shows dimensions (in inches) of certain features of the baseplate.
Figure 27D:
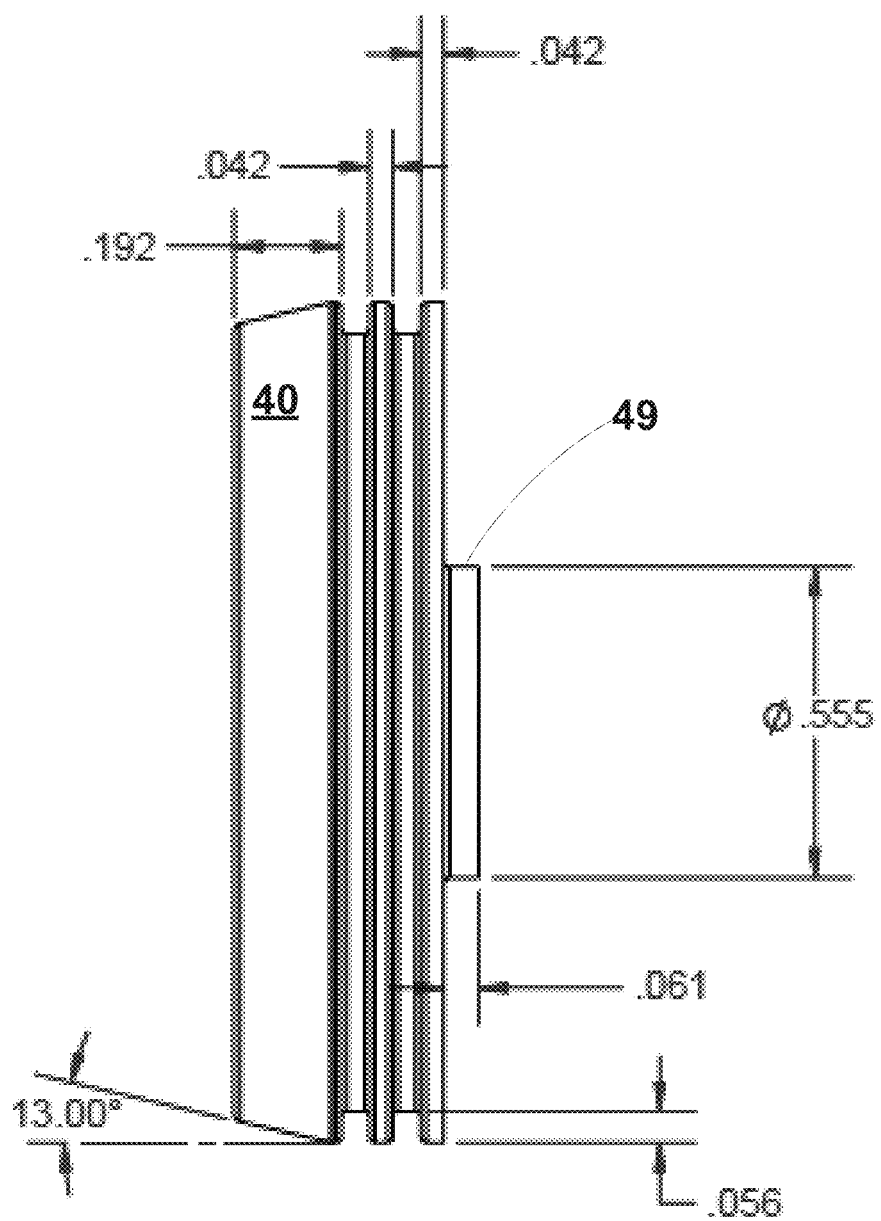
FIG. 27D illustrates a side view of the baseplate illustrated in FIG. 27A, and shows dimensions (in inches) of certain features of the baseplate.
Figure 28A:
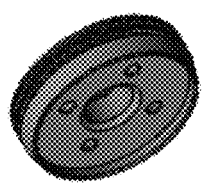
FIG. 28A illustrates a set of schematics of an example baseplate, according to some embodiments.
Figure 28A:
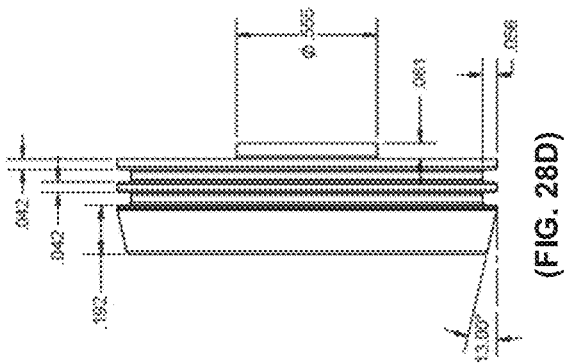
Figure 28A:
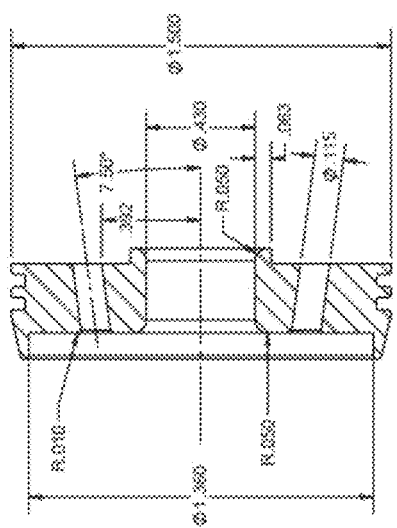
Figure 28A:
Figure 28A:
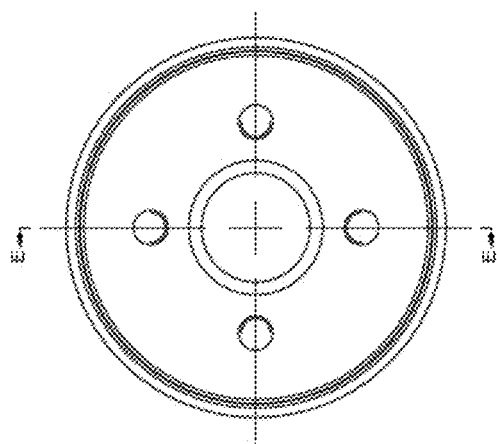
Figure 28B:
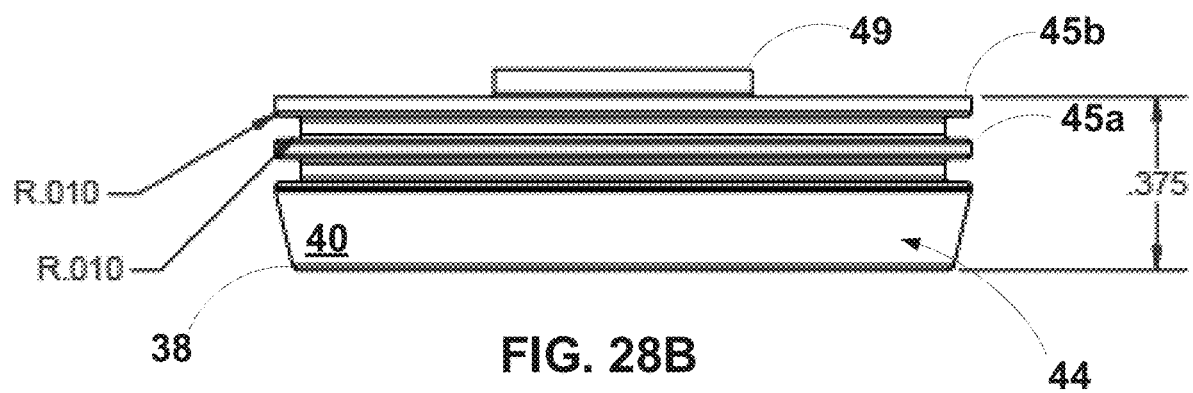
FIG. 28B illustrates a side view of the baseplate illustrated in FIG. 28A, and shows dimensions (in inches) of certain features of the baseplate.
Figure 28C:
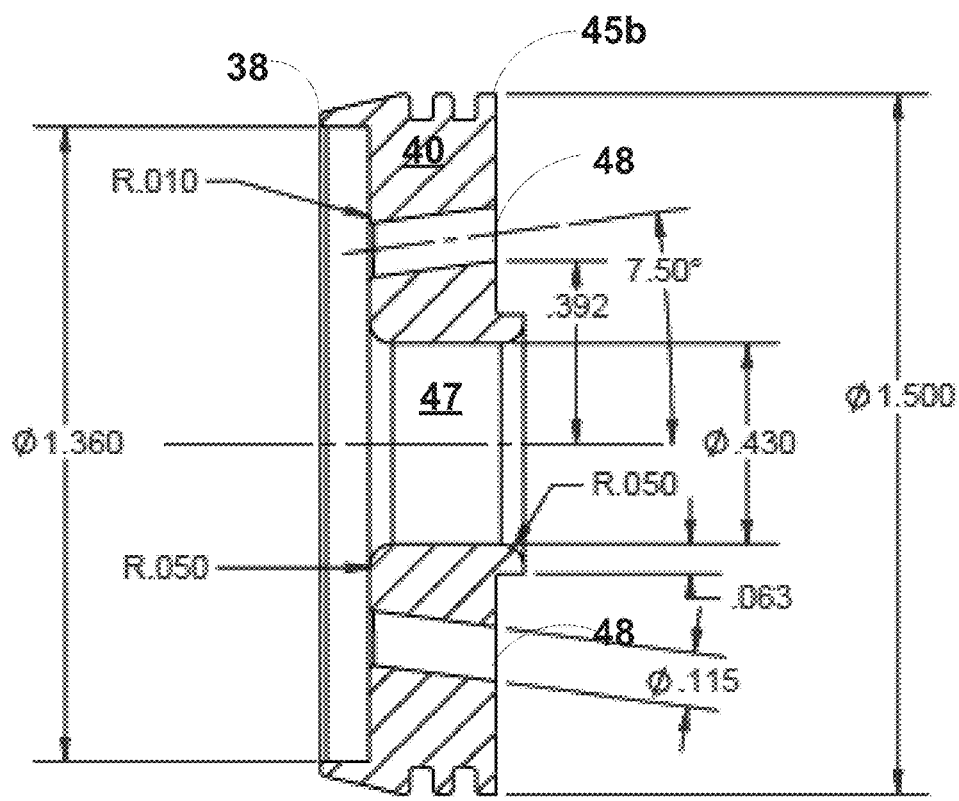
FIG. 28C illustrates a cross-sectional view of the baseplate illustrated in FIG. 28A along line E-E, and shows dimensions (in inches) of certain features of the baseplate.
Figure 28D:
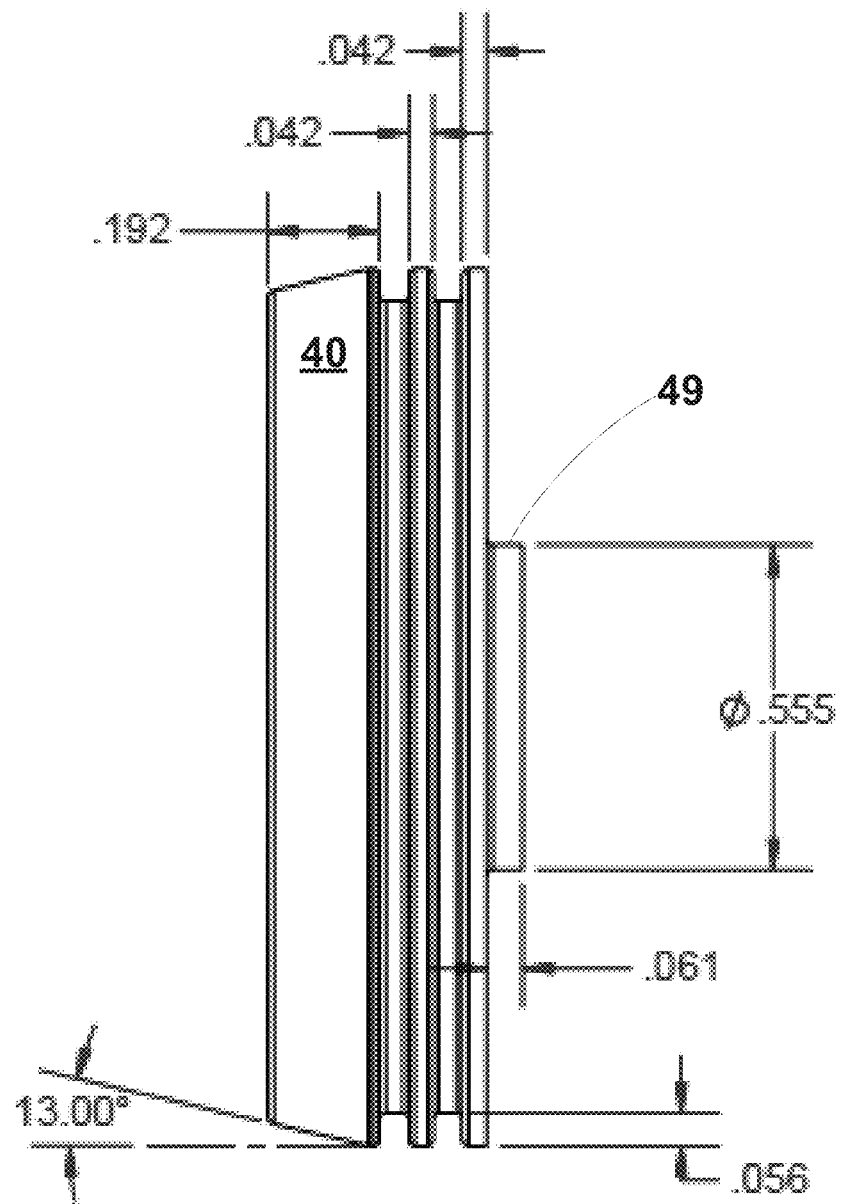
FIG. 28D illustrates another side view of the baseplate illustrated in FIG. 28A, and shows dimensions (in inches) of certain features of the baseplate.

FIG. 4 is a side view of a picture of a first embodiment of a fluid collection apparatus 1 configured to collect urine from a female subject. FIG. 3 is a perspective partial cross-sectional view along line A-A of FIG. 4 illustrating certain components and structure of the fluid collection apparatus 1 shown in FIG. 4. As illustrated in FIGS. 3 and 4, the fluid collection apparatus 1 includes a vented housing 10 having a front housing 22 and a rear housing 12. A distal portion of the front housing 22 and a proximal portion of the rear housing 12 may be coupled together to form an integral vented housing 10. The rear housing 12 may have a curved surface and include one or more vents (holes) 15 that allow air to flow from outside of the rear housing 12 to a cavity inside of the rear housing 12. Various configurations of the rear housing 12 can have differently-shaped curved exterior surfaces, and the vents 15 can be also have various shapes in various configurations. FIG. 25A-C illustrate additional views and certain dimensions of an example of a rear housing 12. The front housing 2 may have a curved surface, and may have a smaller diameter at a proximal portion where the collection tube 62 enters the front housing 22 and a larger diameter where the front housing 22 is coupled to the rear housing 12. Various configurations of the front housing 22 can have differently-shaped curved surfaces. FIG. 26A-D illustrate additional views and certain dimensions of an example of a front housing 22.

Figure 32B:
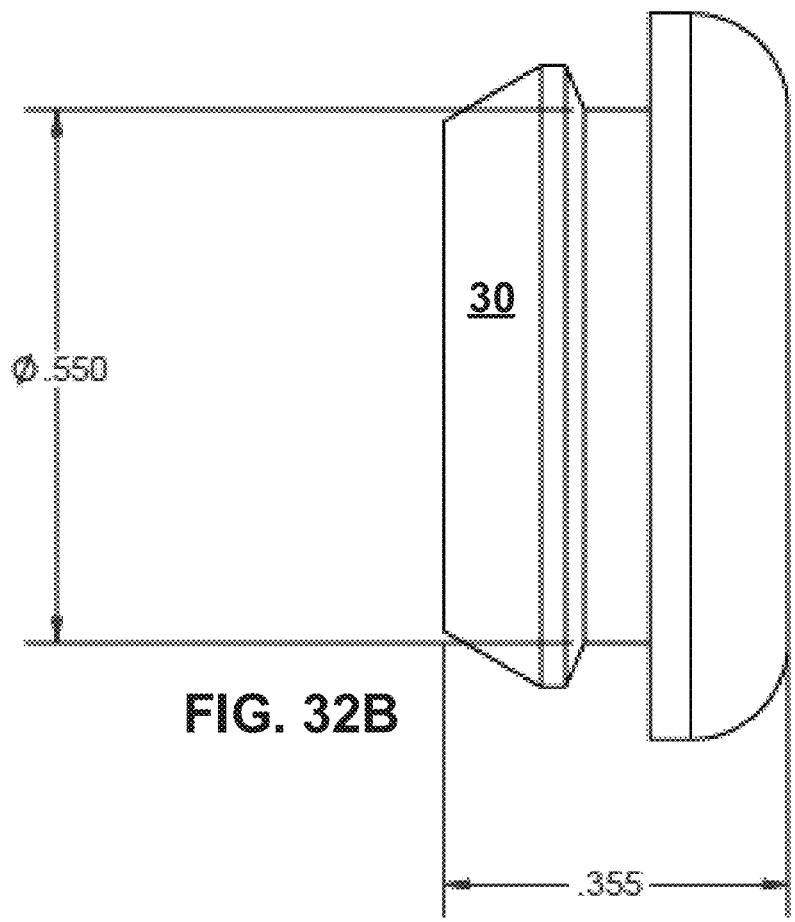
FIG. 32B illustrates a side view of the grommet 30 illustrated in FIG. 32A, and shows certain dimensions (in inches) of the grommet.
Figure 32C:
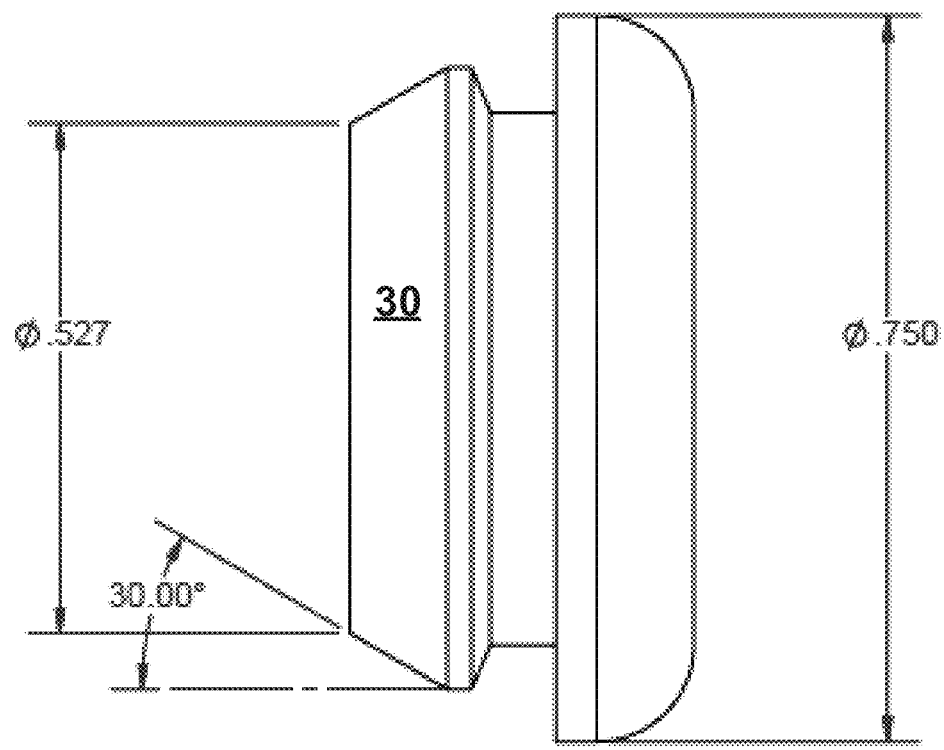
FIG. 32C illustrates a side view of the grommet 30 illustrated in FIG. 32A, and shows certain dimensions (in inches) of the grommet.
Figure 32D:
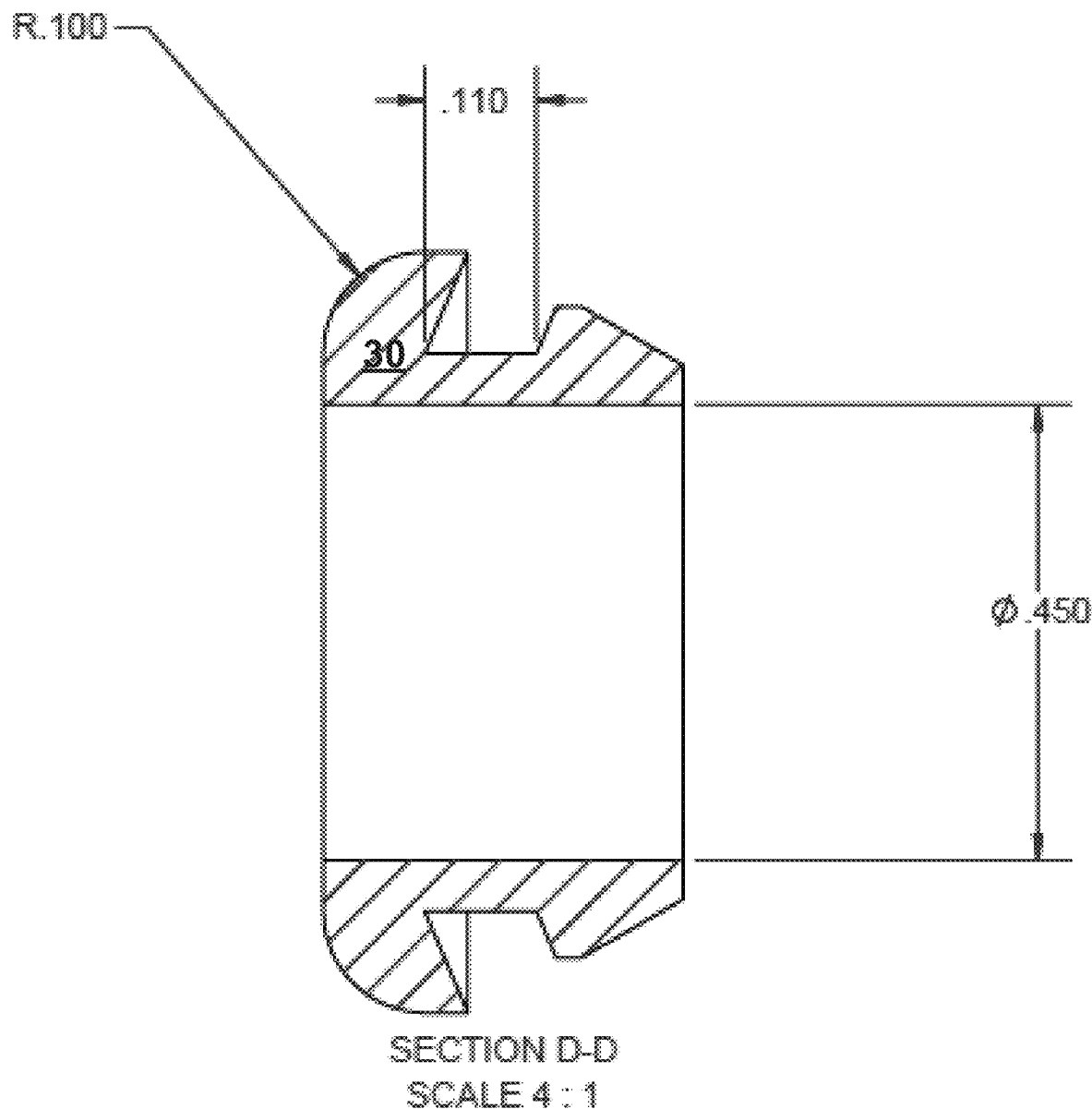
FIG. 32D illustrates a cross-sectional view of the grommet 30, illustrated in FIG. 32A along line D-D, and shows certain dimensions (in inches) of the grommet.

The fluid collection apparatus 1 also includes a discharge tube 55 (or interconnection tube) that has a distal end that extends for a length outside of the venter housing 10, and a proximal end that extends through a grommet 30, into the interior of the vented housing 10, and is coupled to a baseplate 40. The grommet 30 is positioned in an aperture at the distal end of the vented housing 10. FIG. 32A-C illustrate additional views and certain dimensions of an example grommet 30. Various embodiments of a discharge tube 55 are contemplated. In an example, a discharge tube 55 includes a length of tubing that has a distal end that can be coupled to a container or other receptacle, and a proximal end that is coupled to the baseplate 40. The discharge tube 55 may include coupling structure that is attached to the proximal end, or formed as part of the proximal end. For example, the such coupling structure may be a coupler 58 that includes a sleeve 59 and a circumferential ring (or protrusion) 60 which may limit how fare the proximal end of the discharge tube 55 can extend through the baseplate 40. The coupler 58 may be either attached to the proximal end of the discharge tube 55, or it may be formed as part of the proximal end of the discharge tube 55. That is, the discharge tube 55 may include an interconnection device that attaches to the baseplate 40 and extends out of the rear housing 12, and tubing that is attached to the interconnection device.

The baseplate 40 may be disc-shaped and positioned to be aligned in a plane normal to a longitudinal axis 7 (FIG. 4) of the fluid collection apparatus. The discharge tube 55 may be coupled to the baseplate 40 in various ways, e.g., to a portion of either side, or both sides, of the baseplate 40. The illustrated discharge tube 55 extends through an aperture 47 (FIG. 11) in the center of the baseplate 40 and is mechanically held in place (at least partially) by one or more O-rings 50, which are placed around and coupled to the proximal end of the discharge tube 55 on the proximal side of the baseplate 40.

Valves 46 are positioned in the housing 10 extend through the baseplate 40. The valves 46 can include one or more one-way valves that allow air to flow from the interior of the rear housing 12 through the baseplate 40 to the opposite side of the baseplate 40, which is positioned inside of a collection tube 62. Thus, the valves 46 may provide air flow into the collection tube 62, but may inhibit or prevent fluid from passing outward into the housing 10. Valves 46 are configured to allow air to enter the collection tube 62 (e.g., when the pressure differential between the air pressure in the rear housing 10 and the air pressure in the collection tube is above a certain level) such that suction is maintained in the collection tube within a desired range. In an example, such a negative pressure (compared to ambient pressure) of about 3 to 18 inches of Hg is maintained in the collection tube.

The valves 46 extend through the valve apertures 48 that extend between a distal side and a proximal side of the baseplate 40. In an example, the valve apertures 48 may be aligned to form pathways that go straight through the baseplate 40 and may be aligned normal (or nearly normal) to a plane in which the baseplate 40 is aligned (see e.g., FIG. 21). In the illustrated embodiment, the valve apertures 48 are aligned to form openings in the baseplate 40 that are at a non-normal angle to the plane in which the baseplate 40 is aligned. As further illustrated in FIG. 11, the three valves 46 extend through valve apertures 48 that are angled inward (when going from the distal side of the baseplate 40 to the proximal side of the baseplate 40) such that the openings of the valve apertures 48 on the proximal side of the baseplate 40 are closer to the center of the baseplate 40 than the openings of the valve apertures 48 on the distal side of the baseplate 40.

Examples of three different baseplates are illustrated in FIGS. 27A-D, FIGS. 28A-D, and FIGS. 29A-D. Other embodiments of baseplates can also be used in such fluid collection apparatus.

Figure 12:
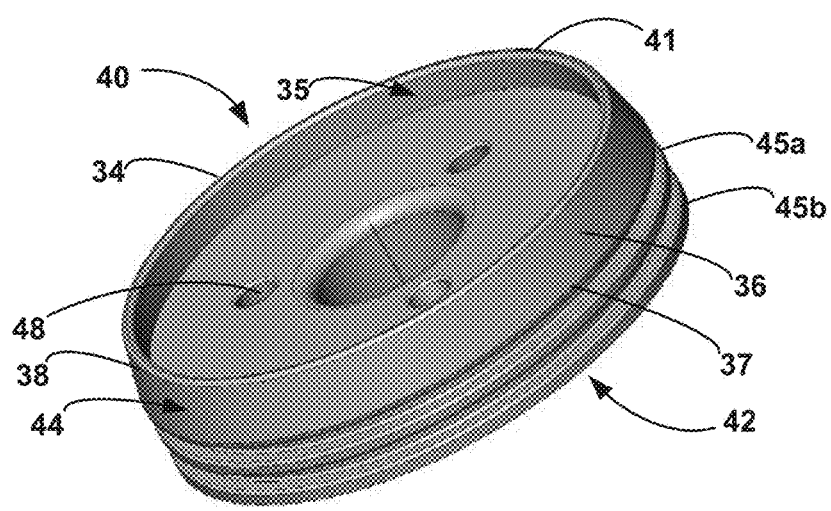
FIG. 12 is a perspective view of the baseplate shown in FIG. 10.
Figure 13:
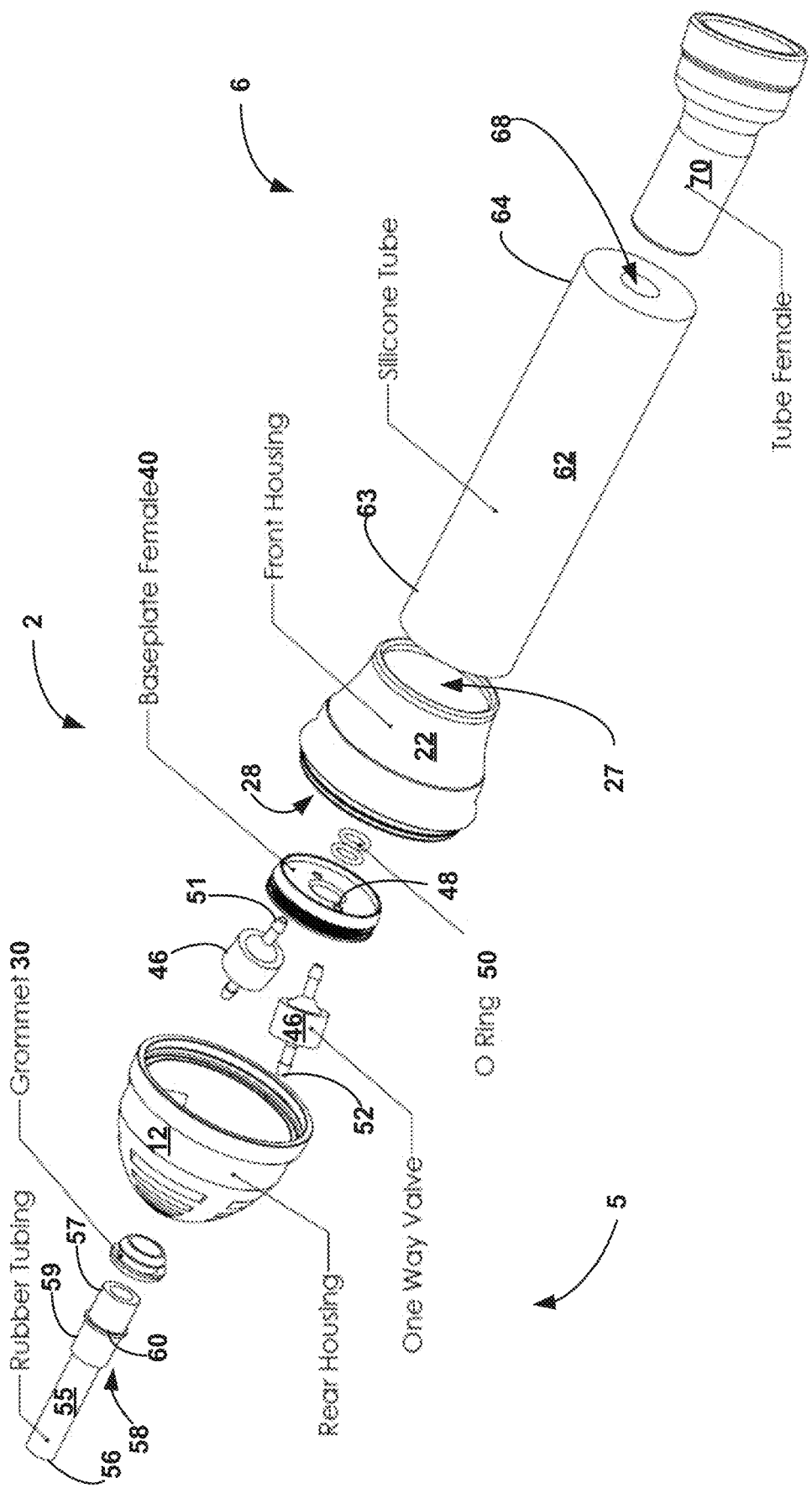
FIG. 13 is an exploded view illustrating certain components of a second embodiment of a fluid collection apparatus adapted to collect urine from a female urethra, this embodiment including two one-way valves positioned in the rear housing and coupled to the baseplate, the valves aligned such that a longitudinal axis of the valves is at an angle relative to a longitudinal axis of the collection device.
Figure 21:
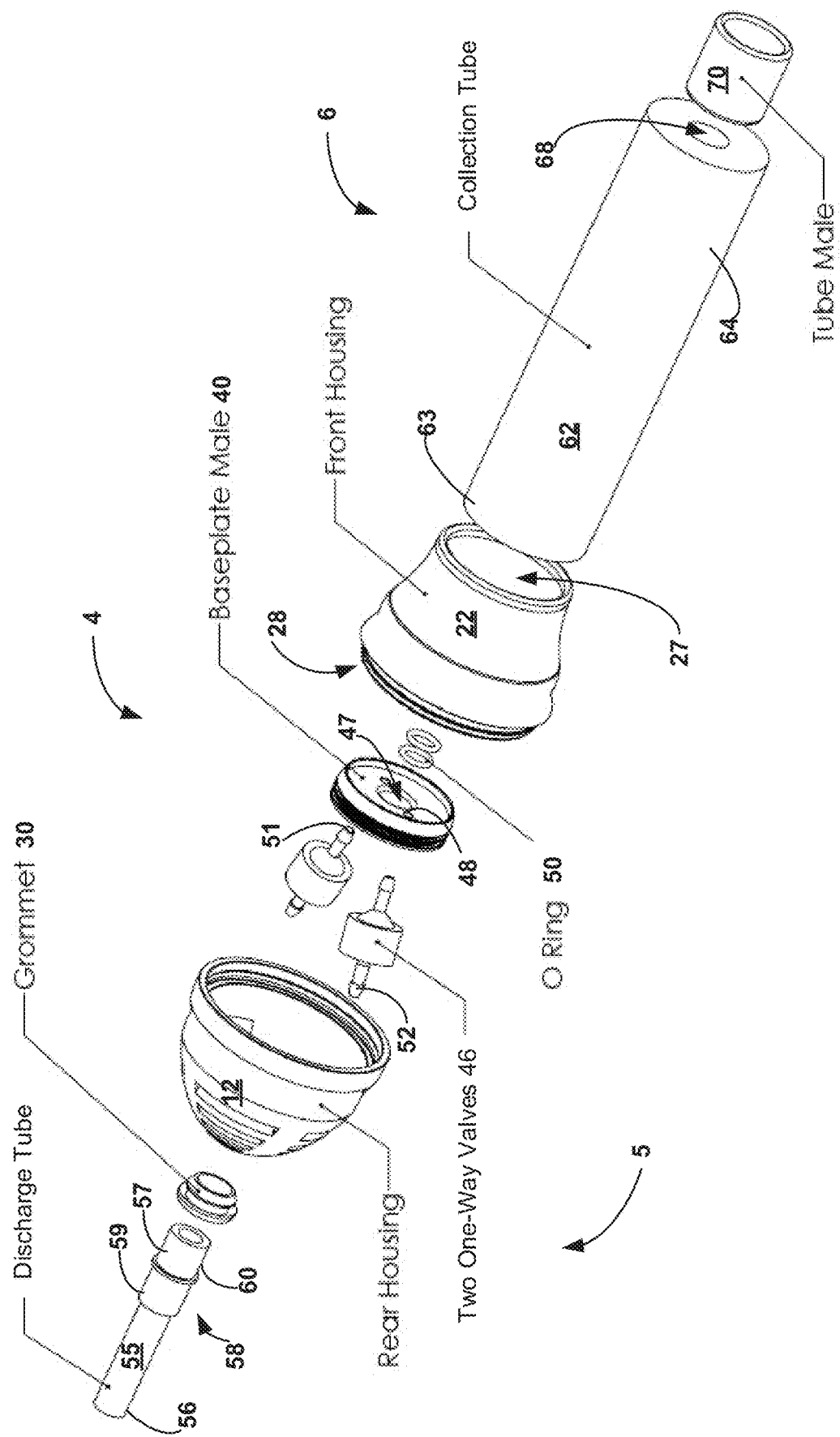
FIG. 21 is an exploded view illustrating certain components of a fourth embodiment of a fluid collection apparatus adapted to collect urine from a male urethra, this embodiment including two one-way valves positioned in the rear housing and coupled to the baseplate, the valves aligned such that a longitudinal axis of the valves is at an angle relative to a longitudinal axis of the collection device.

FIG. 27A-D illustrates schematics and certain dimensions of an example baseplate 40, according to some embodiments. For example, as illustrated in FIGS. 13 and 21 where the baseplate 40 includes two valve apertures 48. The features of the baseplate 40 shown in FIGS. 27A-D may be similar or the same as the features of the baseplate having three valve apertures 48 (e.g., FIGS. 9-12), for example, it may have the same or similar structure of a side surface 44, circumferential ridges 45, and/or the angles of the valve apertures 48. In embodiments having two or three valve apertures, the valve apertures may be aligned at a 15° angle relative to the longitudinal axis of the baseplate, angling inward from the distal side of the baseplate to the proximal side of the baseplate. This alignment advantageously provides uniform symmetrical air flow from the valves into proximal side of the main aperture 47 to facilitate the flow of urine through the main aperture 47 and out of the discharge tube 55 when a suction is applied to the discharge tube 55. In some embodiments, the valve apertures may be aligned at another angle. For example, in some embodiments, the valve apertures are aligned at an angle (relative to the longitudinal axis of the baseplate) of 0°, 1°, 2°, 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, 30°, 31°, 32°, 33°, 34°, 35°, 36°, 37°, 38°, 39°, 40°, 41°, 42°, 43°, 44°, plus or minus 0.5°. In some embodiments, the valve apertures are aligned at an angle between about 9° and about 21°. In some embodiments, the valve apertures are aligned at an angle between about 12° and about 18°. At certain larger angles, shorter valves may have to be used such that the distal end 52 of the valve can be positioned within the vented housing 12. In some embodiments, aligning valve apertures 48 and an inward angle (e.g., of about 15°) also positions the proximal end 51 of the valve to contact a portion of an O-ring 50 and can help secure the O-ring 50 to the baseplate 40.

FIG. 28A-D illustrate schematics and certain dimensions of another example baseplate 40, according to some embodiments. For example, the embodiment illustrated in FIG. 17. The baseplate 40 in FIGS. 28A-D includes four valve apertures. In this example, the valve apertures are aligned at a 7.5° angle relative to the longitudinal axis of the baseplate. This angle allows the four valves to angle inward and still fit within the rear housing 12. The four valve apertures may be arranged symmetrically around the main aperture 47. This alignment advantageously provides uniform symmetrical air flow from the valves into proximal side of the main aperture 47 to facilitate the flow of urine through the main aperture 47 and out of the discharge tube 55 when a suction is applied to the discharge tube 55. In some embodiments, the valve apertures may be aligned at another angle. For example, in some embodiments, the valve apertures are aligned at an angle (relative to the longitudinal axis of the baseplate) of 0°, 1°, 2°, 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, 30°, 31°, 32°, 33°, 34°, 35°, 36°, 37°, 38°, 39°, 40°, 41°, 42°, 43°, 44°, 45°, plus or minus 0.5°. In some embodiments, the four valve apertures are aligned at an angle between about 3° and about 11°. In some embodiments, the four valve apertures are aligned at an angle between about 5° and about 10°. In some embodiments (e.g., when the valve apertures are at a greater angle) shorter/smaller valves may be needed to ensure the valves fit within the vented housing 12. In some embodiments, aligning valve apertures 48 and an inward angle (e.g., of about 7.5°) also positions the proximal end 51 of the valve to contact a portion of an O-ring 50 and can help secure the O-ring 50 to the baseplate 40.

Figure 29A:
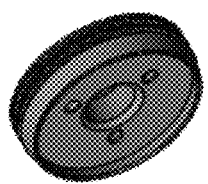
FIG. 29A illustrates a set of schematics of an example baseplate, according to some embodiments.
Figure 29A:
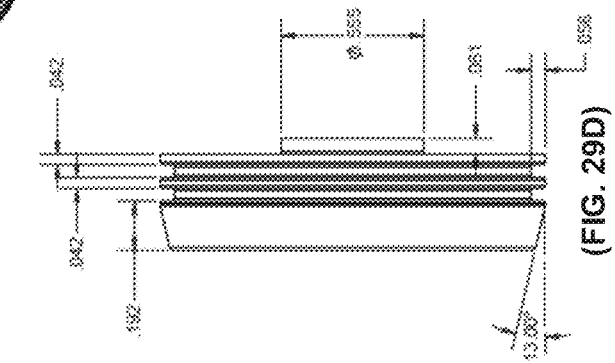
Figure 29A:
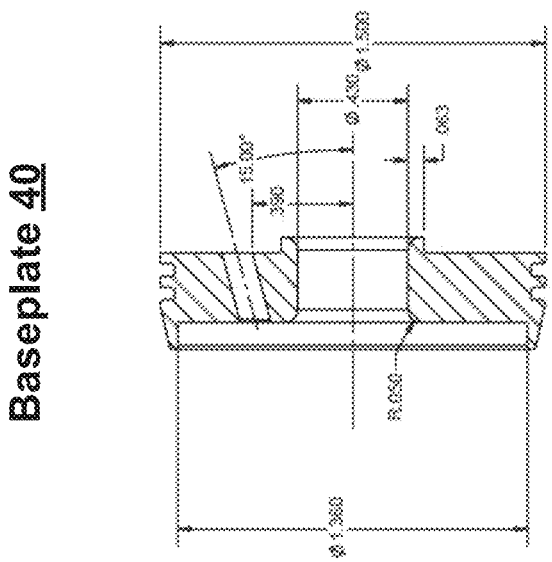
Figure 29A:
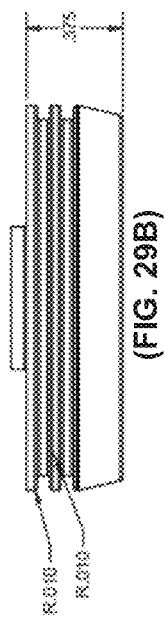
Figure 29A:
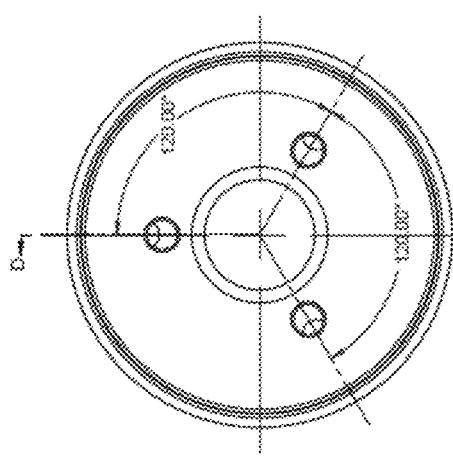
Figure 29B:
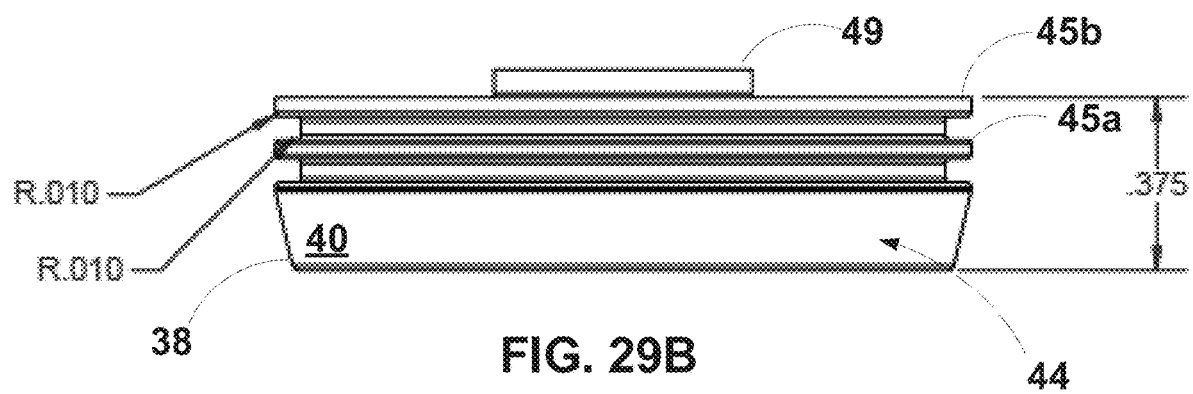
FIG. 29B illustrates a side view of the baseplate illustrated in FIG. 29A, and shows dimensions (in inches) of certain features of the baseplate.
Figure 29C:
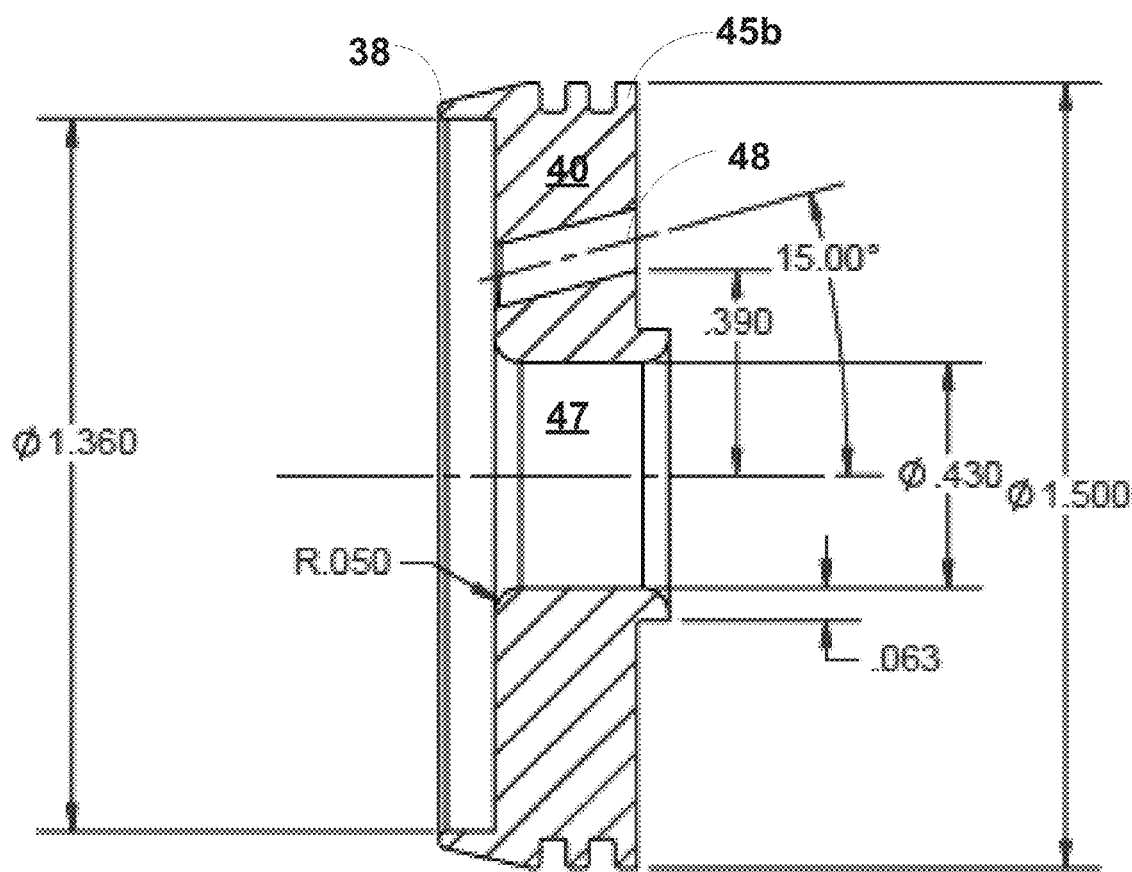
FIG. 29C illustrates a cross-sectional view of the baseplate illustrated in FIG. 29A along line D-D, and shows dimensions (in inches) of certain features of the baseplate.
Figure 29D:
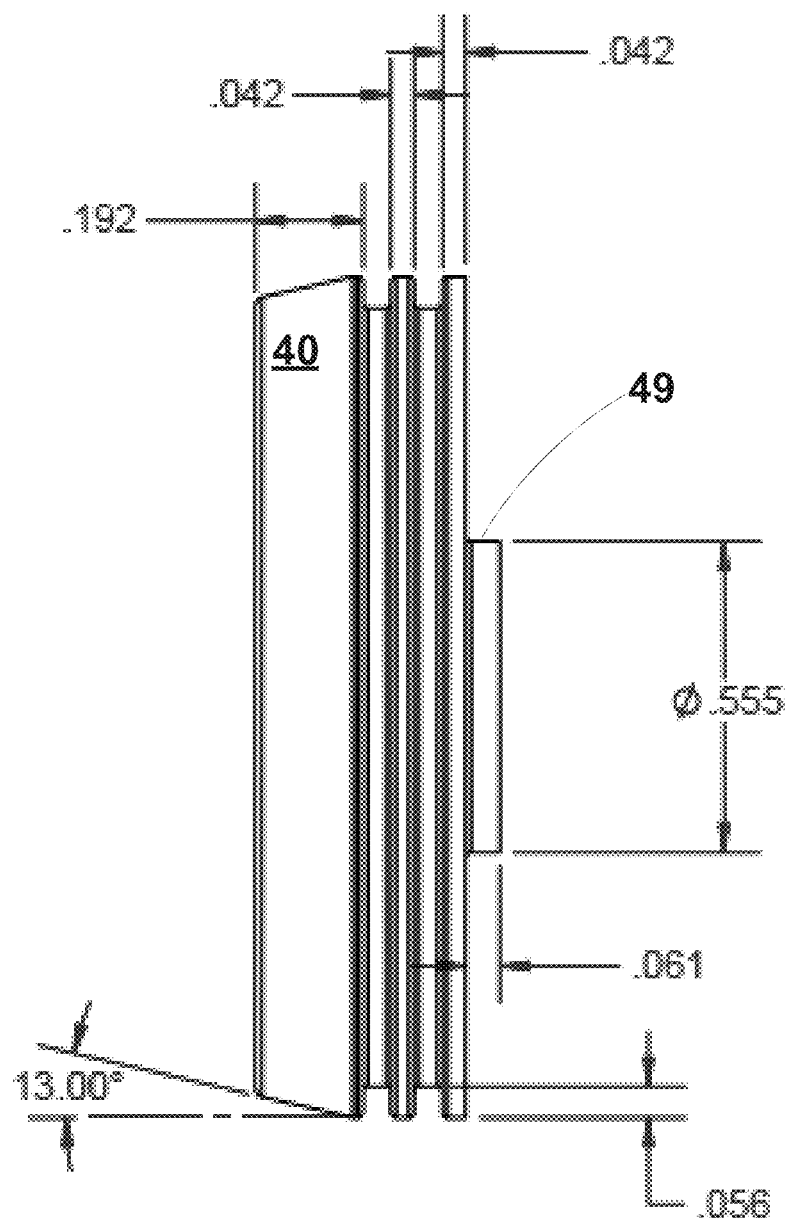
FIG. 29D illustrates another side view of the baseplate illustrated in FIG. 29A, and shows dimensions (in inches) of certain features of the baseplate.
Figure 29E:
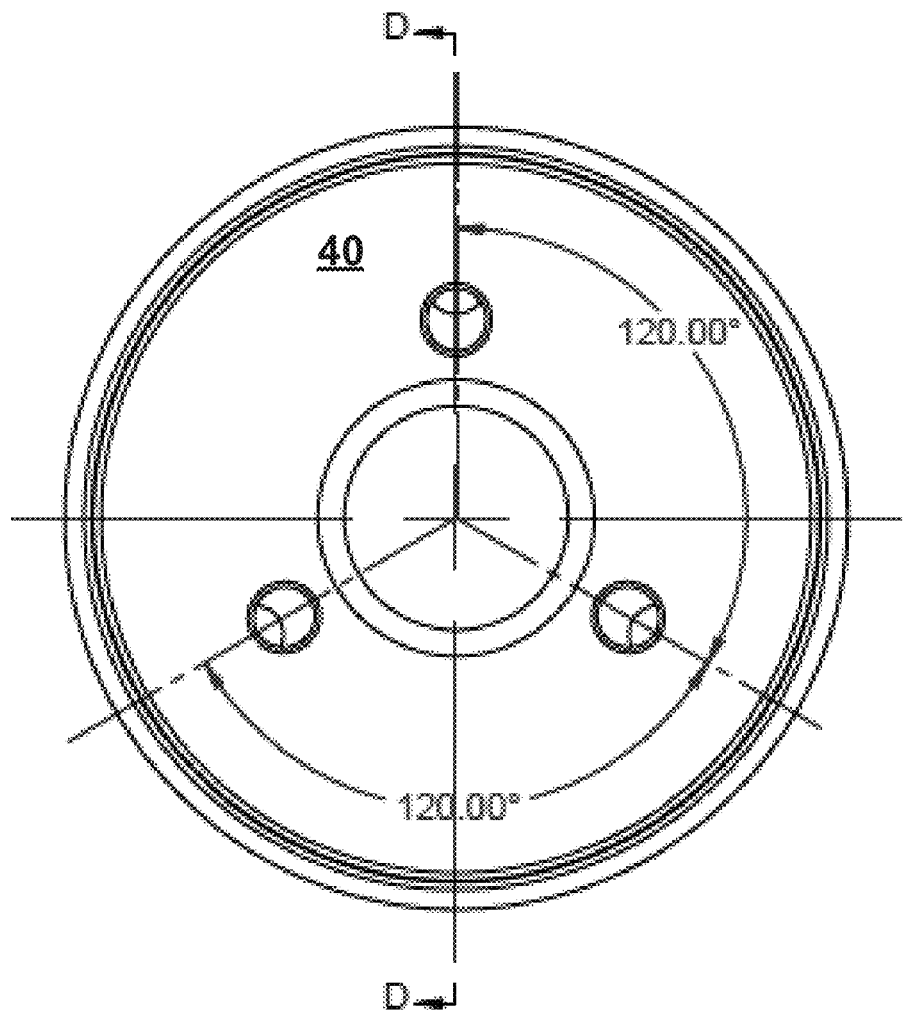
FIG. 29E illustrates a proximal-side plan view of the baseplate illustrated in FIG. 29A.

FIG. 29A-E illustrate another example baseplate, according to some embodiments. FIG. 29A illustrates a set of schematics of the baseplate 40. FIG. 29B illustrates a side view of the baseplate illustrated in FIG. 29A, and shows dimensions (in inches) of certain features of the baseplate (for example, the embodiment illustrated in FIGS. 3-12). FIG. 29C illustrates a cross-sectional view of the baseplate illustrated in FIG. 29A along line D-D, and shows dimensions (in inches) of certain features of the baseplate. FIG. 29D illustrates another side view of the baseplate illustrated in FIG. 29A, and shows dimensions (in inches) of certain features of the baseplate. FIG. 29E illustrates a proximal-side plan view of the baseplate illustrated in FIG. 29A. The baseplate 40 in FIGS. 29A-D includes three valve apertures. In this example, the valve apertures are aligned at a 15.0° angle relative to the longitudinal axis of the baseplate. The three valve apertures may be arranged symmetrically around the main aperture 47, 120° apart. This alignment advantageously provides uniform symmetrical air flow from the valves into proximal side of the main aperture 47 to facilitate the flow of urine through the main aperture 47 and out of the discharge tube 55 when a suction is applied to the discharge tube 55. In some embodiments, the valve apertures may be aligned at another angle. For example, in some embodiments, the valve apertures are aligned at an angle (relative to the longitudinal axis of the baseplate) of 0°, 1°, 2°, 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, 30°, 31°, 32°, 33°, 34°, 35°, 36°, 37°, 38°, 39°, 40°, 41°, 42°, 43°, 44°, 45°, plus or minus 0.5°. In some embodiments, the three valve apertures are aligned at an angle between about 9° and about 21°. In some embodiments, the three valve apertures are aligned at an angle between about 12° and about 18°. In some embodiments (e.g., when the valve apertures are at a greater angle) shorter/smaller valves may be needed to ensure the valves fit within the vented housing 12. In some embodiments, aligning valve apertures 48 and an inward angle (e.g., of about 15°) also positions the proximal end 51 of the valve to contact a portion of an O-ring 50 and can help secure the O-ring 50 to the baseplate 40.

The baseplate 40 in any of the embodiments may be sized such that when it is positioned inside of the collection tube 62, a side surface 44 of the baseplate 40 circumferentially contacts the inside surface of the collection tube 62, sealing the distal end of the collection tube 62 at this baseplate—collection tube interface, coupling the collection tube 62 to the baseplate 40 and the housing. With the baseplate 40 positioned inside the collection tube 62 and within the housing 10, an exterior surface of the collection tube 62, adjacent to where the baseplate 40 is positioned inside the collection tube 62, contacts an interior surface of the housing such that the collection tube 62 is held between the baseplate 40 and the housing 10 by an interference fit. The collection tube 62 is at least partially compressible, and thus may be compressed between the baseplate 40 and the housing 10, thus helping to couple the collection tube 62 to the housing 10.

Figure 17:
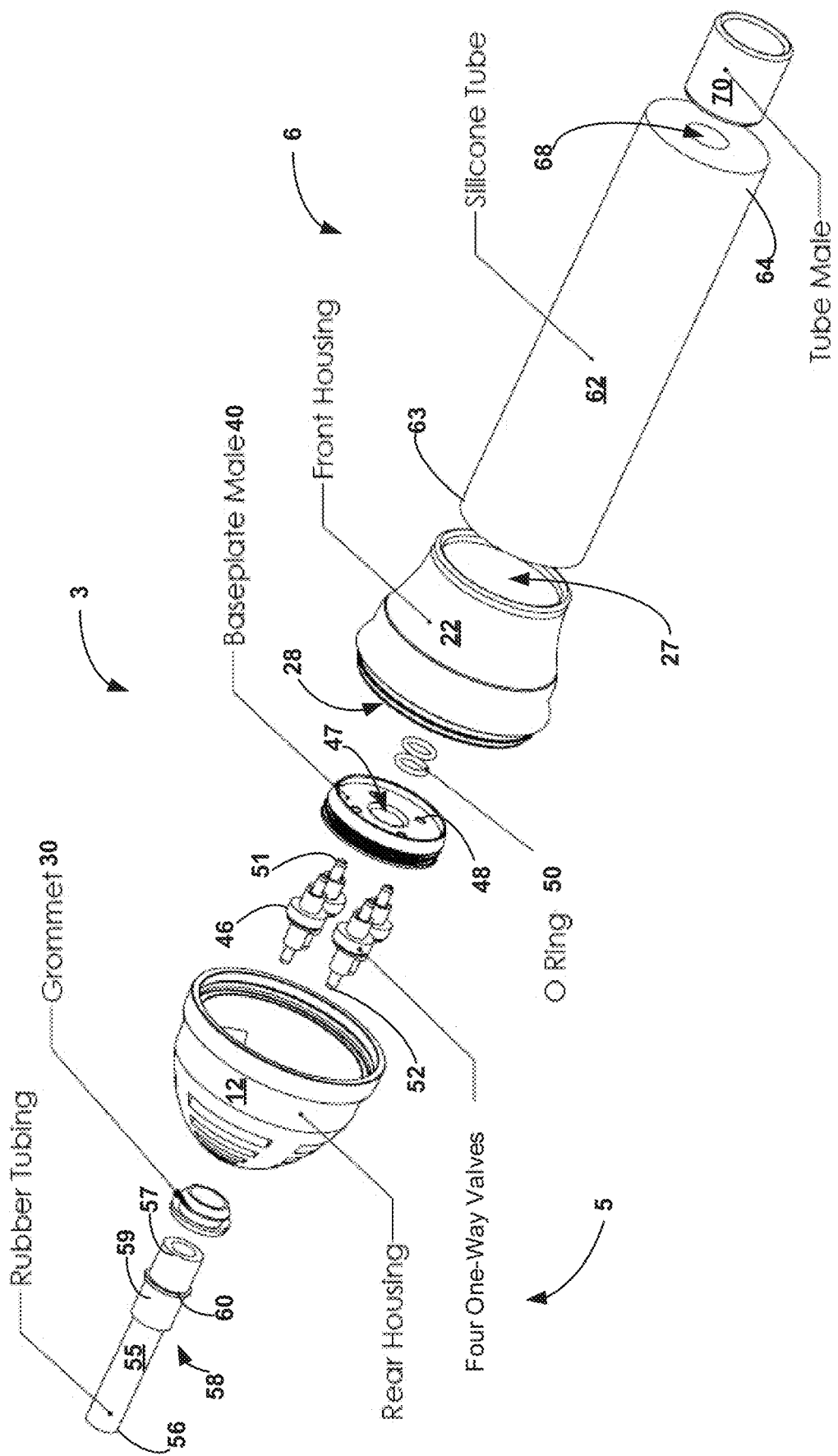
FIG. 17 is an exploded view illustrating certain components of a third embodiment of a fluid collection apparatus adapted to collect urine from a male urethra, this embodiment including four one-way valves positioned in the rear housing and coupled to the baseplate, the valves aligned such that a longitudinal axis of the valves is parallel, or nearly parallel, to a longitudinal axis of the collection device.
Figure 30A:
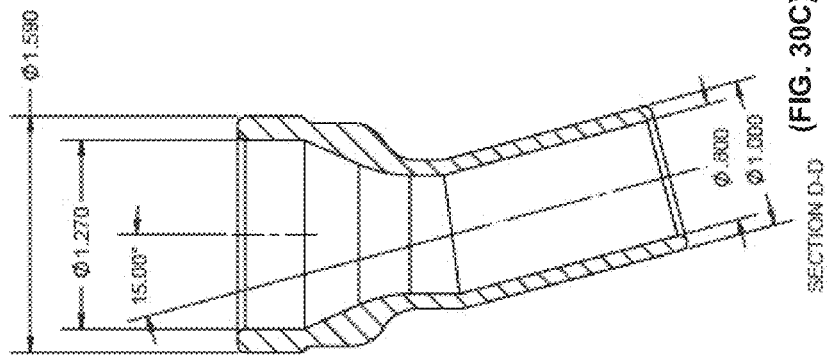
FIG. 30A illustrates a set of schematics of an example urethra tube 70 for a female.
Figure 30A:
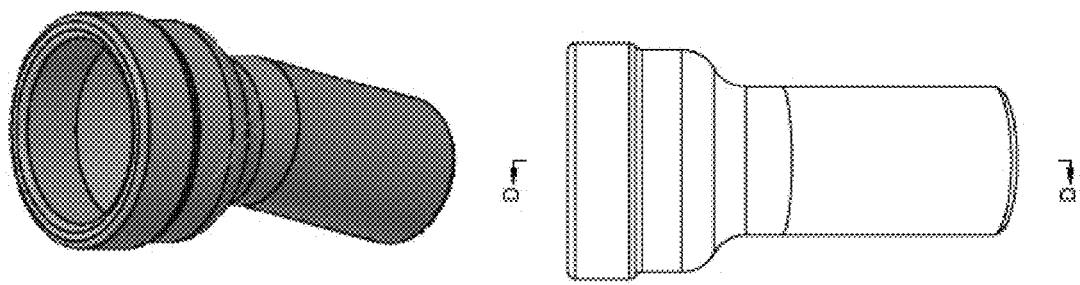
Figure 30A:
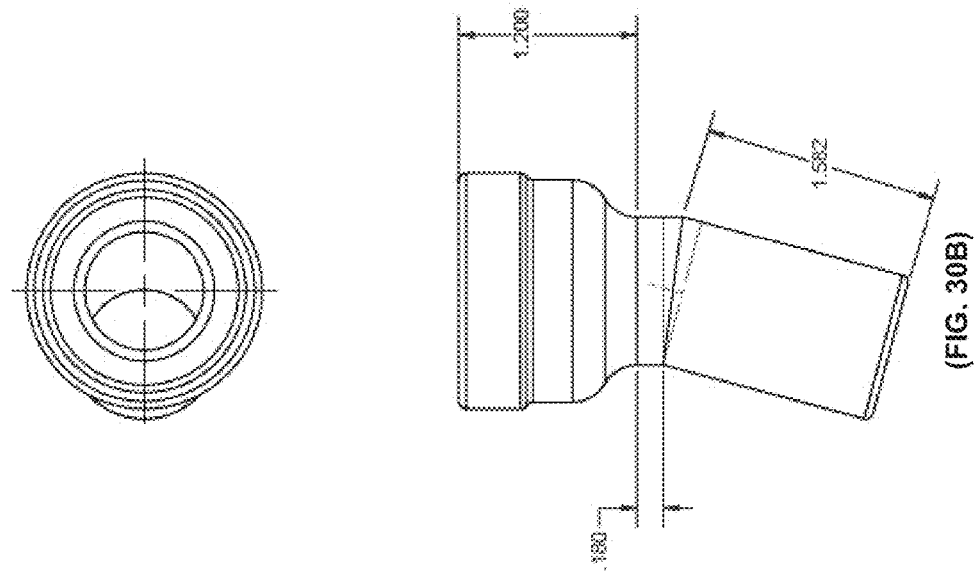
Figure 30C:
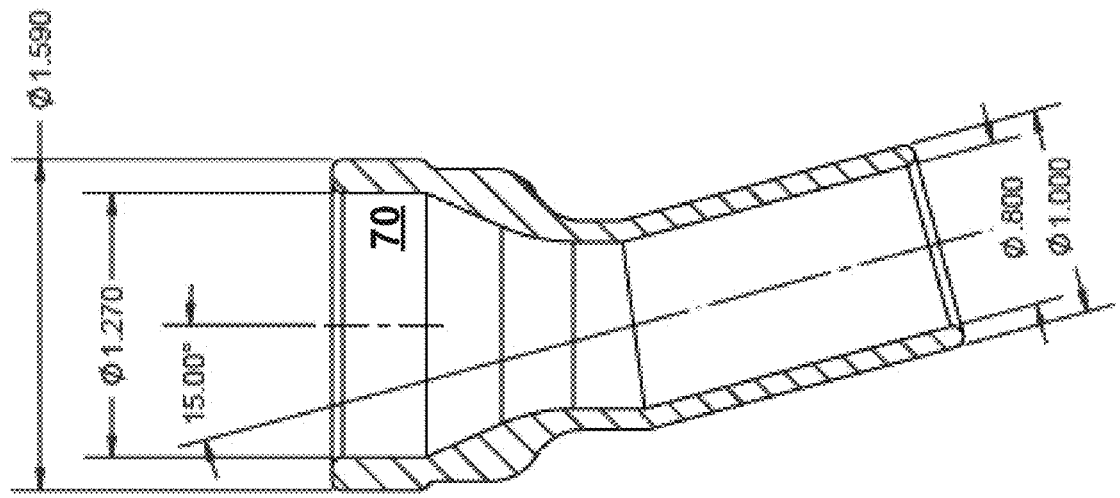
FIG. 30C illustrates a cross-sectional view of the urethra tube 70 illustrated in FIG. 30A along line D-D, shows certain dimensions (in inches), and shows an angle between a first longitudinal axis of a first portion of the urethra tube and a second longitudinal axis of a second portion of the urethra tube.
Figure 30B:
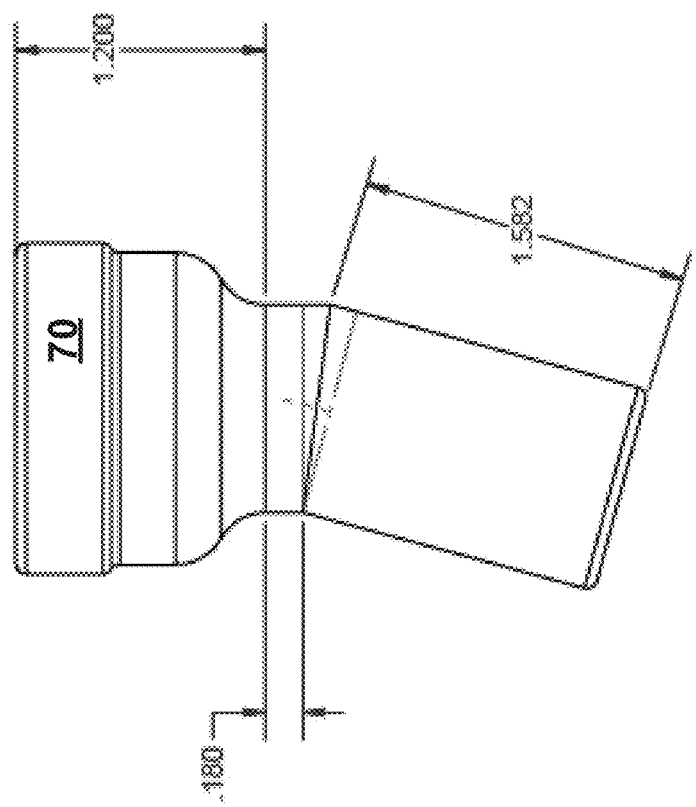
FIG. 30B illustrates a side view of the urethra tube 70 illustrated in FIG. 30A, and shows certain dimensions (in inches).
Figure 31:
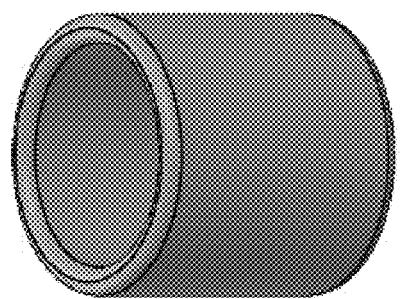
FIG. 31 illustrates a set of schematics of an example of a urethra tube 70 for use with a male patient, showing certain dimensions (in inches) or the urethra tube.
Figure 31:
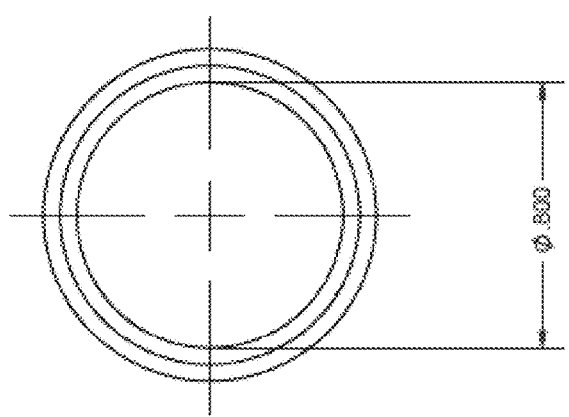
Figure 31:
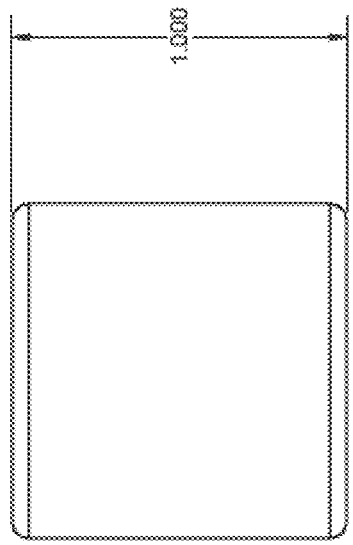

In the illustrated example, the proximal end of the collection tube 62 extends out of the proximal side of the front housing 22. A urethra tube 70, inserted into the collection tube 62, changes the shape of the proximal end of the collection tube 62 as the collection tube 62 conforms to the shape of the urethra tube 70. For example, in FIG. 4 and FIG. 13 the urethra tube 70 is shaped for interfacing with a female patient. In FIG. 17 and FIG. 21 the urethra tube 70 is shaped for interfacing with a male. FIGS. 30A-C illustrate additional views and certain dimensions of an example urethra tube 70 for a female, and FIG. 31 illustrates additional views and certain dimensions of an example urethra tube 70 for a male.

Further details and components of the embodiment illustrated in FIGS. 3 and 4 are described in reference to FIGS. 5-12. Three other embodiments of a fluid collection apparatus are described in reference to FIGS. 13-24. Other embodiments are also possible. The similar components in each of these embodiments are structured similarly and have similar functionality. Description of such components and their features with reference to one embodiment also apply to the components and functionality of the other illustrated embodiments, unless specifically indicated or as indicated by the context of the illustration or the description.

Figure 6:
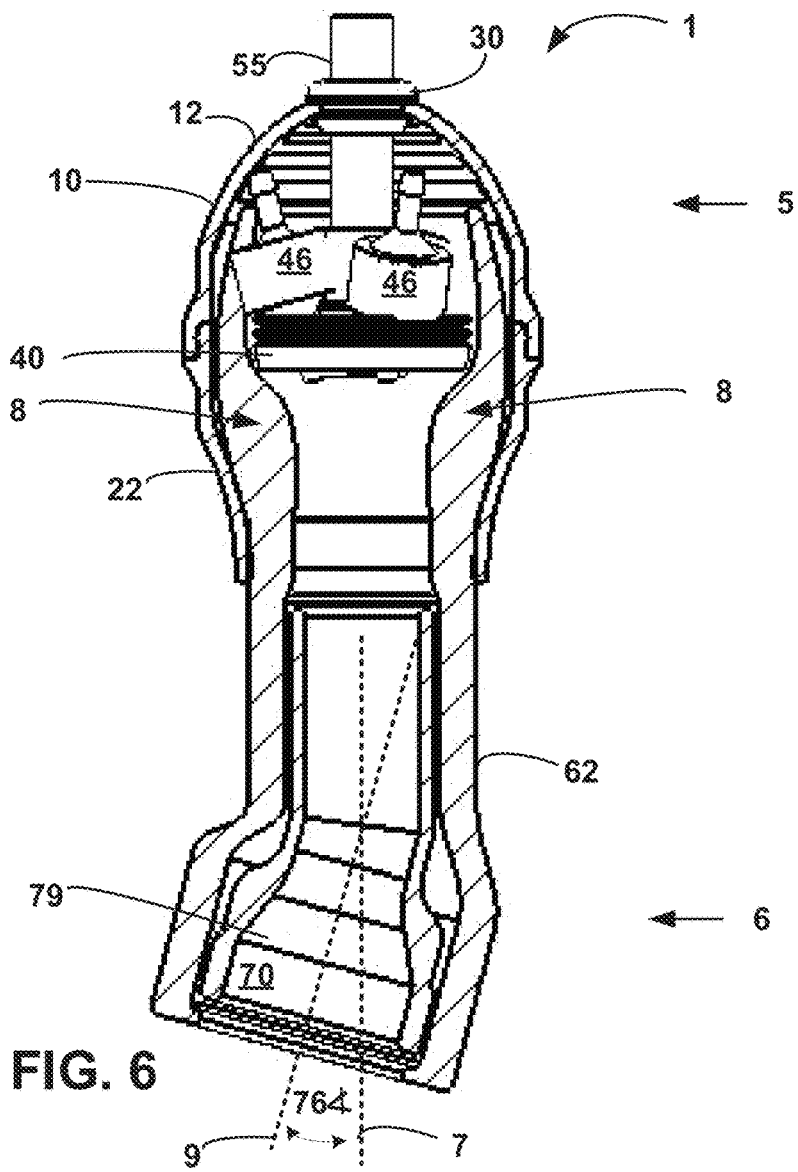
FIG. 6 is a side partial cross-sectional view along line B-B of FIG. 5 of the fluid collection apparatus of FIG. 4.
Figure 5:
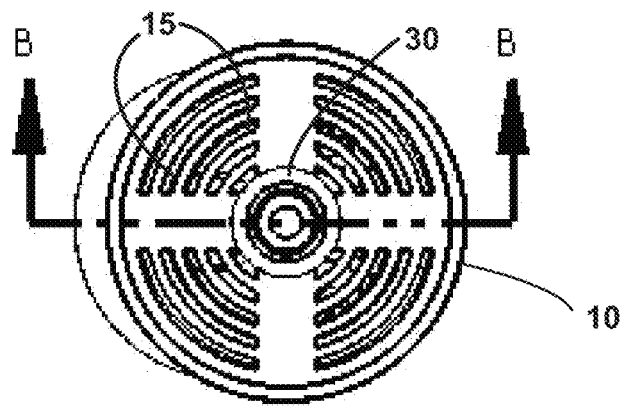
FIG. 5 is a distal end view of the fluid collection apparatus of FIG. 4.

FIG. 5 is a distal end view of the fluid collection apparatus shown in FIG. 4. FIG. 6 is a perspective partial cross-sectional view of the fluid collection apparatus shown in FIG. 3, along line B-B of FIG. 5. FIG. 5 illustrates an example of a plurality of vents 15 in a concentric circular arrangement on the housing 12. Other embodiments may have vents that are arranged in various other patterns. FIG. 6 further illustrates the interaction of the baseplate 40 contacting an inside surface of connection tube 62. The fluid collection apparatus may be assembled by inserting the baseplate 40 into the collection tube 62, deforming the collection tube 62 in a circumferential area 8, which creates the coupling of the connection tube to vented housing 10. In an example of assembling the collection apparatus, after the baseplate 40 is inserted into the distal end of the collection tube 62, the rear housing 12 is attached to the front housing 22 to form the vented housing 10. Before inserting the baseplate 40, valves 46 are coupled to the baseplate 40. Also before inserting the baseplate 40, the proximal end of the discharge tube 55 is coupled to the baseplate 40 and the distal end of the discharge tube 55 may be placed through an aperture in the rear housing 12 and through the grommet 30.

The connection tube 62 can be an elastomeric tube, deformable, with a consistent wall diameter and inner cavity (in an un-deformed state). FIG. 6 illustrates a collection tube 62 that has been deformed (or shaped) to conform to the outer dimensions and shape of the urethra tube 70. The collection tube 62 may be configured to have various shapes, sizes, and angled portions to form a desired interface with a female urethra by correspondingly shaped, sized and angled urethra tubes 70.

FIG. 6 also illustrates that a portion of the urethra tube 70 can have a flared portion 79. FIG. 6 further illustrates that a urethra tube 70 can have a two (or more) sections that are angled relative to each other. In an example, a distal section of the urethra tube 70 has a longitudinal axis 7 that is aligned with the longitudinal axis 7 of the collection apparatus 1, and a proximal section that has a longitudinal axis 9 that is aligned at an angle 76 relative to the longitudinal axis 7.

Figure 7:
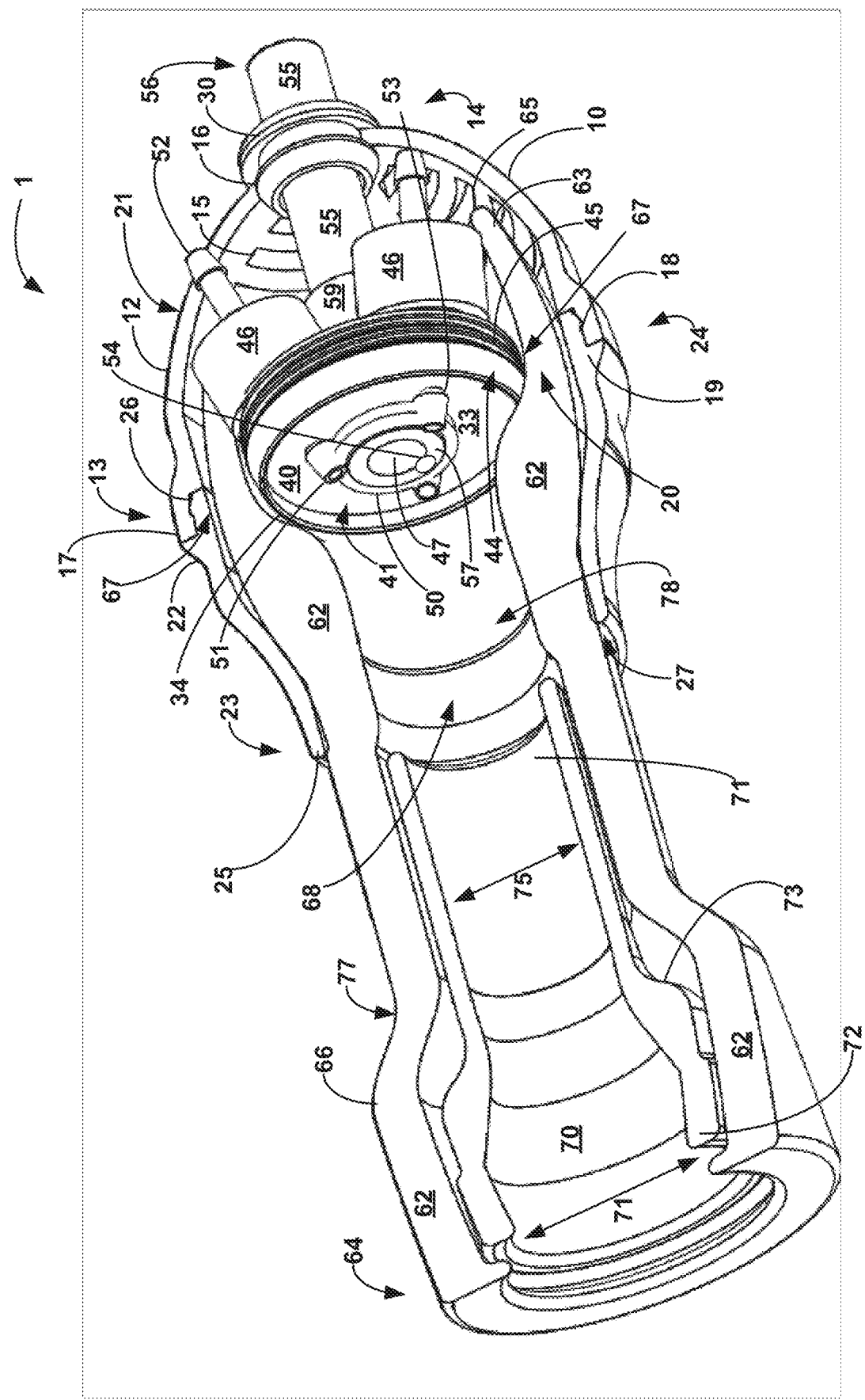
FIG. 7 is a proximal perspective partial cutaway view illustrating certain details of the structure of the fluid collection apparatus shown in FIG. 4.
Figure 8:
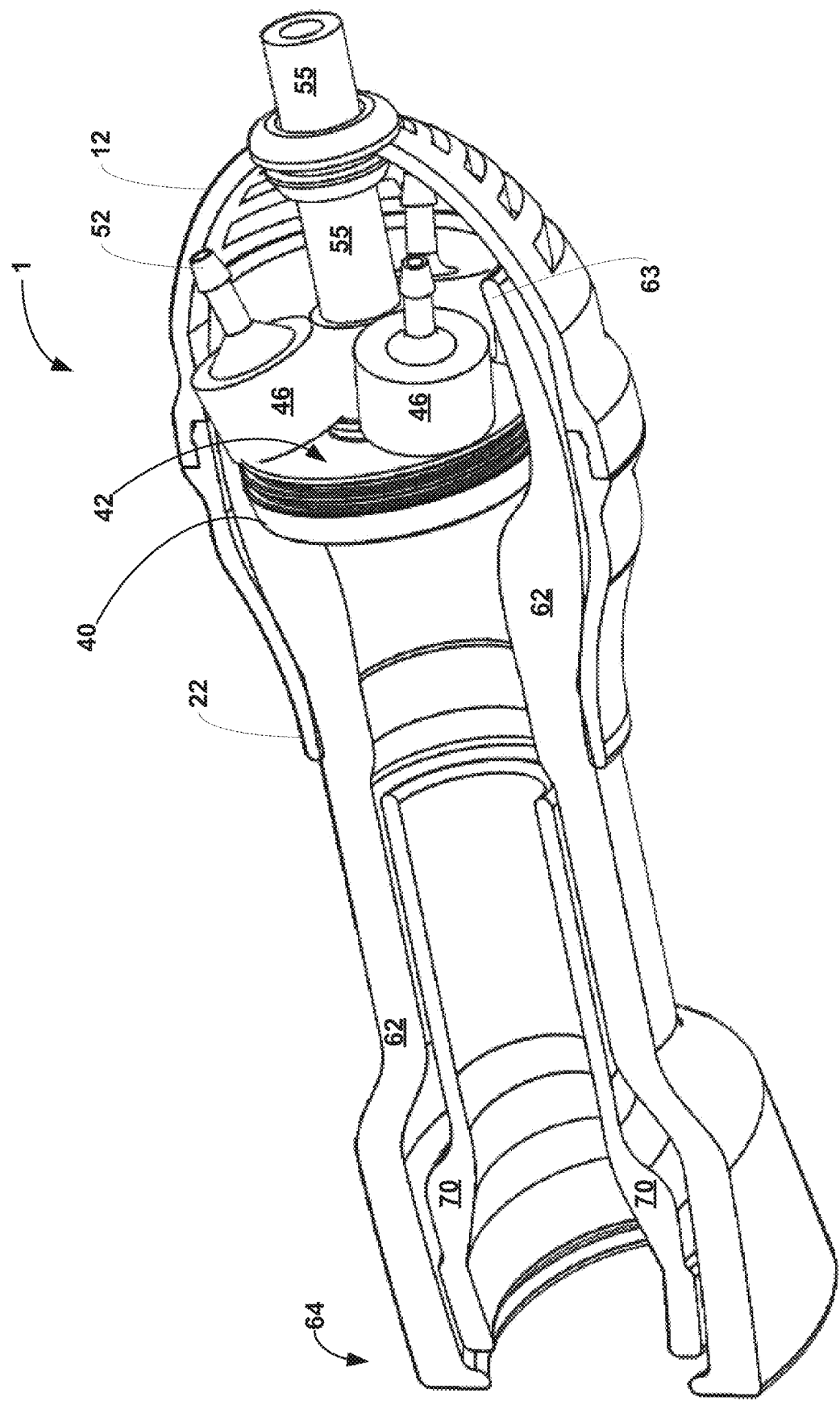
FIG. 8 is a distal perspective partial cutaway view illustrating certain details of the structure of the fluid collection apparatus shown in FIG. 4.

FIG. 7 is a proximal perspective partial cutaway view illustrating certain details of the structure of the fluid collection apparatus 1 shown in FIG. 4. FIG. 8 is a distal perspective partial cutaway view illustrating components discussed above and certain additional details of the structure and components of the assembled fluid collection apparatus embodiment shown in FIG. 7 (for example, the distal side 42 of the baseplate 40). As illustrated in the example of FIG. 7, the vented housing 10 includes vents 15 in the exterior surface 21 of the rear housing 12. The rear housing 12 has a proximal end 13 and a distal end 14. The rear housing 12 has a first aperture 16 and a second aperture 20. Grommet 30 is positioned in the first aperture 16, a portion of the grommet 30 extending into the interior of the rear housing 12 and a portion of the grommet extending outside of the rear housing 12. An outer edge 17 of the rear housing 12 defines an edge of the second aperture 20, and contacts the front housing 22 when the coupling portion 18 of the rear housing 12 is coupled with the coupling portion 19 of the front housing 22. In this embodiment, a coupling portion 19 of the front housing 22 fits inside the coupling portion 18 of the rear housing 12. The front housing 22 and the rear housing 12 may be structured to be releasably coupled together. The front housing 22 includes a proximal end 23 and a distal end 24. The front housing 22 also has an outer edge 25 of the proximal end that defines the edge of the first aperture 27 of the front housing 22, and an outer edge 26 that defines the edge of the second aperture 28 of the front housing 22, the second aperture 28 being on the distal end 24 of the front housing 22. The first aperture 27 has a smaller diameter than the second aperture 28, and the contour of the front housing 22 correspondingly curves as the diameter of the front housing 22 increases from the outer edge 25 of the proximal end 23 to the outer edge 26 of the distal end 24.

As illustrated in FIG. 7, the distal end 63 of the collection tube 62 extends through the first aperture 27, around the baseplate 40, and into the vented housing 10 to a termination point 65. The termination point 65 may be past the baseplate 40 to an extent such that the entire baseplate 40 is inside of the collection tube 62. The termination point 65 may past the baseplate 40 to an extent such that the distal end 63 of the collection tube 62 extends past at least a portion of the valves 46. The baseplate has a proximal side 41 and a distal side 42. The baseplate 40 further includes a proximal surface 33 generally facing towards the urethra tube 70 and a distal surface 32 generally facing towards the distal end of the rear housing 12. A proximal edge 34 is at the proximal end of an edge wall 36 that extends away from the baseplate proximal surface 33. The edge wall 36 has an interior surface 35, a distal portion 37 and a proximal portion 38. The edge wall 36 also has a side surface 44. The side surface 44 can be angled such that a diameter of the baseplate at the proximal portion 38 of the edge wall 36 is less than the diameter of the baseplate at the distal portion 37 of the edge wall 36 (referred to herein as an "inward angle"). The inward angle of the side surface 44 makes it easier to insert the baseplate 40 into the collection tube 62, and at least a portion of the side surface 44 contacts the inside of the collection tube 62 when the baseplate 40 is inserted into the collection tube 62. The baseplate 40 can also include a circumferential ridge 45 on the edge of the baseplate. In some examples including the examples illustrated herein, the baseplate 40 may include two circumferential ridges 45. In some examples the baseplate 40 may include more than two circumferential ridges 45. When the baseplate 40 is inserted into the collection tube 22, the circumferential ridges 45 contact the inside surface of the collection tube 22 and provide for enhanced sealing between the baseplate 40 and the connection tube 62 interface.

When the baseplate 40 is inserted into the collection tube cavity 68 at the proximal end 64 of the collection tube 22, the connection tube 22 expands and contacts a circumferential inside housing contact surface 67. Because the front housing 22 has a smaller diameter at the proximal end 23 than the distal end 24, the shape of the front housing 22 restricts the baseplate 40/connection tube 22 assembly from moving in the proximal direction and securely holds the connection tube 22 in the housing 10. In an example of removing the collection tube 22 from the housing 10, the front housing 22 is separated from the rear housing 12, the baseplate 40 is removed from the collection tube 22 allowing the collection tube 22 to contract, and the distal end 63 of the collection tube 22 is pulled out of the front housing 22.

The baseplate 40 includes a main aperture 47. In operation, urine passes from the collection tube 22 through the main aperture 47 to the discharge tube 55. In this embodiment, the main aperture 47 is located in a center portion of the baseplate 40. In other embodiments, the main aperture 47 may be offset from the center of the baseplate 40. The baseplate 40 also includes a valve aperture 48. The embodiment in FIG. 7 includes three valve apertures 48. Each valve 46 includes a first end 51 and a second end 52. The first end 51 may extend through a valve aperture 48 and protrude from the baseplate 40 on the proximal side of the baseplate 40. The second end 52 is positioned in the rear housing 12. In this example, the proximal end 57 of the discharge tube 55 extends through the main aperture 47 and may be coupled to the baseplate 40 by an O-ring 50 positioned around the proximal end 57. Some embodiments may include more than one O-ring 50 (e.g., two O-rings). The O-ring 50 can inhibit or prevent the proximal end from being pulled back through the baseplate 40. In some embodiments, a coupler 58 (FIG. 11) may include a sleeve 59 that fits around a portion of the discharge tube 55 and may be used to couple the discharge tube 55 to the baseplate 40. For example, by connecting to protrusion 49 (FIG. 10) that extends from the distal side of the baseplate 40. In some embodiments, a ring structure 60 (FIG. 10) may be used to attach the sleeve 59 to the discharge tube 55. The ring structure 60 may also limit the extent the discharge tube 55, or the coupler portion 58, extends through the baseplate 40. Projections 53 on the first end 51 of the valves 46 may extend over and contact the O-ring 50, and couple the O-ring 50 and the discharge tube 55 to the baseplate 40.

In some embodiments, at least one sensor 54 may be mounted on the proximal side of the baseplate 40 to sense a condition or a substance in the collection tube 62. Although FIG. 7 illustrates just one sensor 54, in other embodiments one or more additional sensors may be positioned in a portion of collection tube 62 to sense a condition or a substance in the collection tube, for example, a substance in urine in the collection tube 62. For example, the sensor can be configured to generate a signal when it detects fluid. The signal can be communicated (e.g., wirelessly or with a wired connection) to activate a vacuum pump to produce a level of suction in the collection tube 62 when fluid is present (e.g., a higher level of suction). In some embodiments, a sensor 54 may also be configured to monitor air pressure in the collection tube 62. In various embodiments, the at least one sensor may include a moisture sensor, a blood sensor, a sodium chloride sensor, a protein sensor, and/or a calcium sensor. In various embodiments of a fluid collection apparatus, other sensors may be included.

As illustrated in FIG. 7, the urethra tube 70 can be inserted into the proximal end 64 of the collection tube 62 such that the urethra tube 70 is positioned in the collection tube cavity 68 and contacts an interior surface 78 of the collection tube 62. The urethra tube includes a distal end 71 and a proximal end 72. The proximal end 72 is positioned near (e.g., inside or outside) the proximal end 64 of the collection tube 62. The proximal end 72 of the urethra tube 72 can include a flared portion 73, which may have a different size, shape and/or longitudinal axis than the rest of the urethra tube 72. For example, the illustrated urethra tube 72 has a first diameter 74 at the proximal end 72 and a second diameter 75 at the distal end 71, the first diameter 74 being larger than the second diameter 75. As illustrated in the example of FIG. 6, there is an angle 76 between a longitudinal axis of the flared portion 73 and a longitudinal axis of the rest of the urethra tube 70, for example, 15°. In some embodiments, the angle can be in the range of about 0° to about 90°. In some embodiments, the angle can be in the range of about 5° to about 35°. In some preferred embodiments, the angle can be in the range of about 8° to about 23°. For example, in some embodiments the angle can be: 0°, 1°, 2°, 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, 30°, 31°, 32°, 33°, 34°, 35°, 36°, 37°, 38°, 39°, 40°, 41°, 42°, 43°, 44°, 45°, 46°, 47°, 48°, 49°, 50°, 51°, 52°, 53°, 54°, 55°, 56°, 57°, 58°, 59°, 60°, 61°, 62°, 63°, 64°, 65°, 66°, 67°, 68°, 69°, 70°, 71°, 72°, 73°, 74°, 75°, 76°, 77°, 78°, 79°, 80°, 81°, 82°, 83°, 84°, 85°, 86°, 87°, 88°, 89°, or 90°, plus or minus 0.5°. In some embodiments, the angle can be greater than 90°. For example, equal to or between, 90° and 100°, 100° and 110°, 100° and 120°, 120° and 130°, 130° and 140°, 140° and 150°, 150° and 160°, 160° in 170°, or 170° and 180°.

The urethra tube 70 may be formed of a stiffer material (e.g., plastic, rubber, or non-latex materials) than the collection tube 62. The collection tube 62 stretches around the urethra tube 70 and conforms to the shape of the urethra tube 70, such that the exterior surface 77 of the collection tube 22 has the appearance of the shape of the urethra tube 70. This advantageously allows for a variety of shapes of urethra tubes to be used with the same collection tube component, which simplifies supplying and stocking these components.

Figure 9:
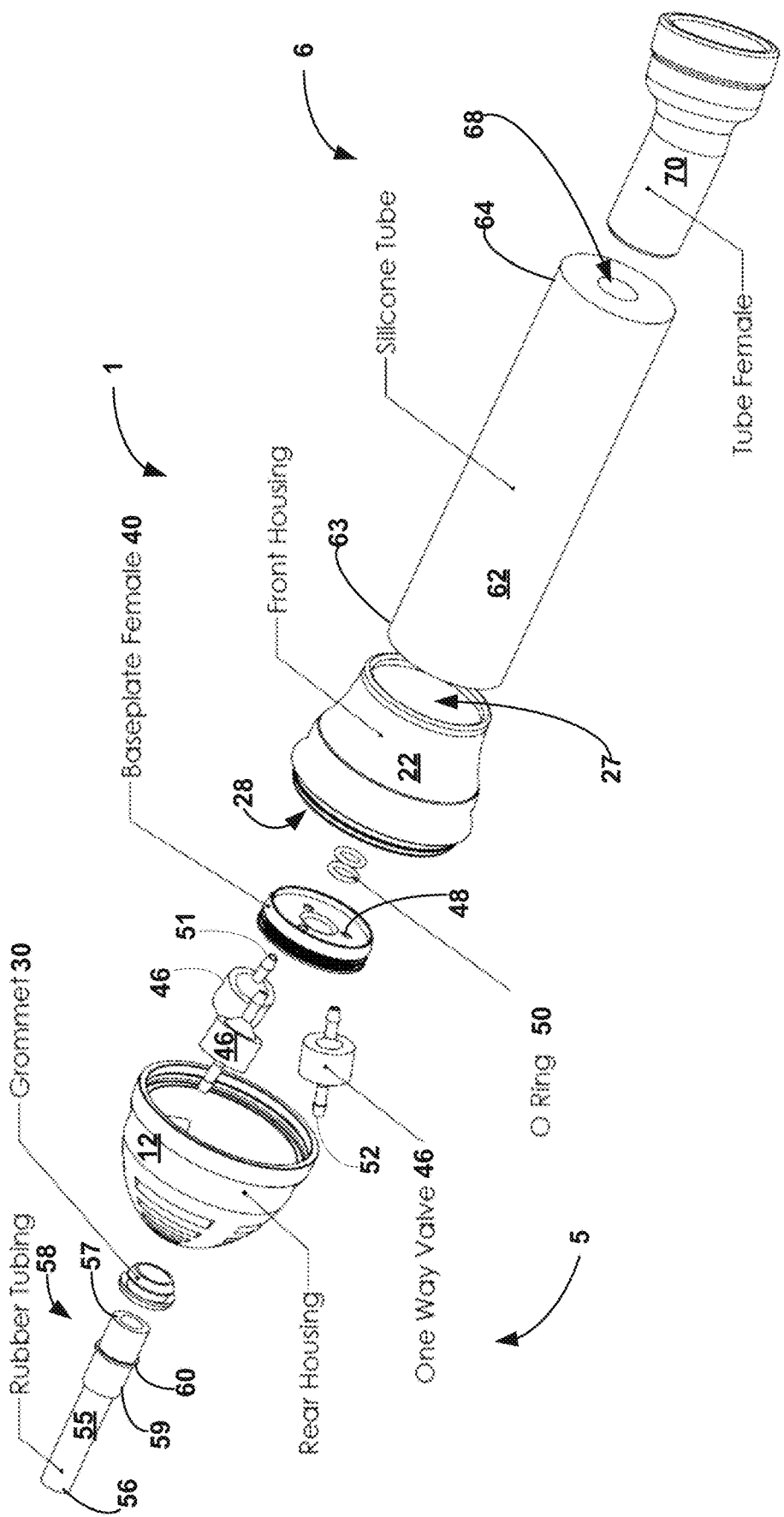
FIG. 9 is an exploded view illustrating certain components of the fluid collection apparatus shown in FIG. 4.

FIG. 9 is an exploded view illustrating another view of certain components of the fluid collection apparatus 1 shown and described above in FIGS. 3-7. In FIG. 9, the proximal end 6 of the fluid collection apparatus 1 is oriented on the right-hand side and the distal end 5 is oriented on the left-hand side.

Figure 10:
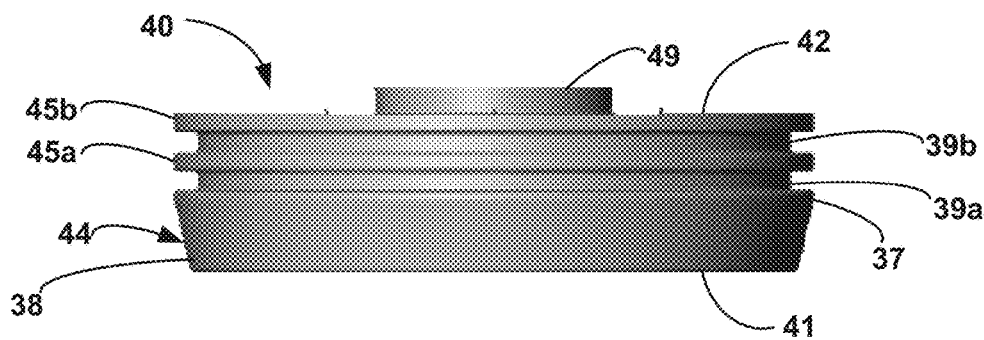
FIG. 10 is a side view of an example of a baseplate that can be in the fluid collection apparatus shown in FIG. 4.
Figure 11:
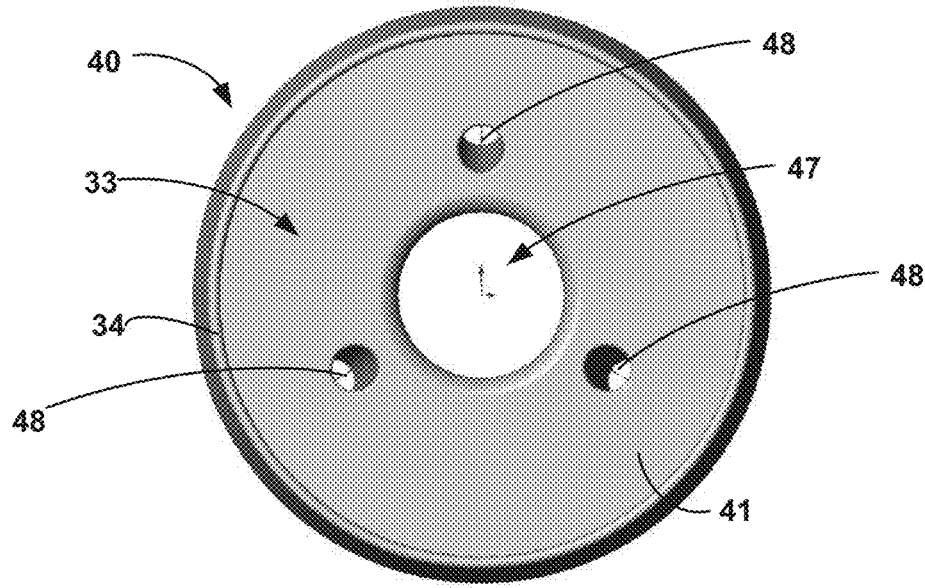
FIG. 11 is a proximal-side plan view of the baseplate shown in FIG. 10.

FIG. 10 is a side view of an example of a baseplate 40 that can be in the fluid collection apparatus 1 shown in FIGS. 3-9. FIG. 11 is a proximal-side plan view of the baseplate 40 shown in FIG. 10. FIG. 12 is a perspective view of the baseplate 40 shown in FIG. 10. The circumferential side (or edge) of the baseplate 40 includes a side surface 44. The circumferential side (or edge) of the baseplate 40 also includes a circumferential ridge 45. In this example, the baseplate includes two circumferential ridge 45*a*, 45*b*. The side also includes a circumferential concavity 39. A circumferential concavity 39 may be between a portion of the side surface 44 and a circumferential ridge 45. A circumferential concavity 39 may be between two adjacent circumferential ridges 45*a*, 45*b*. When the baseplate 40 is inserted into the distal end of the collection tube 62, the side surface 44 and the circumferential ridges 45 contact interior surface of the collection tube 62 and provide a tight seal between the collection tube 62 and the structures, essentially sealing the distal end of the collection tube 62 except for the main aperture 47 and the valve apertures 48 (which are blocked by valves 46 when mounted therein).

FIG. 10 illustrates the protrusion 49 extending from the distal side 42 of the baseplate 40. When coupled to the baseplate 40, a portion of the discharge tube 55 can extend through the protrusion 49, and the protrusion 49 helps to guide the discharge tube to extend through the baseplate 40. The protrusion 49 may be used to couple the discharge tube 55 to the baseplate 40. In an example, a sleeve 59 (FIGS. 7 and 9) or other portion of the discharge tube can fit around, fit through, or be coupled to the protrusion. As illustrated in FIG. 11, this embodiment includes three valve apertures 48 that extend through the faceplate 40 between the main aperture 47 and perimeter of the baseplate 40. In this embodiment, the valve apertures 48 are angled to have an "inward" orientation as the valve apertures 48 extend from the distal side 42 to the proximal side 41. In other embodiments, the valve apertures 48 may be aligned to be straight or have a different angular orientation FIG. 13 is an exploded view illustrating certain components of another embodiment of a fluid collection apparatus 2 for collecting urine from a female subject. Many of the components are similar to those described in reference to the first embodiment of the fluid collection apparatus 1 illustrated in FIGS. 3-10. However, this embodiment includes two valves 46. The valve apertures 48 are generally aligned to be angled inward. The urethra tube 70 is adapted to collect urine from a female urethra, and it can be sized and shaped appropriately for a tight connection around a female urethra.

Figure 14:
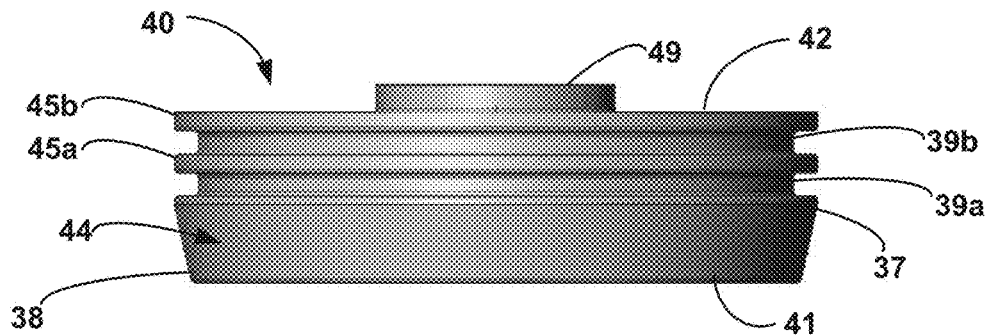
FIG. 14 is a side view of an example of a baseplate that can be in the fluid collection apparatus shown in FIG. 13.
Figure 15:
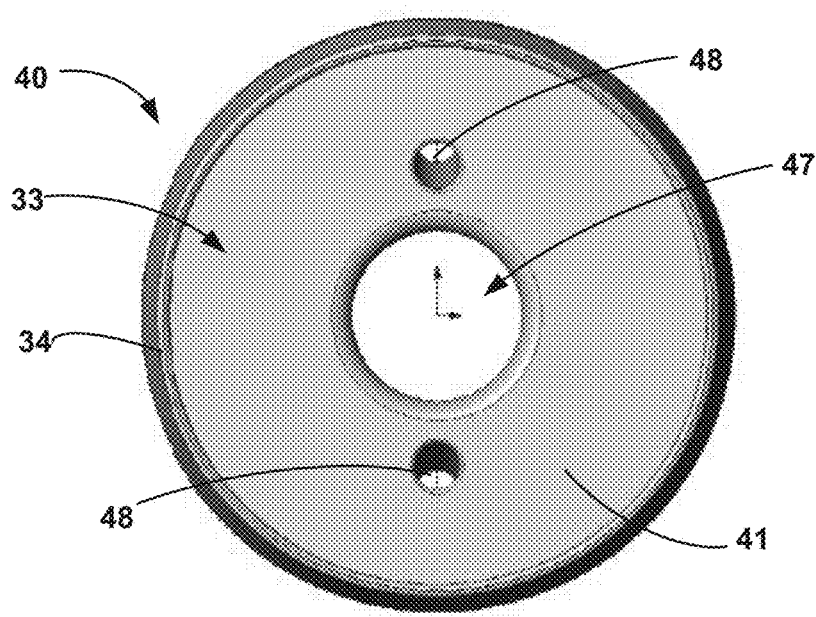
FIG. 15 is a proximal-side plan view of the baseplate shown in FIG. 14.
Figure 16:
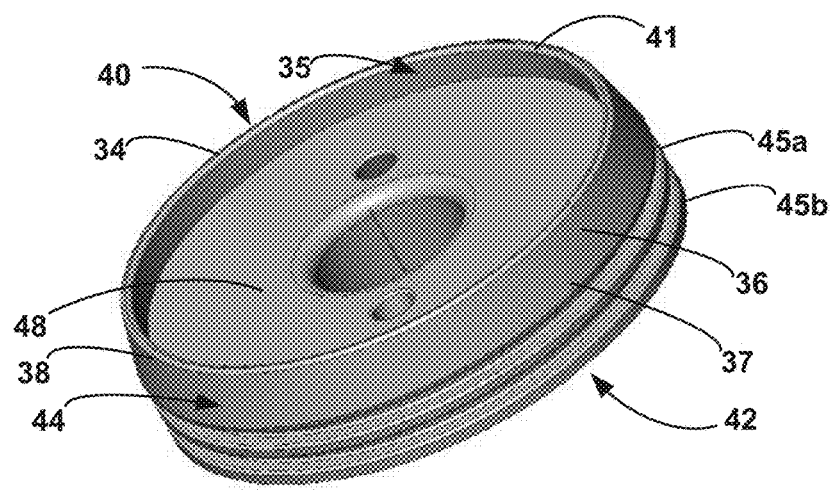
FIG. 16 is a perspective view of the baseplate shown in FIG. 14.

FIG. 14 is a side view of an example of the baseplate 40 in the fluid collection apparatus 2 shown in FIG. 13. FIG. 15 is a proximal-side plan view of the baseplate 40 shown in FIG. 13. FIG. 16 is a perspective view of the baseplate 40 shown in FIG. 13. The circumferential side (or edge) of the baseplate 40 includes a side surface 44. The circumferential side (or edge) of the baseplate 40 also includes a circumferential ridge 45. In this example, the baseplate includes two circumferential ridge 45*a*, 45*b*. The side also includes a circumferential concavity 39. A circumferential concavity 39 may be between a portion of the side surface 44 and a circumferential ridge 45. A circumferential concavity 39 may be between two adjacent circumferential ridges 45*a*, 45*b*. The baseplate 40 includes a protrusion 49 extending from the distal side 42 of the baseplate 40 around the main aperture 47. Two valve apertures 48 extend through the faceplate 40 between the main aperture 47 and the perimeter of the baseplate 40. As illustrated in this example, the valve apertures 48 may be angled to have an "inward" orientation as the valve apertures 48 extend from the distal side 42 to the proximal side 41 of the baseplate 40. In other embodiments, the valve apertures 48 may be aligned to be straight or have a different angular orientation, FIG. 17 is an exploded view illustrating certain components of another embodiment of a fluid collection apparatus 3 for collecting urine from a male subject. Many of the components are similar to those described in reference to the first embodiment of the fluid collection apparatus 1 illustrated in FIGS. 3-10. However, this embodiment includes four valves 46. The valve apertures 48 are generally aligned to be normal to the baseplate 40 which helps to fit the four valves 46 within the rear housing 12. The urethra tube 70 is adapted to collect urine from a male urethra, and it can be sized for a tight connection around a patient's penis. In an example, the urethra tube 70 may be of a transparent soft elastomeric material such as a silicone gel. The urethra tube 70 may include a plurality of ribs within the urethra tube 70 that provide improved gripping around the penis so that the penis is secured within the urethra tube 70 by the constriction of the urethra tube 70 and by a suction produced in the collection tube by an attached vacuum pump.

Figure 18:
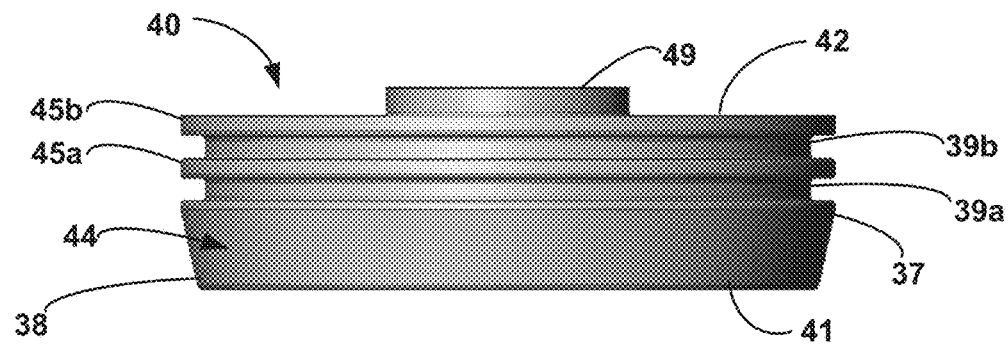
FIG. 18 is a side view of an example of a baseplate that can be in the fluid collection apparatus shown in FIG. 17.
Figure 19:
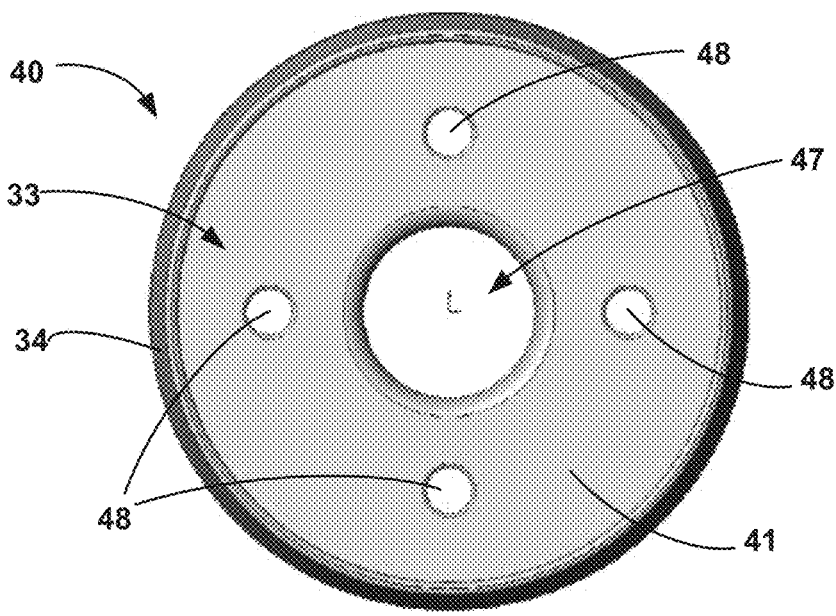
FIG. 19 is a proximal-side plan view of the baseplate shown in FIG. 18.
Figure 20:
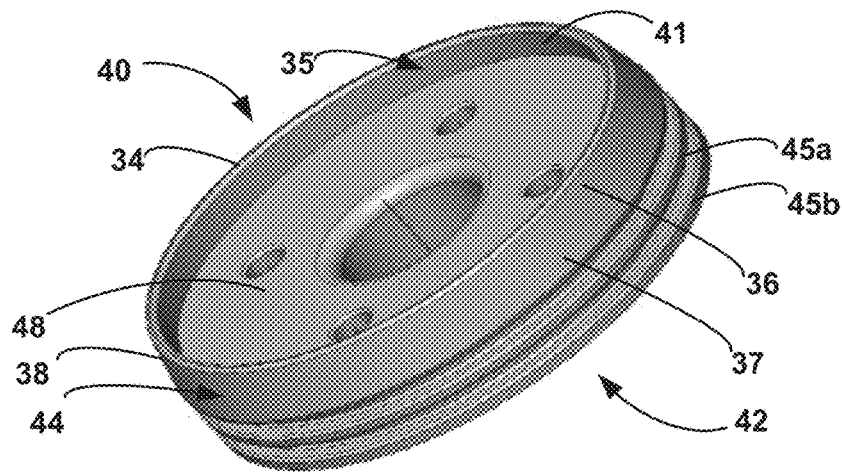
FIG. 20 is a perspective view of the baseplate shown in FIG. 18.

FIG. 18 is a side view of an example of the baseplate 40 of the fluid collection apparatus 3 shown in FIG. 17. FIG. 19 is a proximal-side plan view of the baseplate shown in FIG. 17. FIG. 20 is a perspective view of the baseplate shown in FIG. 17. The circumferential side (or edge) of the baseplate 40 includes a side surface 44. The circumferential side (or edge) of the baseplate 40 also includes a circumferential ridge 45. In this example, the baseplate includes two circumferential ridge 45*a*, 45*b*. The side also includes a circumferential concavity 39. A circumferential concavity 39 may be between a portion of the side surface 44 and a circumferential ridge 45. A circumferential concavity 39 may be between two adjacent circumferential ridges 45*a*, 45*b*. The protrusion 49 extends from the distal side 42 of the baseplate 40 around the main aperture 47, and can be used to couple the discharge tube 55 to the baseplate 40. This embodiment includes four valves 46 and four valve apertures 48 that extend through the faceplate 40 between the main aperture 47 and the perimeter of the baseplate 40. In this embodiment, the valve apertures 48 are aligned to be normal to the baseplate 40, which may help to fit the four valves within the rear housing. In other embodiments, the valve apertures 48 may be aligned to have a different angular orientation, FIG. 21 is an exploded view illustrating certain components of another embodiment of a fluid collection apparatus 4 for collecting urine from a male subject. Most of the components are similar to those described in reference to the first embodiment of the fluid collection apparatus 1 illustrated in FIGS. 3-10. This embodiment of the fluid collection apparatus 4 includes two valves 46. The valve apertures 48 are aligned to be at a non-normal angle relative to the orientation of the baseplate 40. In other embodiments, the valve apertures can be aligned to be normal to the orientation of the baseplate 40. The urethra tube 70 is adapted to collect urine from a male urethra, and it can be sized appropriately for a tight connection around a penis.

Figure 22:
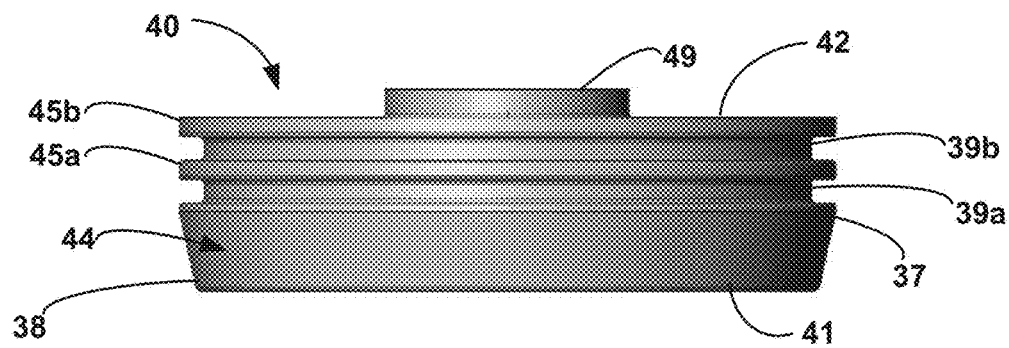
FIG. 22 is a side view of an example of a baseplate that can be in the fluid collection apparatus shown in FIG. 21.
Figure 23:
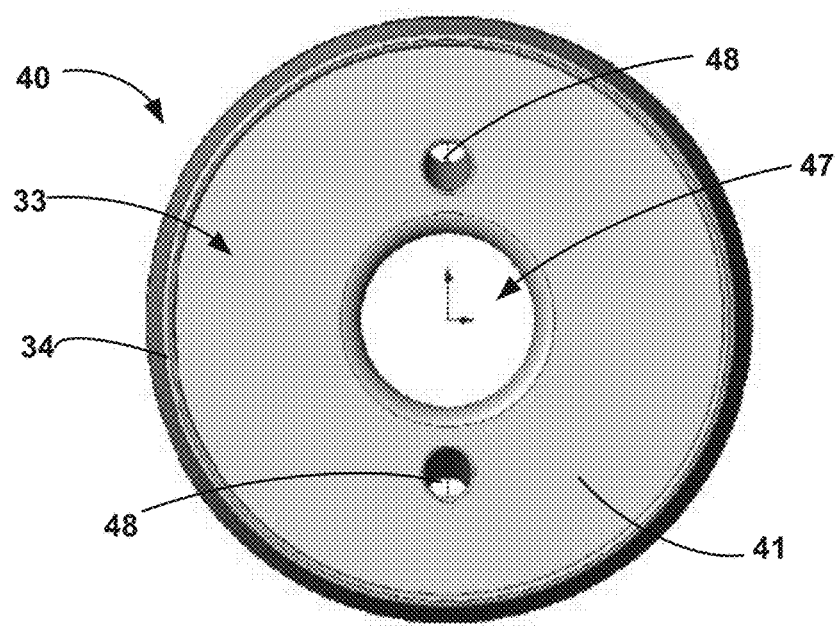
FIG. 23 is a proximal-side plan view of the baseplate shown in FIG. 22.
Figure 24:
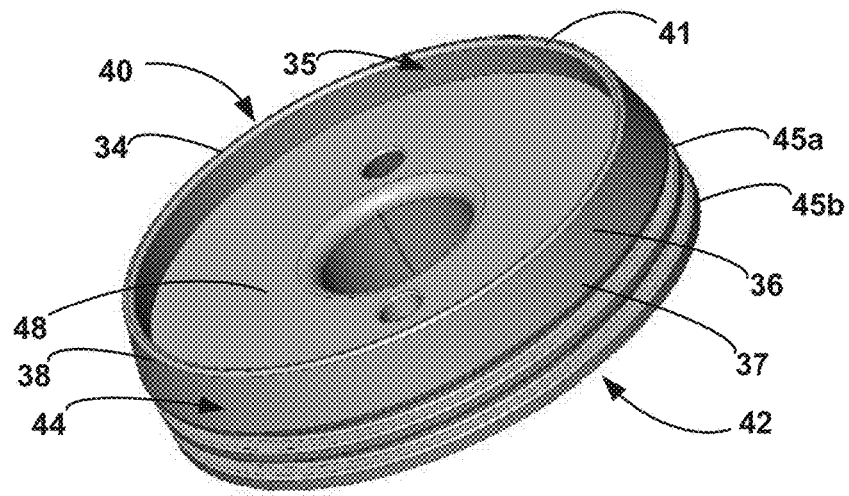
FIG. 24 is a perspective view of the baseplate shown in FIG. 22.

FIG. 22 is a side view of an example of a baseplate 40 that can be in the fluid collection apparatus 4 shown in FIG. 21. FIG. 23 is a proximal-side plan view of the baseplate shown in FIG. 21. FIG. 24 is a perspective view of the baseplate shown in FIG. 21. The circumferential side (or edge) of the baseplate 40 includes a side surface 44. The circumferential side (or edge) of the baseplate 40 also includes a circumferential ridge 45. In this example, the baseplate includes two circumferential ridge 45*a*, 45*b*. The side also includes a circumferential concavity 39. A circumferential concavity 39 may be between a portion of the side surface 44 and a circumferential ridge 45. A circumferential concavity 39 may be between two adjacent circumferential ridges 45*a*, 45*b*.

Figure 33:
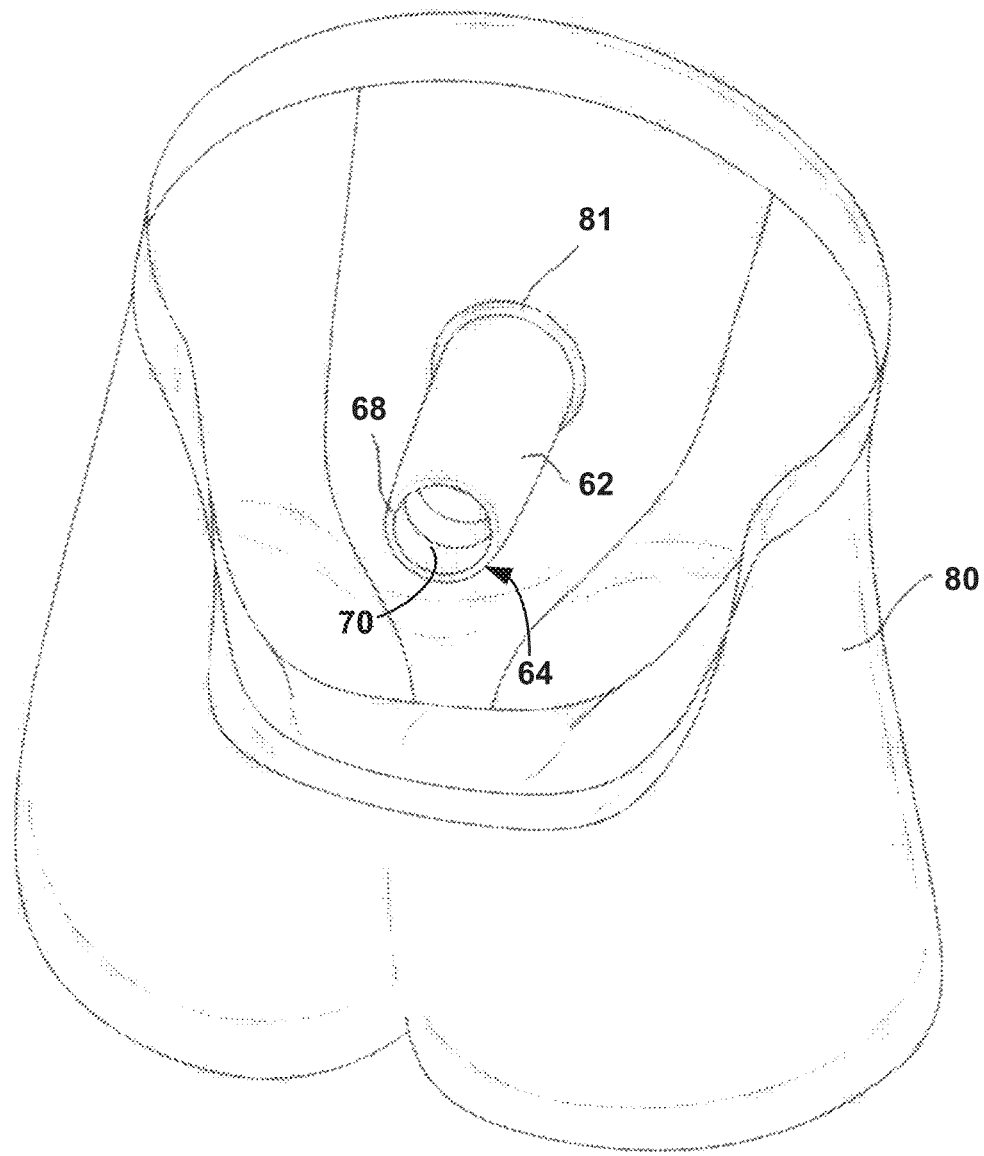
FIG. 33 is an illustration of the fluid collection apparatus disclosed incorporated into a garment.

The protrusion 49 extends from the distal side 42 of the baseplate 40 around the main aperture 47, and can be used to couple the discharge tube 55 to the baseplate 40. This embodiment includes two valve apertures 48 that extend through the faceplate 40 between the main aperture 47 and perimeter of the baseplate 40. In this embodiment, the valve apertures 48 are angled to have an "inward" orientation as the valve apertures 48 extend from the distal side 42 to the proximal side 41. In other embodiments, the valve apertures 48 may be aligned to be straight or have a different angular orientation, FIG. 33 is an illustration of a fluid collection apparatus disclosed herein incorporated into, or engaged with, a garment 80. The garment 80 may be an undergarment. For example, the garment may be pants, sweats, a robe, shorts, underwear, underpants, panties, a diaper, or a similar item which is worn by an individual when using the apparatus. In some embodiments, the garment 80 may be the specific garment provided by the hospital or another medical facility. The garment 80 may have an interface 81. The interface 81 may be an opening, select, a fold, or the like, that allows the collection tube 62 and the urethra tube 70 positioned in the collection tube 62, to pass through the interface 81 such that the collection tube 62 is accessible for use by a female or male patient. In some embodiments, the interface 81 can connect to the collection tube 62. For example, the interface 81 may include an elastic material to hold the interface against the collection tube 62. In some embodiments, the interface 81 includes a strong elastic edge or closure capable of helping to hold the collection tube 62 in place so that movement between the collection tube 62 in the garment 80 is minimized and loss of suction attachment is also minimized. When used with a garment, the collection tube 62 and urethra tube 70 may be held in place against the patient by suction as previously described. In some embodiments, the collection tube 62 and the urethra tube 70 may be held in place against the patient by suction as well as by the garment 80.

Figure 34:
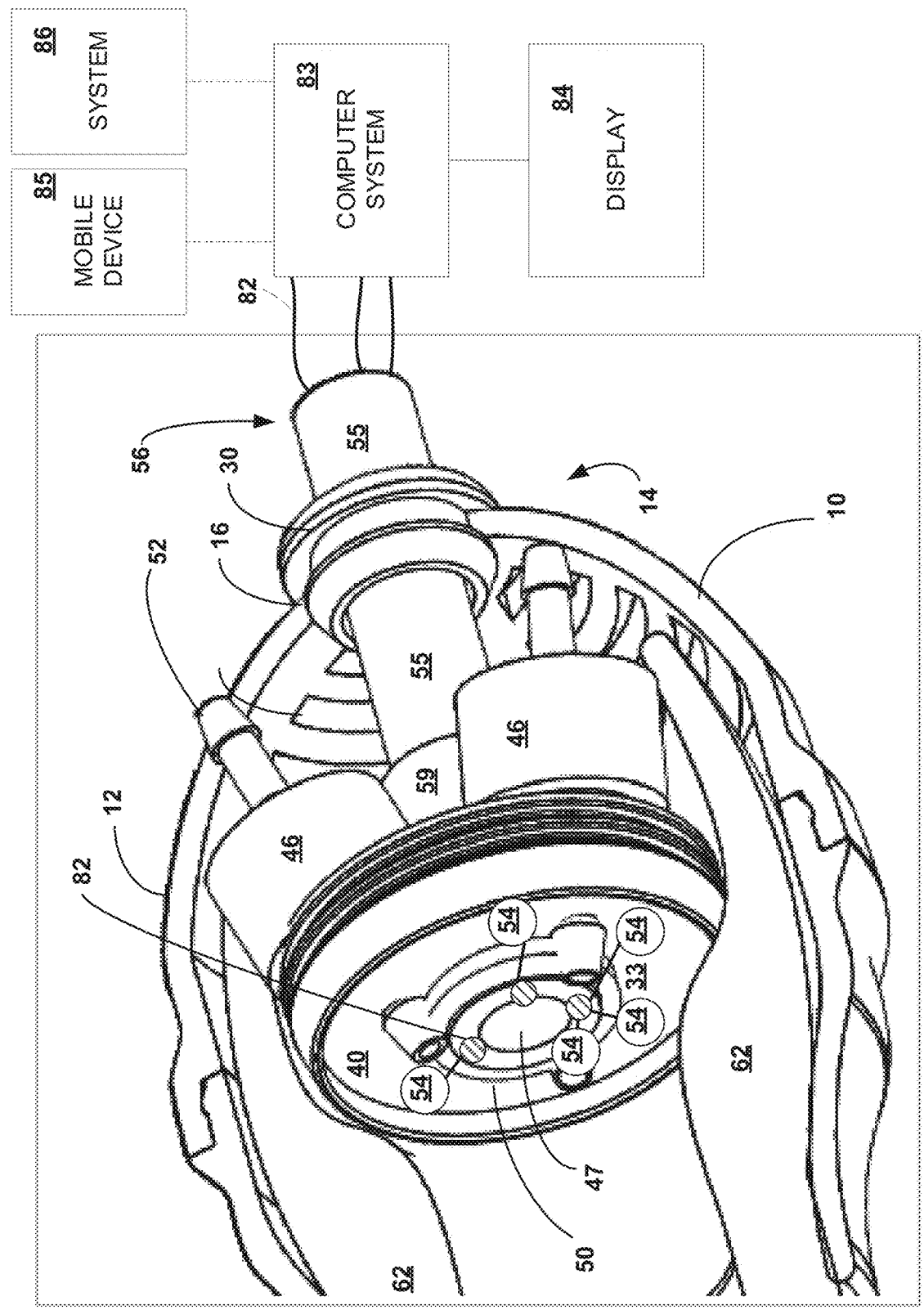
FIG. 34 is an illustration of an example of an embodiment of a fluid collection apparatus having a sensor (or more than one sensor) positioned to be in contact with fluid that enters the fluid collection apparatus.

FIG. 34 is an illustration of an example of an embodiment of a fluid collection apparatus having a sensor (or more than one sensor) positioned to be in contact with fluid that enters the fluid collection apparatus. As described in reference to FIG. 7, the fluid collection apparatus may have a sensor 54 that is positioned in a location to be in contact with fluid that enters the fluid collection apparatus. In reference to FIG. 34, one or more sensors 54 may be positioned inside the vented housing 10 to sense the presence of, or a characteristic of, a fluid in the fluid collection apparatus. The sensor 54 may be configured to sense the presence of moisture, blood, sodium chloride, protein, or calcium. The sensor 54 may be electronic sensor or optical sensor. In some embodiments, the sensor 54 is a chemical sensor that changes color to indicate the presence of, or a characteristic of, a fluid in the fluid collection apparatus, and the color can be seen through a transparent portion of the fluid collection apparatus (e.g., the housing, the collection tube). For example, a sensor 54 may be positioned within a portion of the collection tube 62 on or near the proximal side of the baseplate 40. In some embodiments, a sensor 54 may be mounted on the baseplate 40. In some embodiments, a sensor 54 may be mounted on a portion of the discharge tube 55, for example, a portion of the discharge tube 55 that extends through the baseplate 40. A sensor 54 may be wireless or maybe connected to a processing system by a wired connection. In one example, a wire 82 may be embedded in the discharge tube 55 such that a portion of the wire 82, on the proximal portion of the discharge tube 55 that extends to the baseplate 40, can be coupled to the sensor 54 that is either mounted on the baseplate, positioned in the chamber that is at least partially enclosed by the proximal side the baseplate 40 and the interior walls of the collection tube 62. In some embodiments, two or more wires 82 may be embedded in the discharge tube 55, each wire 82 connected to one or more sensors 54. In some embodiments, a wire (or a plurality of wires) may be positioned to run through the cavity in the discharge tube 55. In some embodiments, a wire (or a plurality of wires) may run along a portion of the outside of the discharge tube 55.

A sensor 54 can communicate information to the computer system 83. The processing system can analyze the signal produced by the sensor 54 and determine if a signal is indicative of the fluid or characteristic the respective sensor is configured to detect, and if so processing system may provide an alert or indication that the fluid or characteristic has been detected. The computer system 83 may determine other information relating to the sensed information. For example, it may track when urine is discharged and calculate the frequency of urine discharge. This information can be tracked and compared over a time period to help determine a condition of a patient. Any sensed information can also be tracked over a time period, and used to help determine a change in the patient's health or condition. In some embodiments, the computer system 83 can display sensed information on a display 84. The display 84 may be visible to the patient or to medical practitioner. In some embodiments, the computer system 83 can provide information to a mobile device 85 or another system 86 (e.g., a medical facility system). For example, the computer system 83 can provide an alert to a medical practitioner, or a patient, of the sensed information. In some embodiments, the alert can be a visible alert, an audible alert, and/or a mechanical sensory alert (e.g., a vibration) may be provided to a mobile device of a medical practitioner, a patient, or another person (a friend or relative). For example, the alert may be provided at the computer system 83, on the display 84, on a mobile device 85, on the system 86 of a medical facility. The transmission of information from the computer system 83 to another system 86 or a mobile device 85 be on a wired (e.g., WAN or LAN) or wireless communication channel (e.g., Wi-Fi, cellular, Bluetooth).

Figure 35:
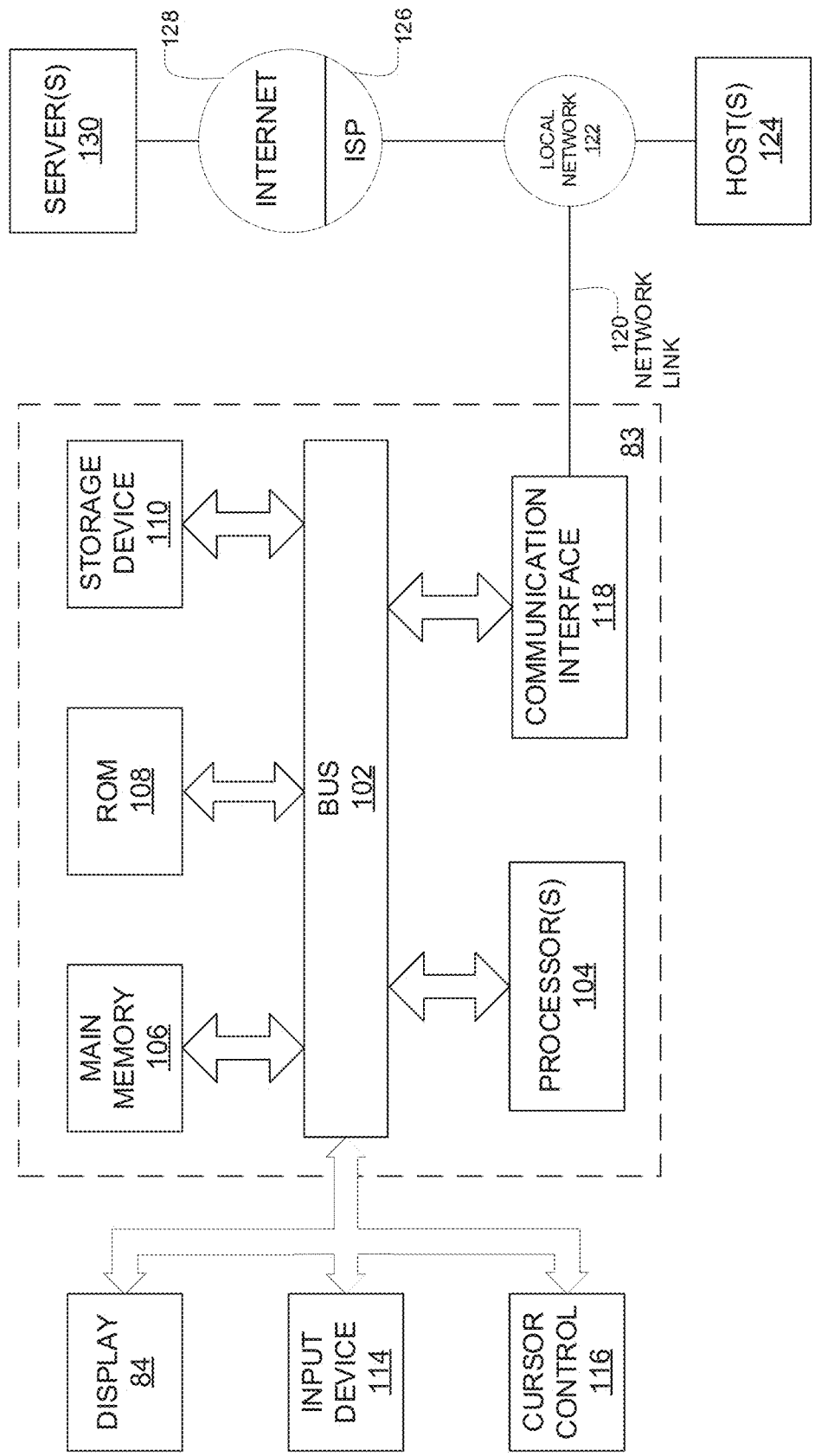
FIG. 35 is diagram illustrating certain functionality of computer system that can receive information from a sensor in a fluid collection apparatus and provide information (for example, an alert) associated with the sensor to another computer system or mobile device.

FIG. 35 is a block diagram that illustrates features which can be included in a computer system 83 upon which various functionality may be implemented. For example, providing information detected by a sensor 54 on the fluid collection apparatus. In the example illustrated in FIG. 35, computer system 83 includes a bus 102 or other communication mechanism for communicating information, and a hardware processor, or multiple processors, 104 coupled with bus 102 for processing information. Hardware processor(s) 104 may be, for example, one or more general purpose microprocessors. Computer executable instructions that perform can be stored in memory 106 and executed by the one or more hardware processors 104. The computer system 83 also includes a main memory 106, such as a random access memory (RAM), cache and/or other dynamic storage devices, coupled to bus 102 for storing information and instructions to be executed by processor 104. Main memory 106 also may be used for storing temporary variables or other intermediate information during execution of instructions to be executed by processor 104. Such instructions, when stored in storage media accessible to processor 104, render computer system 83 into a special-purpose machine that is customized to perform the operations specified in the instructions. In an example, the main memory 106 can include instructions that establish, peer-to-peer wireless interfaces with two or more fluid collection apparatus to receive information from sensors in the fluid collection apparatus. In an example, the main memory 106 can include instructions that receive data from a fluid collection apparatus via a P2P wireless communication channel (interface), transmit, uplink transmission data to a cellular network to a mobile device 85.

Computer system 83 further includes a read only memory (ROM) 108 or other static storage device coupled to bus 102 for storing static information and instructions for processor 104. A storage device 110 can be coupled to bus 102 for storing information and instructions. Computer system 83 may be coupled via the bus 102 to a display 84, e.g., an LCD display (or touch screen), for displaying information to a computer user. An input device 114, including alphanumeric and other keys, is coupled to bus 102 for communicating information and command selections to processor 104. In some implementations (e.g., a mobile device with a touch-screen) the input device incorporated in the display. In some embodiments, another type of user input device is cursor control 116, such as a mouse, a trackball, or cursor direction keys for communicating direction information and command selections to processor 104 and for controlling cursor movement on display 84. In some embodiments, the same direction information and command selections as cursor control may be implemented via receiving touches on a touch screen without a cursor.

Computing system 83 may include a user interface module to implement a GUI that may be stored in a mass storage device as computer executable program instructions that are executed by the computing device(s) (e.g., providing information or alerts to other computing systems). Computer system 83 may further, as described below, implement the techniques described herein using customized hard-wired logic, one or more ASICs or FPGAs, firmware and/or program logic which in combination with the computer system causes or programs computer system 83 to be a special-purpose machine. According to one embodiment, the techniques herein are performed by computer system 83 in response to processor(s) 104 executing one or more sequences of one or more computer readable program instructions contained in main memory 106. Such instructions may be read into main memory 106 from another storage medium, such as storage device 110. Execution of the sequences of instructions contained in main memory 106 causes processor(s) 104 to perform the process steps described herein. In alternative embodiments, hard-wired circuitry may be used in place of or in combination with software instructions.

Various forms of computer readable storage media may be involved in carrying one or more sequences of one or more computer readable program instructions to processor 104 for execution. The instructions received by main memory 106 may optionally be stored on storage device 110 either before or after execution by processor 104. Computer system 83 also includes a communication interface 118 coupled to bus 102. Communication interface 118 can provide a two-way data communication coupling to a network link 120 that is connected to a local network 122, or another device. For example, communication interface 118 may be an integrated services digital network (ISDN) card, cable modem, satellite modem, or a modem to provide a data communication connection to a corresponding type of telephone line. As another example, communication interface 118 may be a local area network (LAN) card to provide a data communication connection to a compatible LAN (or WAN component to communicate with a WAN). Wireless links may also be implemented. In some examples, cellular links may be implemented in the communication interface 118. In any such implementation, communication interface 118 can send and receive electrical, electromagnetic or optical signals that carry digital data streams representing various types of information.

Network link 120 typically provides data communication through one or more networks to other data devices. For example, network link 120 may provide a connection through local network 122 to a host computer 124 or to data equipment operated by an Internet Service Provider (ISP) 126. ISP 126 in turn provides data communication services through the world wide packet data communication network (the "Internet" 128). Local network 122 and Internet 128 both use electrical, electromagnetic or optical signals that carry digital data streams. The signals through the various networks and the signals on network link 120 and through communication interface 118, which carry the digital data to and from computer system 83, are example forms of transmission media.

Computer system 83 can send messages and receive data, including program code, through the network(s), network link 120 and communication interface 118. In the Internet example, a server 130 might transmit a requested code for an application program through Internet 128, ISP 126, local network 122 and communication interface 118. The received code may be executed by processor 104 as it is received, and/or stored in storage device 110, or other non-volatile storage for later execution.

Accordingly, in an embodiment, the computer system 83 comprises a non-transitory computer storage medium storage device 110 configured to at least store information related to wireless communications. The computer system 83 can also include non-transitory computer storage medium storage that stores instructions for the one or more processors 104 to execute a process (e.g., a method) for communicating to a cellular network on two or more parallel communication connections.

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure. For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a memory card/stick, having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. For example, any of the processes, methods, algorithms, elements, blocks, applications, or other functionality (or portions of functionality) described in the preceding sections may be embodied in, and/or fully or partially automated via, electronic hardware such application-specific processors (e.g., application-specific integrated circuits (ASICs)), programmable processors (e.g., field programmable gate arrays (FPGAs)), application-specific circuitry, and/or the like (any of which may also combine custom hard-wired logic, logic circuits, ASICs, FPGAs, etc. with custom programming/execution of software instructions to accomplish the techniques).

Any of the above-mentioned processors, and/or devices incorporating any of the above-mentioned processors, may be referred to herein as, for example, "computers," "computer devices," "computing devices," "hardware computing devices," "hardware processors," "processing units," and/or the like. Computing devices of the above-embodiments may generally (but not necessarily) be controlled and/or coordinated by operating system software. In other embodiments, the computing devices may be controlled by a proprietary operating system. Conventional operating systems control and schedule computer processes for execution, perform memory management, provide file system, networking, I/O services, and provide a user interface functionality, such as a graphical user interface ("GUI"), among other things.

It should be recognized that the described apparatus may be adapted for use with animals other than humans. For instance, there is a need for taking and analyzing urine samples of farm animals such as horses, mules, cows, and non-farm animals and wild mammals.

Example Embodiments

Embodiment 1. A fluid collector apparatus comprising: a vented housing including a rear housing having a proximal end, a distal end, and a vent extending through a surface of the rear housing, the distal end including a circular first aperture, the proximal end including an outer edge that surrounds a perimeter of a second aperture, the perimeter of the second aperture being larger than a perimeter of the first aperture; a front housing having a proximal end and a distal end, the proximal end having an outer edge that defines a perimeter of a first aperture and the distal end having an outer edge that defines a perimeter of a second aperture, the proximal end of the rear housing releasably coupled to the distal end of the front housing; a grommet positioned in the rear housing first aperture such that a portion of the grommet extends inside of the rear housing and a portion of the grommet extends exterior to the rear housing; a baseplate positioned inside the vented housing, the baseplate having a distal side aligned towards the distal end of the rear housing and a proximal side opposite the distal side, the baseplate having a circumferential angled side surface on an outer portion of a circumferential edge wall, the edge wall extending from a proximal surface of the baseplate where a cross-sectional diameter of a distal portion of the edge wall is larger than a cross-sectional diameter of a proximal portion of the edge wall, the angled side surface positioned proximate to an inside surface of the vented housing, the baseplate including a main aperture for communicating fluids extending through a portion of the baseplate and a valve aperture extending through the baseplate between the main aperture and the side surface of the baseplate; a discharge tube having a distal end and a proximal end, the proximal end extending through the grommet and into the distal side of the baseplate, the discharge tube coupled to the baseplate; an elastomeric collection tube having a distal end and a proximal end, the distal end extending into the vented housing through the first aperture of the front housing and around and past the baseplate to a termination point within the vented housing such that the baseplate is inside the collection tube, the baseplate and the vented housing configured such that the collection tube is pinched and held in place with an interference fit between the baseplate and an inside surface of the vented housing; a valve positioned in the vented housing and mounted in a respective valve aperture, the valve configured to allow air to flow from inside of the vented housing through the valve and into the collection tube; and a urethra tube positioned in the proximal end of the collection tube, the urethra tube configured to interface with a person to collect urine.

Embodiment 2. The apparatus of embodiment 1, further comprising a moisture sensor positioned in the housing and adapted to produce a first signal when fluid is detected in the collection tube.

Embodiment 3. The apparatus of embodiment 2, further comprising a vacuum pump coupled to the distal end of the interconnection tube and a collection vessel, the vacuum pump configured to be activated by the first signal to produce a vacuum in the interconnection tube to move fluid in the collection tube to the collection vessel.

Embodiment 4. The apparatus of embodiment 1 or 2, wherein the baseplate includes two valve apertures.

Embodiment 5. The apparatus of embodiment 4, wherein the valve includes two valves.

Embodiment 6. The apparatus of embodiment 1 or 2, wherein the baseplate includes three valve apertures.

Embodiment 7. The apparatus of embodiment 6, wherein the valve includes three valves.

Embodiment 8. The apparatus of embodiment 1 or 2, wherein the baseplate includes four valve apertures.

Embodiment 9. The apparatus of embodiment 8, wherein the valve includes four valves.

Embodiment 10. The apparatus of any one of embodiments 1 to 9, wherein the valve is a one-way valve.

Embodiment 11. The apparatus of any one of embodiments 1 to 10, wherein the baseplate is disc-shaped.

Embodiment 12. The apparatus of any one of embodiments 1 to 11, wherein the baseplate side includes a circumferential ridge positioned between the angled side surface and the distal side of the baseplate.

Embodiment 13. The apparatus of embodiment 13, wherein the baseplate includes at least two circumferential ridges positioned between the angled side surface and the distal side of the baseplate.

Embodiment 14. The apparatus of embodiment 12 or 13, wherein each circumferential ridge contacts the collection tube and holds the collection tube in an interference fit against an inside portion of the vented housing.

Embodiment 15. The apparatus of any one of embodiments 1 to 15, wherein the angled side surface contacts the collection tube and holds the collection tube in an interference fit against an inside portion of the vented housing.

Embodiment 16. The apparatus of embodiment 15, wherein the angled side surface contacts the collection tube and holds the collection tube in an interference fit against an inside portion of the vented housing.

Embodiment 17. The apparatus of embodiment 15, wherein the angled side surface and/or each circumferential ridge compresses the collection tube and holds the collection tube against an inside portion of the vented housing.

Embodiment 18. The apparatus of any one of embodiments 1 to 17, wherein the main aperture is in a center portion of the baseplate.

Embodiment 19. The apparatus of any one of embodiments 1 to 18, wherein the main aperture is aligned with an axis of the baseplate.

Embodiment 20. The apparatus of any one of embodiments 1 to 19, wherein the proximal end of the discharge tube extends into the main aperture and at least partially through at least a portion of the baseplate.

Embodiment 21. The apparatus of any one of embodiments 1 to 19, wherein the proximal end of the discharge tube extends and at least partially through a portion of the baseplate.

Embodiment 22. The apparatus of any one of embodiments 1 to 21, further comprising an O-ring positioned around the main aperture.

Embodiment 23. The apparatus of embodiment 22, wherein the O-ring fits around the proximal end of the discharge tube and couples the discharge tube to the baseplate.

Embodiment 24. The apparatus of embodiment 23, wherein the valve includes a proximal end that extends through the baseplate.

Embodiment 25. The apparatus of embodiment 24, wherein the proximal end of the valve includes a projection that contacts the O-ring and couples the valve to the baseplate.

Embodiment 26. The apparatus of embodiment 24 or 25, wherein the proximal end of the valve includes a projection that extends over a portion of the O-ring and couples the O-ring to the baseplate.

Embodiment 27. The apparatus of embodiment 24, wherein the proximal end of the valve includes a projection that extends over a portion of the O-ring and couples the valve and the O-ring to the baseplate.

Embodiment 28. The apparatus of any one of embodiments 1 to 27, wherein the valve is a one-way valve.

Embodiment 29. The apparatus of any one of embodiments 1 to 28, wherein an axis of the valve aperture is aligned in parallel with an axis of the main aperture.

Embodiment 30. The apparatus of any one of embodiments 1 to 28, wherein an axis of the valve aperture is aligned at angle with an axis of the main aperture.

Embodiment 31. The apparatus of any one of embodiments 1 to 30, wherein an axis extends through the center of the valve aperture such that the axis of the valve aperture is angled towards a center axis of the main aperture.

Embodiment 32. The apparatus of any one of embodiments 1 to 31, wherein the collection tube comprises silicon.

Embodiment 33. The apparatus of any one of embodiments 1 to 32, wherein the termination point is within the rear housing.

Embodiment 34. The apparatus of any one of embodiments 1 to 33, wherein the baseplate is positioned in the vented housing such that the baseplate angled side surface holds the collection tube against a portion of an inside surface of the front housing.

Embodiment 35. The apparatus of any one of embodiments 1 to 34, wherein the contact between the baseplate and the collection tube, and the collection tube and the inside surface of the vented housing is the only coupling mechanism of the collection tube to the vented housing.

Embodiment 36. The apparatus of any one of embodiments 1 to 35, wherein the urethra tube is positioned inside the proximal end of the collection tube.

Embodiment 37. The apparatus of any one of embodiments 1 to 36, wherein the urethra tube includes a distal end and a proximal end, the distal end of the urethra being positioned inside the collection tube extending towards the baseplate and the proximal end of the urethra tube positioned inside the proximal end of the collection tube.

Embodiment 38. The apparatus of any one of embodiments 1 to 37, wherein the collection tube is stretched over the urethra tube such that the collection tube conforms to the shape of the urethra tube.

Embodiment 39. The apparatus of any one of embodiments 1 to 38, wherein the urethra tube is shaped and sized to interface with a urethra of a female subject.

Embodiment 40. The apparatus of any one of embodiments 1 to 39, wherein the urethra tube includes a flared proximal end contoured for sealing a female's urethra.

Embodiment 41. The apparatus of any one of embodiments 1 to 38, wherein the urethra tube is shaped and sized to interface with a urethra of a male subject.

Embodiment 42. The apparatus of any one of embodiments 1 to 38 and 41, wherein the urethra tube is contoured for a tight-fitting around a penis received therein.

Embodiment 43. The apparatus of any one of embodiments 1 to 42, further comprising a vacuum pump coupled to the distal end of the discharge tube.

Embodiment 44. The apparatus of any one of embodiments 1 to 43, further comprising a sensor coupled to the baseplate and configured to detect the presence of urine.

Embodiment 45. The apparatus of any one of embodiments 1 to 44, further comprising a garment having an interface through which the collection tube extends.

Embodiment 46. A fluid collector apparatus comprising: a vented housing including
a rear housing having a proximal end, a distal end, and a vent extending through a surface of the rear housing; a front housing having a proximal end and a distal end, the proximal end having an outer edge that defines a perimeter of a first aperture and the distal end having an outer edge that defines a perimeter of a second aperture, the proximal end of the rear housing releasably coupled to the distal end of the front housing; a baseplate positioned inside the vented housing, the baseplate having a circumferential angled side surface on an outer portion of a circumferential edge wall, the angled side surface positioned proximate to an inside surface of the vented housing, the baseplate including a main aperture for communicating fluids extending through a portion of the baseplate and a valve aperture extending through the baseplate between the main aperture and the side surface; a discharge tube having a distal end extending outside of the vented housing and a proximal end coupled to the baseplate; an elastomeric collection tube having a distal end and a proximal end, the distal end extending into the vented housing through the first aperture of the front housing and around and past the baseplate to a termination point within the vented housing such that the baseplate is positioned inside the collection tube and normal to the collection tube with the angled side surface contacting an inside surface of the collection tube, the collection tube held in place with an interference fit between the baseplate and an inside surface of the vented housing; and a valve positioned in the vented housing and extending through the valve aperture, the valve configured to allow air to flow from inside of the vented housing through the valve and into the collection tube; and a urethra tube positioned in the proximal end of the collection tube such that the proximal end of the collection tube conforms to the shape of the urethra tube.

Embodiment 47. A fluid collector apparatus comprising: a vented housing including a rear housing having a proximal end, a distal end, and a vent extending through a surface of the rear housing; a front housing having a proximal end and a distal end, the proximal end having an outer edge that defines a perimeter of a first aperture and the distal end having an outer edge that defines a perimeter of a second aperture, the proximal end of the rear housing releasably coupled to the distal end of the front housing.

Embodiment 48. A fluid collector apparatus comprising: a housing; a baseplate positioned inside the housing, the baseplate having a circumferential angled side surface on an outer portion of a circumferential edge wall, the angled side surface positioned proximate to an inside surface of the housing, the baseplate including a main aperture for communicating fluids extending through a portion of the baseplate and a valve aperture extending through the baseplate between the main aperture and the side surface.

Embodiment 49. A fluid collector apparatus comprising: an elastomeric collection tube having a distal end and a proximal end, the distal end configured to extend into a housing through an aperture of the housing; and a urethra tube positioned in the proximal end of the collection tube such that the proximal end of the collection tube conforms to the shape of the urethra tube.

Embodiment 50. A method of collecting fluid from a urethra, the method comprising providing a fluid collection apparatus having a vented housing including a rear housing having a proximal end, a distal end, and a vent extending through a surface of the rear housing, and a front housing having a proximal end and a distal end, the proximal end having an outer edge that defines a perimeter of a first aperture and the distal end having an outer edge that defines a perimeter of a second aperture, the proximal end of the rear housing releasably coupleable to the distal end of the front housing; a baseplate, having a circumferential angled side surface on an outer portion of a circumferential edge wall, the angled side surface configured to be positioned proximate to an inside surface of the vented housing, the baseplate including a main aperture for communicating fluids extending through a portion of the baseplate and a valve aperture extending through the baseplate between the main aperture and the side surface; and a valve mounted to the baseplate and through each of the valve apertures; coupling a proximal end of discharge tube to the baseplate such that a distal end extends outside of the vented housing through an aperture in the distal end of the rear housing; coupling a distal end of an elastomeric collection tube to the baseplate by inserting the baseplate into the distal end of the collection tube such that the distal end of the collection tube extends into the vented housing past the baseplate to a termination point within the vented housing such that the baseplate is positioned inside the collection tube and normal to the collection tube with the angled side surface contacting an inside surface of the collection tube and the collection tube held in place with an interference fit between the baseplate and an inside surface of the vented housing; inserting a urethra tube in a proximal end of the collection tube such that the proximal end of the collection tube conforms to the shape of the urethra tube; and receiving a body fluid in the urethra tube.

Embodiment 51. A fluid collector apparatus in any one of the embodiments described herein, comprising: a garment including an elastomeric collection tube having a distal end and a proximal end, the distal end configured to extend into a housing through an aperture of the housing; and a urethra tube positioned in the proximal end of the collection tube such that the proximal end of the collection tube conforms to the shape of the urethra tube.

Embodiment 52. The fluid collector apparatus of embodiment 51, where the garment further includes an interface, and the proximal end of the collection tube extends through the interface to an interior portion of the garment.

Embodiment 53. A fluid collector apparatus comprising: a housing; a baseplate positioned inside the housing, the baseplate having a circumferential angled side surface on an outer portion of a circumferential edge wall, the angled side surface positioned proximate to an inside surface of the housing, the baseplate including a main aperture for communicating fluids extending through a portion of the baseplate; and a sensor positioned within the housing, the sensor configured to sense a substance in the fluid collector apparatus and provide a signal indicative of the sensed substance.

Embodiment 54. The fluid collector apparatus of embodiment 53, wherein the sensor is configured to sense one of moisture, blood, sodium chloride, protein, or calcium.

Embodiment 55. The fluid collector apparatus of embodiment 53, further comprising one or more additional sensors.

Embodiment 56. The fluid collector apparatus of embodiment 55, wherein the sensors are positioned in a chamber that is defined in part by a proximal side of the baseplate and the interior surface of a distal end of a collection tube coupled to the baseplate.

Embodiment 57. A fluid collector apparatus in any one of the embodiments described herein, further comprising a sensor positioned within the housing, the sensor configured to sense a substance in the fluid collector apparatus and provide a signal indicative of the sensed substance.

Embodiment 58. The fluid collector apparatus of embodiments 57, wherein the sensor is configured to sense one of moisture, blood, sodium chloride, protein, or calcium.

Embodiment 59. The fluid collector apparatus of any one of embodiments 57 or 58, further comprising one or more additional sensors.

Embodiment 60. The fluid collector apparatus of any one of embodiments 57-59, wherein the sensors are positioned in a chamber that is defined in part by a proximal side of the baseplate and the interior surface of a distal end of a collection tube coupled to the baseplate.

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects should not be taken to imply that the terminology is being re-defined herein to be restricted to including any specific characteristics of the features or aspects of the technology with which that terminology is associated.

In this description, embodiments are described as a plurality of individual parts, and methods as a plurality of individual steps and this is solely for the sake of illustration. Accordingly, it is contemplated that some additional parts or steps may be added, some parts or steps may be changed or omitted, and the order of the parts or steps may be re-arranged while maintaining the sense and understanding of the apparatus and methods as claimed.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Headings are included herein for reference and to aid in locating various sections. These headings are not intended to limit the scope of the concepts described with respect thereto. Such concepts may have applicability throughout the entire specification.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

The phrase "based on" does not mean "based only on," unless expressly specified otherwise. In other words, the phrase "based on" describes both "based only on" and "based at least on." Unless otherwise explicitly stated, articles such as "a" or "an" should generally be interpreted to include one or more described items. Accordingly, phrases such as "a device configured to" are intended to include one or more recited devices.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures may be combined, interchanged or excluded from other embodiments.

The above description also discloses methods and materials of the present application. The devices and methods of a fluid collection apparatus described herein may be susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims. Applicant reserves the right to submit claims directed to combinations and sub-combinations of the disclosed inventions that are believed to be novel and non-obvious. Inventions embodied in other combinations and sub-combinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

What is claimed is:

1. A fluid collector apparatus comprising:
   a vented housing having a proximal end and a distal end, the housing having a first aperture on the proximal end and a second aperture on the distal end;
   a baseplate positioned inside the vented housing, the baseplate including
      a distal side,
      a proximal side opposite the distal side,
      a circumferential side surface between the distal side and the proximal side,
   wherein the circumferential side surface of the baseplate includes a ridge,
      a main aperture extending through a portion of the baseplate, and a valve aperture extending through a portion of the baseplate;

a collection tube having a distal end and a proximal end, the distal end extending into the vented housing through the first aperture around the baseplate to a termination point within the vented housing such that the collection tube is positioned between the side surface of the baseplate and an inside surface of the vented housing;

a discharge tube having a distal end and a proximal end, the proximal end extending into the vented housing through the second aperture and coupled to the baseplate;

a valve positioned in the vented housing and mounted in the valve aperture, the valve configured to allow air to flow from inside of the vented housing through the valve and into an interior volume defined by the collection tube and the proximal side of the baseplate; and a urethra tube positioned in the proximal end of the collection tube, the urethra tube configured to deform a portion of the collection tube to an exterior shape of the urethra tube.

2. The apparatus of claim 1, wherein the valve is configured to allow air to flow from inside of the vented housing through the valve and into the interior volume when the pressure differential between the air pressure in the rear housing and the air pressure in the interior volume that suction is maintained in the collection tube.

3. The apparatus of claim 2, wherein the valve is configured to allow air to flow from the inside of the vented housing through the valve and into the interior volume such that a suction of about 3 to 18 inches of Hg is maintained in the collection tube.

4. The apparatus of claim 1, wherein the urethra tube includes a flared proximal end contoured for sealing around a female's urethra.

5. The apparatus of claim 1, wherein the urethra tube is shaped and sized for interfacing with a male's urethra.

6. The apparatus of claim 1, wherein the baseplate circumference is circular-shaped.

7. The apparatus of claim 1, wherein the baseplate includes an angled side surface adjacent to the proximal side of the baseplate.

8. The apparatus of claim 1, wherein the ridge contacts the collection tube such that the distal end of the collection tube is held in an interference fit between the ridge and the vented housing.

9. The apparatus of claim 1, wherein the circumferential ridge contacts the distal end of the collection tube and holds the distal end of the collection tube in an interference fit against the inside surface of the vented housing.

10. The apparatus of claim 1, wherein the main aperture is in a center portion of the baseplate.

11. The apparatus of claim 1, wherein the proximal end of the discharge tube extends into the main aperture and at least partially through the baseplate.

12. The apparatus of claim 1, wherein the proximal end of the discharge tube is coupled to the distal side of the baseplate.

13. The apparatus of claim 1, further comprising an O-ring positioned around the proximal end of the discharge tube coupling the discharge tube to the distal side of the baseplate.

14. A fluid collector apparatus comprising:

a vented housing having a proximal end and a distal end;

a baseplate positioned inside the vented housing, the baseplate having a distal side facing the distal end of the housing and a proximal side opposite the distal side, the baseplate including a circumferential side surface and a main aperture extending through a portion of the baseplate;

an elastomeric collection tube having a distal end and a proximal end, the distal end extending into the vented housing and around the baseplate to a termination point within the vented housing such that a portion of the distal end of the collection tube is positioned between the baseplate and an inside surface of the housing, wherein the baseplate circumferential side surface includes a ridge, and wherein the ridge contacts the collection tube and holds the collection tube in an interference fit against an inside surface of the housing;

a valve configured to allow air to flow from the vented housing into an interior volume defined by the collection tube and the proximal side of the baseplate; and a urethra tube positioned in the proximal end of the elastomeric collection tube, the urethra tube configured to deform a portion of the collection tube to an exterior shape of the urethra tube.

15. The apparatus of claim 14, wherein the urethra tube includes a flared proximal end contoured for sealing around a female's urethra.

16. The apparatus of claim 14, wherein the baseplate circumference is circular-shaped.

17. The apparatus of claim 14, wherein the fluid collection apparatus has a sensor positioned in a chamber formed in part by the distal side of the baseplate and the inside surface of the collection tube, the sensor configured to transmit a signal, indicative of fluid in the chamber, to a processing system.

18. The apparatus of claim 17, wherein the sensor is configured to detect moisture, sugar, blood, sodium chloride, protein, or calcium.

* * * * *

UNITED STATES PATENT AND TRADEMARK OFFICE
CERTIFICATE OF CORRECTION

PATENT NO. : 11,903,866 B2
APPLICATION NO. : 17/657658
DATED : February 20, 2024
INVENTOR(S) : Landon Duval It is certified that error appears in the above-identified patent and that said Letters Patent is hereby corrected as shown below:

In the Drawings

Sheet 14 of 37 (FIG. 25A), Line 9 (Approx.), Delete "(FIG. 26B)" and insert -- (FIG. 25C) --.

In the Specification

Column 9, Line 65, Delete "1"" and insert -- 1", --.

Column 9, Line 66, Delete "3"." and insert -- 3", --.

Column 12, Line 10, Delete "are can" and insert -- can --.

Column 12, Line 24, Delete "FIG." and insert -- FIGS. --.

Column 12, Line 25, Delete "FIG." and insert -- FIGS. --.

Column 14, Line 27, Delete "the or" and insert -- or --.

Column 17, Line 17, Delete "FIG." and insert -- FIGS. --.

Column 17, Line 25, Delete "FIG." and insert -- FIGS. --.

Column 17, Line 33, Delete "FIG." and insert -- FIGS. --.

Column 17, Line 42, Delete "the such" and insert -- such --.

Column 18, Line 32, Delete "FIG." and insert -- FIGS. --.

Column 18, Line 56, Delete "44°," and insert -- 44°, 45°, --.

Signed and Sealed this
Twenty-second Day of October, 2024

Katherine Kelly Vidal
*Director of the United States Patent and Trademark Office*

CERTIFICATE OF CORRECTION (continued)
U.S. Pat. No. 11,903,866 B2

Column 19, Line 1, Delete "FIG." and insert -- FIGS. --.

Column 19, Line 33, Delete "FIG." and insert -- FIGS. --.

Column 23, Line 43, Delete "29," and insert -- 29°, --.

Column 24, Line 38, Delete "orientation" and insert -- orientation. --.

Column 25, Line 4, Delete "orientation," and insert -- orientation. --.

Column 25, Line 46, Delete "orientation," and insert -- orientation. --.

Column 26, Line 17, Delete "orientation," and insert -- orientation. --.